(12) United States Patent
Fuchter et al.

(10) Patent No.: US 12,377,119 B2
(45) Date of Patent: *Aug. 5, 2025

(54) NATURAL KILLER CELLS

(71) Applicant: IMPERIAL COLLEGE INNOVATIONS LIMITED, London (GB)

(72) Inventors: Matthew J. Fuchter, London (GB); Amaia Uriz Huarte, London (GB); Hugh J. M. Brady, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 1110 days.

This patent is subject to a terminal disclaimer.

(21) Appl. No.: 17/255,091

(22) PCT Filed: Jun. 26, 2019

(86) PCT No.: PCT/GB2019/051803
§ 371 (c)(1),
(2) Date: Dec. 22, 2020

(87) PCT Pub. No.: WO2020/002911
PCT Pub. Date: Jan. 2, 2020

(65) Prior Publication Data
US 2022/0073880 A1 Mar. 10, 2022

(30) Foreign Application Priority Data
Jun. 26, 2018 (GB) .................................. 1810486

(51) Int. Cl.
| | | |
|---|---|---|
| *A61K 35/17* | (2025.01) |
| *A61K 31/47* | (2006.01) |
| *C07D 217/26* | (2006.01) |
| *C07D 405/06* | (2006.01) |
| *C07D 409/06* | (2006.01) |
| *C07D 413/06* | (2006.01) |
| *C07D 417/06* | (2006.01) |
| *C12N 5/0783* | (2010.01) |

(52) U.S. Cl.
CPC .............. *A61K 35/17* (2013.01); *A61K 31/47* (2013.01); *C07D 217/26* (2013.01); *C07D 405/06* (2013.01); *C07D 409/06* (2013.01); *C07D 413/06* (2013.01); *C07D 417/06* (2013.01); *C12N 5/0646* (2013.01); *C12N 2501/125* (2013.01); *C12N 2501/2307* (2013.01); *C12N 2501/2315* (2013.01); *C12N 2501/26* (2013.01); *C12N 2501/42* (2013.01); *C12N 2501/999* (2013.01); *C12N 2506/11* (2013.01)

(58) Field of Classification Search
CPC ...... A61K 35/17; A61K 31/47; C12N 5/0646; C12N 2501/125; C12N 2501/2307; C12N 2501/2315; C12N 2501/26; C12N 2501/42; C12N 2501/999; C12N 2506/11; C12N 2501/38; C07D 217/26; C07D 405/06; C07D 409/06; C07D 413/06; C07D 417/06
See application file for complete search history.

(56) References Cited

U.S. PATENT DOCUMENTS

| | | | |
|---|---|---|---|
| 9,175,266 B2 * | 11/2015 | Peled ................. | A61K 39/4644 |
| 11,559,547 B2 * | 1/2023 | Brady ................. | C12N 5/0646 |
| 11,566,226 B2 * | 1/2023 | Brady ................. | A61K 39/464 |
| 2012/0282693 A1 | 11/2012 | Kimbrel et al. | |

FOREIGN PATENT DOCUMENTS

| | | | |
|---|---|---|---|
| CN | 103710304 | 4/2014 | |
| JP | 2002-536364 | 10/2002 | |
| JP | 2016-187341 | 11/2016 | |
| WO | 98/53814 | 12/1998 | |
| WO | 00/46204 | 8/2000 | |
| WO | 2008/137720 | 11/2008 | |
| WO | 2011/080740 | 7/2011 | |
| WO | 2012/128622 | 9/2012 | |
| WO | 2013/033310 | 3/2013 | |
| WO | 2015/103527 | 7/2015 | |
| WO | 2018/158587 | 9/2018 | |
| WO | WO-2018158587 A1 * | 9/2018 | ......... A61K 31/4535 |
| WO | 2018/178666 | 10/2018 | |
| WO | WO-2018178661 A1 * | 10/2018 | ......... B01D 53/0446 |
| WO | WO-2018178666 A1 * | 10/2018 | ............. A61K 35/17 |

OTHER PUBLICATIONS

Notification of Reasons for Refusal issued Jun. 5, 2023 in corresponding Japanese Patent Application No. 2020-571746, English language translation.
Weir, E.C. et al. "Tricyclic hydantoins and thiohydantoins of phenylalanine", Chimika Chronika, New Series, vol. 18, pp. 3-17, 1989.
Das, S. et al. "Selective Rhodium-catalyzed reduction of tertiary amides in amino acid esters and peptides", Angew. Chem. Int. Ed., vol. 54, pp. 12389-12393, 2015.
Gascoyne, D. et al. "The basic leucine zipper transcription factor E4BP4 is essential for natural killer cell development", Nature Immunology, vol. 10, No. 10, pp. 1118-1124, 2009.
Kim, N. and Y. Fukada., "Molecular mechanism of time resetting of the circadian clock", Comparative Endocrinology vol. 36, No. 137, pp. 118-126, 2010.

(Continued)

*Primary Examiner* — Christopher M Babic
*Assistant Examiner* — Kimberly A Aron
(74) *Attorney, Agent, or Firm* — Wenderoth, Lind & Ponack, L.L.P.

(57) ABSTRACT

This invention relates to Natural Killer (NK) cell populations, to methods of producing the same and therapeutic applications thereof. More specifically, the invention relates to the expansion of IMK cells by increasing the expression of specific transcription factors associated with NK cell production.

22 Claims, 7 Drawing Sheets

Specification includes a Sequence Listing.

(56) References Cited

OTHER PUBLICATIONS

Beck, R.C. et al. "The Notch ligands Jagged2, Delta1 and Delta4 induce differentiation and expansion of functional human NK cells from CD34+ cord blood hematopoietic progenitor cells", Biol Blood Marrow Transplant, Vo. 15, pp. 1026-1037, 2009.

International Search Report and Written Opinion issued Nov. 4, 2019 in corresponding International (PCT) Patent Application No. PCT/GB2019/051803.

Kato et al., "1-azabicyclo compounds. 20. Synthesis of hexahydroisoquino [3,2-c] [1,4] benzodiazepine and related compounds and formation of 6-methyl-hexahydro-5H-dibenzo [b,g] [1,5] diazacycloundecine from hexahydroisoquino [3,2-c] [1,4] benzodiazepin-13-one", Chem. Abstracts, 1975, XP002794692.

Akiyama et al., "Preparation of pyrazolecarboxamide derivatives as plant disease control agents", Chem. Abstracts, 1997, XP002794693.

Ryder et al., "CCK and/or gastrin receptor ligands", Chem. Abstracts, 1994, XP002794694.

Zheng et al., "(3S)-N-(-Aminoacyl)-1,2,3,4-tetrahydroisoquinolines, a class of novel antithrombotic agents: Synthesis, bioassay, 3D QSAR, and ADME analysis", Chem. Abstracts, 2008, XP002794695.

Noel, et al., "Synthesis and SAR of tetrahydroisoquinolines as Rev-erbα agonists" Bioorganic & Medicinal Chemistry Letters, 22(11):3739-3742 (2012).

Kojetin et al., "Identification of SR8278, a Synthetic Antagonist of the Nuclear Heme Receptor REV-ERB", ACS Chemical Biology, 6(2):131-134 (2011).

"Glycine, N-(2-furanylmethyl)-N-(phenylmethyl)-, ethyl ester", Chem. Abstracts, 2012, XP002794696.

"Glycine, N-(2-furanylcarbonyl)-N-(phenylmethyl)-, ethyl ester", Chem. Abstracts, 2010, XP002794697.

Yu et al., "$T_H 17$ Cell Differentiation Is Regulated by the Circadian Clock", Science, vol. 342, pp. 727-730 (2013).

Search Report issued Feb. 28, 2019 in corresponding United Kingdom Patent Application No. GB1810486.9.

Office Action issued Jan. 15, 2025 in corresponding European Patent Application No. 19736788.1.

Office Action issued Dec. 11, 2024 in corresponding Chinese Patent Application No. 201980050463.X with English-language translation.

Office Action issued Oct. 19, 2022 in corresponding European Patent Application No. 19736788.1.

Office Action issued Oct. 4, 2024 in corresponding Australian Patent Application No. 2019293163.

Office Action issued Jul. 28, 2023 in corresponding Chinese Patent Application No. 201980050463.X with English-language translation.

Office Action issued Dec. 18, 2023 in corresponding Japanese Patent Application No. 2020-571746 with English-language translation.

* cited by examiner

SEQUENCE LISTING

```
<160> NUMBER OF SEQ ID NOS: 10

<210> SEQ ID NO 1
<211> LENGTH: 1923
<212> TYPE: DNA
<213> ORGANISM: Homo sapiens
<220> FEATURE:
<221> NAME/KEY: misc_feature
<222> LOCATION: (1833)..(1833)
<223> OTHER INFORMATION: n is a, c, g, or t

<400> SEQUENCE: 1
gcccctttct ttctcctcgt cggcccgaga gcaggaacac gataacgaag gaggcccaac      60
ttcattcaat aaggagcctg acggatttat cccagacggt agaacaaaag gaagaatatt     120
gatggatttt aaaccagagt ttttaaagag cttgagaata cggggaaatt aatttgttct     180
cctacacaca tagatagggt aaggttgttt ctgatgcagc tgagaaaaat gcagaccgtc     240
aaaaaggagc aggcgtctct tgatgccagt agcaatgtgg acaagatgat ggtccttaat     300
tctgctttaa cggaagtgtc agaagactcc acaacaggtg aggacgtgct tctcagtgaa     360
ggaagtgtgg ggaagaacaa atcttctgca tgtcggagga aacgggaatt cattcctgat     420
gaaaagaaag atgctatgta ttgggaaaaa aggcggaaaa ataatgaagc tgccaaaaga     480
tctcgtgaga agcgtcgact gaatgacctg gttttagaga acaaactaat tgcactggga     540
gaagaaaacg ccactttaaa agctgagctg ctttcactaa aattaaagtt tggtttaatt     600
agctccacag catatgctca agagattcag aaactcagta attctacagc tgtgtactttt    660 caagattacc agacttccaa atccaatgtg agttcatttg tggacgagca cgaaccctcg     720
```

```
atggtgtcaa gtagttgtat ttctgtcatt aaacactctc cacaaagctc gctgtccgat    780
gtttcagaag tgtcctcagt agaacacacg caggagagct ctgtgcaggg aagctgcaga    840
agtcctgaaa acaagttcca gattatcaag caagagccga tggaattaga gagctacaca    900
agggagccaa gagatgaccg aggctcttac acagcgtcca tctatcaaaa ctatatgggg    960
aattctttct ctgggtactc acactctccc ccactactgc aagtcaaccg atcctccagc   1020
aactccccga gaacgtcgga aactgatgat ggtgtggtag gaaagtcatc tgatggagaa   1080
gacgagcaac aggtccccaa gggccccatc cattctccag ttgaactcaa gcatgtgcat   1140
gcaactgtgg ttaaagttcc agaagtgaat tcctctgcct tgccacacaa gctccggatc   1200
aaagccaaag ccatgcagat caaagtagaa gcctttgata tgaatttga ggccacgcaa    1260 aaactttcct cacctattga catgacatct aaaagacatt tcgaactcga aaagcatagt   1320
gccccaagta tggtacattc ttctcttact cctttctcag tgcaagtgac taacattcaa   1380
gattggtctc tcaaatcgga gcactggcat caaaagaac tgagtggcaa aactcagaat    1440
agtttcaaaa ctggagttgt tgaaatgaaa gacagtggct acaaagtttc tgacccagag   1500
aacttgtatt tgaagcaggg gatagcaaac ttatctgcag aggttgtctc actcaagaga   1560
cttatagcca cacaaccaat ctctgcttca gactctgggt aaattactac tgagtaagag   1620
ctgggcattt agaaagatgt catttgcaat agagcagtcc attttgtatt atgctgaatt   1680
ttcactggac ctgtgatgtc atttcactgt gatgtgcaca tgttgtctgt ttggtgtctt   1740
tttgtgcaca gattatgatg aagattagat tgtgttatca ctctgcctgt gtatagtcag   1800
atagtcatat gcgtaaggct gtatatatta agntttatt tttgttgttc tattataaag    1860
tgtgtaagtt accagtttca ataaaggatt ggtgacaaac acagaaaaaa aaaaaaaaa    1920 aaa                                                                1923
```

<210> SEQ ID NO 2
<211> LENGTH: 462
<212> TYPE: PRT
<213> ORGANISM: Homo sapiens

<400> SEQUENCE: 2

```
Met Gln Leu Arg Lys Met Gln Thr Val Lys Lys Glu Gln Ala Ser Leu
1               5                   10                  15

Asp Ala Ser Ser Asn Val Asp Lys Met Met Val Leu Asn Ser Ala Leu
                20                  25                  30

Thr Glu Val Ser Glu Asp Ser Thr Thr Gly Glu Asp Val Leu Leu Ser
            35                  40                  45

Glu Gly Ser Val Gly Lys Asn Lys Ser Ala Cys Arg Arg Lys Arg
        50                  55                  60

Glu Phe Ile Pro Asp Glu Lys Lys Asp Ala Met Tyr Trp Glu Lys Arg
65                  70                  75                  80

Arg Lys Asn Asn Glu Ala Ala Lys Arg Ser Arg Glu Lys Arg Leu
                85                  90                  95

Asn Asp Leu Val Leu Glu Asn Lys Leu Ile Ala Leu Gly Glu Glu Asn
            100                 105                 110

Ala Thr Leu Lys Ala Glu Leu Leu Ser Leu Lys Leu Lys Phe Gly Leu
        115                 120                 125

Ile Ser Ser Thr Ala Tyr Ala Gln Glu Ile Gln Lys Leu Ser Asn Ser
    130                 135                 140

Thr Ala Val Tyr Phe Gln Asp Tyr Gln Thr Ser Lys Ser Asn Val Ser
```

```
                145                 150                 155                 160
        Ser Phe Val Asp Glu His Glu Pro Ser Met Val Ser Ser Cys Ile
                        165                 170                 175

Ser Val Ile Lys His Ser Pro Gln Ser Ser Leu Ser Asp Val Ser Glu
                        180                 185                 190

Val Ser Val Glu His Thr Gln Glu Ser Ser Val Gln Gly Ser Cys
                        195                 200                 205

Arg Ser Pro Glu Asn Lys Phe Gln Ile Ile Lys Gln Glu Pro Met Glu
                210                 215                 220

Leu Glu Ser Tyr Thr Arg Glu Pro Arg Asp Asp Arg Gly Ser Tyr Thr
        225                 230                 235                 240

Ala Ser Ile Tyr Gln Asn Tyr Met Gly Asn Ser Phe Ser Gly Tyr Ser
                        245                 250                 255

His Ser Pro Pro Leu Leu Gln Val Asn Arg Ser Ser Asn Ser Pro
                        260                 265                 270

Arg Thr Ser Glu Thr Asp Asp Gly Val Val Gly Lys Ser Ser Asp Gly
                        275                 280                 285

Glu Asp Glu Gln Gln Val Pro Lys Gly Pro Ile His Ser Pro Val Glu
                290                 295                 300

Leu Lys His Val His Ala Thr Val Val Lys Val Pro Glu Val Asn Ser
        305                 310                 315                 320

Ser Ala Leu Pro His Lys Leu Arg Ile Lys Ala Lys Ala Met Gln Ile
                        325                 330                 335

Lys Val Glu Ala Phe Asp Asn Glu Phe Glu Ala Thr Gln Lys Leu Ser
                        340                 345                 350

Ser Pro Ile Asp Met Thr Ser Lys Arg His Phe Glu Leu Glu Lys His
                        355                 360                 365

Ser Ala Pro Ser Met Val His Ser Ser Leu Thr Pro Phe Ser Val Gln
                        370                 375                 380

Val Thr Asn Ile Gln Asp Trp Ser Leu Lys Ser Glu His Trp His Gln
        385                 390                 395                 400

Lys Glu Leu Ser Gly Lys Thr Gln Asn Ser Phe Lys Thr Gly Val Val
                        405                 410                 415

Glu Met Lys Asp Ser Gly Tyr Lys Val Ser Asp Pro Glu Asn Leu Tyr
                        420                 425                 430

Leu Lys Gln Gly Ile Ala Asn Leu Ser Ala Glu Val Val Ser Leu Lys
                        435                 440                 445

Arg Leu Ile Ala Thr Gln Pro Ile Ser Ala Ser Asp Ser Gly
                450                 455                 460

<210> SEQ ID NO 3
<211> LENGTH: 2793
<212> TYPE: DNA
<213> ORGANISM: Homo sapiens

<400> SEQUENCE: 3
gggcacgagg cgctccctgg gatcacatgg tacctgctcc agtgccgcgt gcggcccggg      60
aaccctgggc tgctggcgcc tgcgcagagc cctctgtccc agggaaaggc tcgggcaaaa     120
ggcggctgag attggcagag tgaaatatta ctgccgaggg aacgtagcag ggcacacgtc     180
tcgcctcttt gcgactcggt gccccgtttc tccccatcac ctacttactt cctggttgca     240
acctctcttc ctctgggact tttgcaccgg gagctcccaga ttcgccaccc cgcagcgctg    300
cggagccggc aggcagaggc acccccgtaca ctgcagagac ccgaccctcc ttgctacctt    360
```

```
ctagccagaa ctactgcagg ctgattcccc ctacacactc tctctgctct tcccatgcaa      420
agcagaactc cgttgcctca acgtccaacc cttctgcagg gctgcagtcc ggccacccca      480
agaccttgct gcagggtgct tcggatcctg atcgtgagtc gcggggtcca ctccccgccc      540
ttagccagtg cccaggggc aacagcggcg atcgcaacct ctagtttgag tcaaggtcca      600
gtttgaatga ccgctctcag ctggtgaaga catgacgacc ctggactcca acaacaacac      660
aggtggcgtc atcacctaca ttggctccag tggctcctcc ccaagccgca ccagccctga      720
atccctctat agtgacaact ccaatggcag cttccagtcc ctgacccaag gctgtcccac      780
ctacttccca ccatccccca ctggctccct cacccaagac ccggctcgct cctttgggag      840
cattccaccc agcctgagtg atgacggctc cccttcttcc tcatcttcct cgtcgtcatc      900
ctcctcctcc ttctataatg ggagcccccc tgggagtcta caagtggcca tggaggacag      960
cagccgagtg tcccccagca agagcaccag caacatcacc aagctgaatg catggtgtt     1020 actgtgtaaa gtgtgtgggg acgttgcctc gggcttccac tacggtgtgc acgcctgcga     1080
gggctgcaag ggctttttcc gtcggagcat ccagcagaac atccagtaca aaggtgtct     1140 gaagaatgag aattgctcca tcgtccgcat caatcgcaac cgctgccagc aatgtcgctt     1200
caagaagtgt ctctctgtgg gcatgtctcg agacgctgtg cgttttgggc gcatccccaa     1260
acgagagaag cagcggatgc ttgctgagat gcagagtgcc atgaacctgg ccaacaacca     1320
gttgagcagc cagtgcccgc tggagacttc acccacccag caccccaccc caggccccat     1380
gggcccctcg ccaccccctg ctccggtccc ctcacccctg gtgggcttct cccagtttcc     1440
acaacagctg acgcctccca gatccccaag ccctgagccc acagtggagg atgtgatatc     1500
ccaggtggcc cgggcccatc gagagatctt cacctacgcc catgacaagc tgggcagctc     1560
acctggcaac ttcaatgcca accatgcatc aggtagccct ccagccacca ccccacatcg     1620
ctgggaaaat cagggctgcc cacctgcccc caatgacaac aacaccttgg ctgcccagcg     1680
tcataacgag gccctaaatg gtctgcgcca ggctccctcc tcctacccte ccacctggcc     1740 tcctggccct gcacaccaca gctgccacca gtccaacagc aacgggcacc gtctatgccc     1800
cacccacgtg tatgcagccc cagaaggcaa ggcacctgcc aacagtcccc ggcagggcaa     1860
ctcaaagaat gttctgctgg catgtcctat gaacatgtac ccgcatggac gcagtgggcg     1920
aacggtgcag gagatctggg aggatttctc catgagcttc acgcccgctg tgcgggaggt     1980
ggtagagttt gccaaacaca tcccgggctt ccgtgacctt tctcagcatg accaagtcac     2040
cctgcttaag gctggcacct ttgaggtgct gatggtgcgc tttgcttcgt tgttcaacgt     2100
gaaggaccag acagtgatgt tcctaagccg caccacctac agcctgcagg agcttggtgc     2160
catgggcatg ggagacctgc tcagtgccat gttcgacttc agcgagaagc tcaactccct     2220
ggcgcttacc gaggaggagc tgggcctctt caccgcggtg gtgcttgtct ctgcagaccg     2280
ctcgggcatg gagaattccg cttcggtgga gcagctccag gagacgctgc tgcgggctct     2340
tcgggctctg gtgctgaaga accggccctt ggagacttcc cgcttcacca agctgctgct     2400
caagctgccg gacctgcgga ccctgaacaa catgcattcc gagaagctgc tgtccttccg     2460
ggtggacgcc cagtgacccg cccggccggc cttctgccgc tgccccttg tacagaatcg     2520 aactctgcac ttctctctcc tttacgagac gaaaaggaaa agcaaaccag aatcttattt     2580
atattgttat aaaatattcc aagatgagcc tctggccccc tgagccttct tgtaaatacc     2640
tgcctccctc ccccatcacc gaacttcccc tcctcccta tttaaaccac tctgtctccc     2700
ccacaaccct cccctggccc tctgatttgt tctgttcctg tctcaaatcc aatagttcac     2760
```
agctgagctg gcttcaaaaa aaaaaaaaaa aaa                                  2793

<210> SEQ ID NO 4
<211> LENGTH: 614
<212> TYPE: PRT
<213> ORGANISM: Homo sapiens

<400> SEQUENCE: 4

Met Thr Thr Leu Asp Ser Asn Asn Thr Gly Gly Val Ile Thr Tyr
1               5                   10                  15

Ile Gly Ser Ser Gly Ser Ser Pro Ser Arg Thr Ser Pro Glu Ser Leu
                20                  25                  30

Tyr Ser Asp Asn Ser Asn Gly Ser Phe Gln Ser Leu Thr Gln Gly Cys
            35                  40                  45

Pro Thr Tyr Phe Pro Pro Ser Pro Thr Gly Ser Leu Thr Gln Asp Pro
    50                  55                  60

Ala Arg Ser Phe Gly Ser Ile Pro Pro Ser Leu Ser Asp Asp Gly Ser
65                  70                  75                  80

Pro Ser Ser Ser Ser Ser Ser Ser Ser Ser Ser Ser Phe Tyr Asn
                85                  90                  95

Gly Ser Pro Pro Gly Ser Leu Gln Val Ala Met Glu Asp Ser Ser Arg
                100                 105                 110

Val Ser Pro Ser Lys Ser Thr Ser Asn Ile Thr Lys Leu Asn Gly Met
            115                 120                 125

Val Leu Leu Cys Lys Val Cys Gly Asp Val Ala Ser Gly Phe His Tyr
    130                 135                 140

Gly Val His Ala Cys Glu Gly Cys Lys Gly Phe Phe Arg Arg Ser Ile
145                 150                 155                 160

Gln Gln Asn Ile Gln Tyr Lys Arg Cys Leu Lys Asn Glu Asn Cys Ser
                165                 170                 175

Ile Val Arg Ile Asn Arg Asn Arg Cys Gln Gln Cys Arg Phe Lys Lys
            180                 185                 190

Cys Leu Ser Val Gly Met Ser Arg Asp Ala Val Arg Phe Gly Arg Ile
    195                 200                 205

Pro Lys Arg Glu Lys Gln Arg Met Leu Ala Glu Met Gln Ser Ala Met
210                 215                 220

Asn Leu Ala Asn Asn Gln Leu Ser Ser Gln Cys Pro Leu Glu Thr Ser
225                 230                 235                 240

Pro Thr Gln His Pro Thr Pro Gly Pro Met Gly Pro Ser Pro Pro Pro
                245                 250                 255

Ala Pro Val Pro Ser Pro Leu Val Gly Phe Ser Gln Phe Pro Gln Gln
            260                 265                 270

Leu Thr Pro Pro Arg Ser Pro Ser Pro Glu Pro Thr Val Glu Asp Val
    275                 280                 285

Ile Ser Gln Val Ala Arg Ala His Arg Glu Ile Phe Thr Tyr Ala His
290                 295                 300

Asp Lys Leu Gly Ser Ser Pro Gly Asn Phe Asn Ala Asn His Ala Ser
305                 310                 315                 320

Gly Ser Pro Pro Ala Thr Thr Pro His Arg Trp Glu Asn Gln Gly Cys
                325                 330                 335

Pro Pro Ala Pro Asn Asp Asn Asn Thr Leu Ala Ala Gln Arg His Asn
            340                 345                 350

Glu Ala Leu Asn Gly Leu Arg Gln Ala Pro Ser Ser Tyr Pro Pro Thr
    355                 360                 365

Trp Pro Pro Gly Pro Ala His His Ser Cys His Gln Ser Asn Ser Asn
    370                 375                 380

Gly His Arg Leu Cys Pro Thr His Val Tyr Ala Ala Pro Glu Gly Lys
385                 390                 395                 400

Ala Pro Ala Asn Ser Pro Arg Gln Gly Asn Ser Lys Asn Val Leu Leu
                405                 410                 415

Ala Cys Pro Met Asn Met Tyr Pro His Gly Arg Ser Gly Arg Thr Val
            420                 425                 430

Gln Glu Ile Trp Glu Asp Phe Ser Met Ser Phe Thr Pro Ala Val Arg
        435                 440                 445

Glu Val Val Glu Phe Ala Lys His Ile Pro Gly Phe Arg Asp Leu Ser
    450                 455                 460

Gln His Asp Gln Val Thr Leu Leu Lys Ala Gly Thr Phe Glu Val Leu
465                 470                 475                 480

Met Val Arg Phe Ala Ser Leu Phe Asn Val Lys Asp Gln Thr Val Met
            485                 490                 495

Phe Leu Ser Arg Thr Thr Tyr Ser Leu Gln Glu Leu Gly Ala Met Gly
        500                 505                 510

Met Gly Asp Leu Leu Ser Ala Met Phe Asp Phe Ser Glu Lys Leu Asn
    515                 520                 525

Ser Leu Ala Leu Thr Glu Glu Leu Gly Leu Phe Thr Ala Val Val
530                 535                 540

Leu Val Ser Ala Asp Arg Ser Gly Met Glu Asn Ser Ala Ser Val Glu
545                 550                 555                 560

Gln Leu Gln Glu Thr Leu Leu Arg Ala Leu Arg Ala Leu Val Leu Lys
            565                 570                 575

Asn Arg Pro Leu Glu Thr Ser Arg Phe Thr Lys Leu Leu Leu Lys Leu
        580                 585                 590

Pro Asp Leu Arg Thr Leu Asn Asn Met His Ser Glu Lys Leu Leu Ser
    595                 600                 605

Phe Arg Val Asp Ala Gln
610

<210> SEQ ID NO 5
<211> LENGTH: 1740
<212> TYPE: DNA
<213> ORGANISM: Homo sapiens
<220> FEATURE:
<221> NAME/KEY: misc_feature
<222> LOCATION: (994)..(994)
<223> OTHER INFORMATION: n is a, c, g, or t

<400> SEQUENCE: 5
atggaggtga atgcaggagg tgtgattgcc tatatcagtt cttccagctc agcctcaagc        60
cctgcctctt gtcacagtga gggttctgag aatagtttcc agtcctcctc ctcttctgtt       120
ccatcttctc caaatagctc taattctgat accaatggta atcccaagaa tggtgatctc       180
gccaatattg aaggcatctt gaagaatgat cgaatagatt gttctatgaa acaagcaaa        240 tcgagtgcac ctgggatgac aaaaaatcat agtggtgtga caaaatttag tggcatggtt       300
ctactgtgta agtctgtgg ggatgtgcg tcaggattcc actatggagt tcatgcttgc         360
gaaggctgta agggtttctt tcggagaagt attcaacaaa acatccagta caagaagtgc       420
ctgaagaatg aaaactgttc tataatgaga atgaatagga acagatgtca gcaatgtcgc       480
ttcaaaaagt gtctgtctgt tggaatgtca agagatgctg ttcggtttgg tcgtattcct       540

```
aagcgtgaaa aacagaggat gctaattgaa atgcaaagtg caatgaagac catgatgaac    600
agccagttca gtggtcactt gcaaaatgac acattagtag aacatcatga acagacagcc    660
ttgccagccc aggaacagct gcgacccaag ccccaactgg agcaagaaaa catcaaaagc    720
tcttctcctc catcttctga ttttgcaaag gaagaagtga ttggcatggt gaccagagct    780
cacaaggata cctttatgta taatcaagag cagcaagaaa actcagctga gagcatgcag    840
ccccagagag gagaacggat tcccaagaac atggagcaat ataatttaaa tcatgatcat    900
tgcggcaatg ggcttagcag ccattttccc tgtagtgaga gccagcagca tctcaatgga    960
cagttcaaag ggaggaatat aatgcattac ccanatggcc atgccatttg tattgcaaat   1020
ggacattgta tgaacttctc caatgcttat actcaaagag tatgtgatag agttccgata   1080
gatggatttt ctcagaatga gaacaagaat agttacctgt gcaacactgg aggaagaatg   1140
catctggttt gtccaatgag taagtctcca tatgtggatc ctcataaatc aggacatgaa   1200
atctgggaag aattttcgat gagcttcact ccagcagtga agaagtggt ggaatttgca    1260 aagcgtattc ctgggttcag agatctctct cagcatgacc aggtcaacct tttaaaggct   1320 gggactttg aggttttaat ggtacggttc gcatcattat ttgatgcaaa ggaacgtact    1380 gtcaccttt taagtggaaa gaaatatagt gtggatgatt tacactcaat gggagcaggg    1440
gatctgctaa actctatgtt tgaatttagt gagaagctaa atgccctcca acttagtgat   1500
gaagagatga gtttgtttac agctgttgtc ctggtatctg cagatcgatc tggaatagaa   1560
aacgtcaact ctgtggaggc tttgcaggaa actctcattc gtgcactaag gaccttaata   1620
atgaaaaacc atccaaatga ggcctctatt tttacaaaac tgcttctaaa gttgccagat   1680
cttcgatctt taaacaacat gcactctgag gagctcttgg cctttaaagt tcacccttaa   1740
```

<210> SEQ ID NO 6
<211> LENGTH: 578
<212> TYPE: PRT
<213> ORGANISM: Homo sapiens
<220> FEATURE:
<221> NAME/KEY: misc_feature
<222> LOCATION: (332)..(332)
<223> OTHER INFORMATION: Xaa can be any naturally occurring amino acid
<400> SEQUENCE: 6

```
Met Glu Val Asn Ala Gly Gly Val Ile Ala Tyr Ile Ser Ser Ser Ser
1               5                   10                  15

Ser Ala Ser Ser Pro Ala Ser Cys His Ser Glu Gly Ser Glu Asn Ser
            20                  25                  30

Phe Gln Ser Ser Ser Ser Val Pro Ser Ser Pro Asn Ser Ser Asn
        35                  40                  45

Ser Asp Thr Asn Gly Asn Pro Lys Asn Gly Asp Leu Ala Asn Ile Glu
    50                  55                  60

Gly Ile Leu Lys Asn Asp Arg Ile Asp Cys Ser Met Lys Thr Ser Lys
65                  70                  75                  80

Ser Ser Ala Pro Gly Met Thr Lys Asn His Ser Gly Val Thr Lys Phe
                85                  90                  95

Ser Gly Met Val Leu Leu Cys Lys Val Cys Gly Asp Val Ala Ser Gly
            100                 105                 110

Phe His Tyr Gly Val His Ala Cys Glu Gly Cys Lys Gly Phe Phe Arg
        115                 120                 125

Arg Ser Ile Gln Gln Asn Ile Gln Tyr Lys Lys Cys Leu Lys Asn Glu
    130                 135                 140
```

```
Asn Cys Ser Ile Met Arg Met Asn Arg Asn Arg Cys Gln Gln Cys Arg
145                 150                 155                 160

Phe Lys Lys Cys Leu Ser Val Gly Met Ser Arg Asp Ala Val Arg Phe
            165                 170                 175

Gly Arg Ile Pro Lys Arg Glu Lys Gln Arg Met Leu Ile Glu Met Gln
            180                 185                 190

Ser Ala Met Lys Thr Met Met Asn Ser Gln Phe Ser Gly His Leu Gln
            195                 200                 205

Asn Asp Thr Leu Val Glu His His Glu Gln Thr Ala Leu Pro Ala Gln
210                 215                 220

Glu Gln Leu Arg Pro Lys Pro Gln Leu Glu Gln Glu Asn Ile Lys Ser
225                 230                 235                 240

Ser Ser Pro Pro Ser Ser Asp Phe Ala Lys Glu Val Ile Gly Met
            245                 250                 255

Val Thr Arg Ala His Lys Asp Thr Phe Met Tyr Asn Gln Glu Gln Gln
            260                 265                 270

Glu Asn Ser Ala Glu Ser Met Gln Pro Gln Arg Gly Glu Arg Ile Pro
            275                 280                 285

Lys Asn Met Glu Gln Tyr Asn Leu Asn His Asp His Cys Gly Asn Gly
            290                 295                 300

Leu Ser Ser His Phe Pro Cys Ser Glu Ser Gln Gln His Leu Asn Gly
305                 310                 315                 320

Gln Phe Lys Gly Arg Asn Ile Met His Tyr Pro Xaa Gly His Ala Ile
            325                 330                 335

Cys Ile Ala Asn Gly His Cys Met Asn Phe Ser Asn Ala Tyr Thr Gln
            340                 345                 350

Arg Val Cys Asp Arg Val Pro Ile Asp Gly Phe Ser Gln Asn Glu Asn
            355                 360                 365

Lys Asn Ser Tyr Leu Cys Asn Thr Gly Gly Arg Met His Leu Val Cys
            370                 375                 380

Pro Met Ser Lys Ser Pro Tyr Val Asp Pro His Lys Ser Gly His Glu
385                 390                 395                 400

Ile Trp Glu Glu Phe Ser Met Ser Phe Thr Pro Ala Val Lys Glu Val
            405                 410                 415

Val Glu Phe Ala Lys Arg Ile Pro Gly Phe Arg Asp Leu Ser Gln His
            420                 425                 430

Asp Gln Val Asn Leu Leu Lys Ala Gly Thr Phe Glu Val Leu Met Val
            435                 440                 445

Arg Phe Ala Ser Leu Phe Asp Ala Lys Glu Arg Thr Val Thr Phe Leu
450                 455                 460

Ser Gly Lys Lys Tyr Ser Val Asp Asp Leu His Ser Met Gly Ala Gly
465                 470                 475                 480

Asp Leu Leu Asn Ser Met Phe Glu Phe Ser Glu Lys Leu Asn Ala Leu
            485                 490                 495

Gln Leu Ser Asp Glu Glu Met Ser Leu Phe Thr Ala Val Val Leu Val
            500                 505                 510

Ser Ala Asp Arg Ser Gly Ile Glu Asn Val Asn Ser Val Glu Ala Leu
            515                 520                 525

Gln Glu Thr Leu Ile Arg Ala Leu Arg Thr Leu Ile Met Lys Asn His
            530                 535                 540

Pro Asn Glu Ala Ser Ile Phe Thr Lys Leu Leu Leu Lys Leu Pro Asp
545                 550                 555                 560

Leu Arg Ser Leu Asn Asn Met His Ser Glu Glu Leu Leu Ala Phe Lys
```

```
              565                 570                 575
Val His

<210> SEQ ID NO 7
<211> LENGTH: 2058
<212> TYPE: DNA
<213> ORGANISM: Homo sapiens

<400> SEQUENCE: 7
atggcggcag cgtcccggag cgcctctggc tgggcgctac tgctgctggt ggcactttgg      60
cagcagcgcg cggccggctc cggcgtcttc cagctgcagc tgcaggagtt catcaacgag     120
cgcggcgtac tggccagtgg gcggccttgc gagcccggct gccggacttt cttccgcgtc     180
tgccttaagc acttccaggc ggtcgtctcg cccggaccct gccttcgg gaccgtctcc       240 acgccggtat tgggcaccaa ctccttcgct gtccgggacg acagtagcgg cgggggggcgc    300 aaccctctcc aactgccctt caatttcacc tggccgggta ccttctcgct catcatcgaa     360
gcttggcacg cgccaggaga cgacctgcgg ccagaggcct gccaccaga tgcactcatc      420 agcaagatcg ccatccaggg ctccctagct gtgggtcaga actggttatt ggatgagcaa     480
accagcaccc tcacaaggct gcgctactct taccgggtca tctgcagtga caactactat     540
ggagacaact gctcccgcct gtgcaagaag cgcaatgacc acttcggcca ctatgtgtgc    600
cagccagatg gcaacttgtc ctgcctgccc ggttggactg ggaatattg ccaacagcct      660 atctgtcttt cgggctgtca tgaacagaat ggctactgca gcaagccagc agagtgcctc     720
tgccgcccag gctggcaggg ccggctgtgt aacgaatgca tcccccacaa tggctgtcgc    780
cacggcacct gcagcactcc ctggcaatgt acttgtgatg agggctgggg aggcctgttt    840
tgtgaccaag atctcaacta ctgcacccac cactccccat gcaagaatgg ggcaacgtgc    900
tccaacagtg ggcagcgaag ctacacctgc acctgtcgcc caggctacac tggtgtggac    960
tgtgagctgg agctcagcga gtgtgacagc aaccccgtc gcaatggagg cagctgtaag    1020
gaccaggagg atggctacca ctgcctgtgt cctccgggct actatggcct gcattgtgaa    1080
cacagcacct tgagctgcgc cgactccccc tgcttcaatg gggctcctg ccgggagcgc    1140 aaccaggggg ccaactatgc ttgtgaatgt cccccaact tcaccggctc caactgcgag    1200
aagaaagtgg acaggtgcac cagcaacccc tgtgccaacg ggacagtg cctgaaccga    1260 ggtccaagcc gcatgtgccg ctgccgtcct ggattcacgg gcacctactg tgaactccac    1320
gtcagcgact gtgcccgtaa cccttgcgcc cacggtggca cttgccatga cctggagaat    1380
gggctcatgt gcacctgccc tgccggcttc tctggccgac gctgtgaggt gcggacatcc    1440
atcgatgcct gtgcctcgag tccctgcttc aacagggcca cctgctacac cgacctctcc    1500
acagacacct ttgtgtgcaa ctgcccttat ggctttgtgg cagccgctg cgagttcccc    1560 gtgggcttgc cgcccagctt ccctgggtg gccgtctcgc tgggtgtggg gctggcagtg    1620
ctgctggtac tgctgggcat ggtggcagtg gctgtgcggc agctgcggct tcgacggccg    1680
gacgacggca gcagggaagc catgaacaac ttgtcggact tccagaagga caacctgatt    1740
cctgccgccc agcttaaaaa acaaaaccag aagaaggagc tggaagtgga ctgtggcctg    1800
gacaagtcca actgtggcaa acagcaaaac cacacattgg actataatct ggccccaggg    1860 ccctggggc gggggaccat gccaggaaag tttccccaca gtgacaagag cttaggagag    1920
aaggcgccac tgcggttaca cagtgaaaag ccagagtgtc ggatatcagc gatatgctcc    1980 cccaggagact ccatgtacca gtctgtgtgt ttgatatcag aggagaggaa tgaatgtgtc    2040
```
attgccacgg aggtataa                                                         2058

<210> SEQ ID NO 8
<211> LENGTH: 685
<212> TYPE: PRT
<213> ORGANISM: Homo sapiens

<400> SEQUENCE: 8

```
Met Ala Ala Ser Arg Ser Ala Ser Gly Trp Ala Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
                35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
        355                 360                 365
```

```
Ser Pro Cys Phe Asn Gly Gly Ser Cys Arg Glu Arg Asn Gln Gly Ala
    370                 375                 380

Asn Tyr Ala Cys Glu Cys Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
                420                 425                 430

Thr Gly Thr Tyr Cys Glu Leu His Val Ser Asp Cys Ala Arg Asn Pro
                435                 440                 445

Cys Ala His Gly Gly Thr Cys His Asp Leu Glu Asn Gly Leu Met Cys
        450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
                500                 505                 510

Val Gly Ser Arg Cys Glu Phe Pro Val Gly Leu Pro Pro Ser Phe Pro
                515                 520                 525

Trp Val Ala Val Ser Leu Gly Val Gly Leu Ala Val Leu Leu Val Leu
            530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
    595                 600                 605

Gln Asn His Thr Leu Asp Tyr Asn Leu Ala Pro Gly Pro Leu Gly Arg
    610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
                660                 665                 670

Ser Glu Glu Arg Asn Glu Cys Val Ile Ala Thr Glu Val
        675                 680                 685

<210> SEQ ID NO 9
<211> LENGTH: 426
<212> TYPE: DNA
<213> ORGANISM: Homo sapiens

<400> SEQUENCE: 9
atgtcaaaca tgagatgtgt ggactgtggc acttgcctgg gtcacacacg gaggcatcct    60
acccttttct ggggaaagac actgcctggg ctgaccccgg tgcggcccc agcacctcag   120 cctgcacagt gtcccccagg ttccgaagaa gatgctccag caacacagcc tgggcccag   180
```

```
ctcgcgggac ccgacccccc gtgggctccc gtgttttgta ggagacttgc cagagccggg    240
cacattgagc tgtgcaacgc cgtgggctgc gtcctttggt cctgtccccg cagccctggc    300 aggggcatg  cggtcgggca ggggctggag ggaggcgggg gctgcccttg ggccacccct    360
cctagtttgg gaggagcaga tttttgcaat accaagtata gcctatggca gaaaaaatgt    420
ctttaa                                                               426
```

<210> SEQ ID NO 10
<211> LENGTH: 141
<212> TYPE: PRT
<213> ORGANISM: Homo sapiens

<400> SEQUENCE: 10

```
Met Ser Asn Met Arg Cys Val Asp Cys Gly Thr Cys Leu Gly His Thr
1               5                   10                  15

Arg Arg His Pro Thr Leu Phe Trp Gly Lys Thr Leu Pro Gly Leu Thr
            20                  25                  30

Pro Val Ala Ala Pro Ala Pro Gln Pro Ala Gln Cys Pro Pro Gly Ser
        35                  40                  45

Glu Glu Asp Ala Pro Ala Thr Gln Pro Gly Pro Gln Leu Ala Gly Pro
    50                  55                  60

Asp Pro Pro Trp Ala Pro Val Phe Cys Arg Arg Leu Ala Arg Ala Gly
65                  70                  75                  80

His Ile Glu Leu Cys Asn Ala Val Gly Cys Val Leu Trp Ser Cys Pro
                85                  90                  95

Arg Ser Pro Gly Arg Gly His Ala Val Gly Gln Gly Leu Glu Gly Gly
            100                 105                 110

Gly Gly Cys Pro Trp Ala Thr Pro Pro Ser Leu Gly Gly Ala Asp Phe
        115                 120                 125

Cys Asn Thr Lys Tyr Ser Leu Trp Gln Lys Lys Cys Leu
    130                 135                 140
```

NATURAL KILLER CELLS

FIELD OF THE INVENTION

This invention relates to expanded Natural Killer (NK) cell populations, to methods of producing the same and therapeutic applications thereof. More specifically, the invention relates to the expansion of NK cells by increasing the expression of specific transcription factors associated with NK cell production.

BACKGROUND OF THE INVENTION

There has been an increase in interest in Natural Killer (NK) cells as they are cytotoxic against cancerous, pathogen-infected and otherwise damaged cells. NK cells are innate lymphoid cells (ILCs), specifically large granular cytotoxic lymphocytes that bridge the innate and the adaptive arms of the immune response. They make up 10-15% of circulating lymphocytes in the peripheral blood. NK cells also exhibit the highest level of cytotoxic activity within the immune system. Therefore, altered NK cell functionality or numbers impact the functioning of the immune system against infection and cancer. For example, a large scale study in Japan has shown that reduced levels of NK cells in a cohort of people aged over 40 is associated with a significantly higher incidence of cancer.

Similarly to B cells and T cells, these NK cells are derived from Common Lymphoid Progenitor (CLP) cells that in turn come from Haematopoietic Stem Cells (HSCs). However, NK cells are different from B and T cells as they lack specific cell surface antigen receptors. Due to this, NK cells may kill cancerous and pathogen-infected cells without prior sensitisation, making them part of the innate immune response. They also have a critical role in tumour immunosurveillance by directly influencing the adaptive immune response.

Activation of NK cells triggers them to release perforin and cytoplasmic granules containing granzymes. Perforin polymerises to form pores on target cells in the presence of $Ca2+$. Granzymes may enter these pores into target cells, causing DNA fragmentation and apoptosis. NK cells may also secrete cytokines, which trigger the action of other immune cells in the adaptive arm of the immunity.

Due to the importance of NK cells in immune response against pathogen infection and cancer cells, multiple clinical trials have tested the efficacy of NK cells in adoptive transfer protocols. In adoptive transfer, NK cells isolated from the blood of donors are expanded ex vivo and matured into healthy and functional NK cells prior to transfusion into recipients. However, to be effective it is crucial that NK cell donors are be screened for their KIR genotype, where the donor must have the appropriate KIR allelic polymorphism to the recipient to allow recognition of target cells for destruction. In any event, studies have found that the expanded products have lower clinical success rate than expected, with less ability to kill cancerous or infected cells. Thus, there are significant barriers to the current adoptive transfer protocols.

An alternative therapeutic approach is to increase the number of endogenous NK cells. One method is the administration of cytokines that are essential for NK cell development. Administration of IL-2 and IL-15 was predicted to enhance NK cell development. IL-2 promotes the proliferation and cytotoxicity of NK cells, whereas IL-15 promotes the development and expansion of NK cells. However, in in vivo studies, the cytokines were found only stimulate a minimal expansion of NK cells with reduced half-life, even at a very high dose. Further, administered cytokines often leads to systemic toxicity due to inappropriate activation of immune responses and the induction of NK cell apoptosis.

Thus, using conventional methods and techniques, producing large numbers of NK cells is difficult, and producing fully functional NK cells with high cytotoxicity is even harder. There is currently no drug available that selectively increases NK cell numbers. Therefore, there is a need to develop new methods of NK cell production; both ex vivo to produce large numbers of functional NK cells for therapeutic and research use; and in vivo.

SUMMARY OF THE INVENTION

Natural Killer (NK) cells have a critical role in the immune system where they destroy cancerous, pathogen-infected or damaged cells. Boosting NK cell number or functionality is predicted to increase the killing of these cells. Existing therapies such as NK cell adoptive transfer and cytokine enhancement of endogenous NK cells are not very successful in terms of their efficacy.

NK cells are differentiated from the HSCs in the bone marrow and distributed throughout lymphoid and non-lymphoid tissues including lymph nodes, spleen, peripheral blood, lungs and liver. Specific cytokines and transcription factors are needed to encourage HSCs to develop into NK cells. Each cytokine and transcription factor must be present at a precise time and concentration in order to push differentiation from HSCs into NK cells. However, the precise hierarchy of cytokines and transcription factors governing NK cell maturation is still incompletely understood.

In particular, the present inventors have focused on E4 binding protein 4 (E4bp4), which is also known as Nfil3. Upregulation of E4bp4 is a promising strategy to increase the production of NK cells as over expression of E4bp4 in HSCs greatly enhances in vitro NK cell production. However, transcription factors can be hard to drug because of their structure and function. For example, they usually lack enzymatic activity or cofactor binding sites. The present inventors have previously shown that inhibiting the action of REV-ERB increases NK cell production. In particular, the inventors demonstrated that inhibiting the action of REV-ERB using the REV-ERB antagonist SR8278 increases E4bp4 expression, which in turn increases NK cell production. Many synthetic ligands for REV-ERB have been generated in the art. However, on screening the vast majority of these ligands have been identified as agonists (with over 300 identified). The pharmacological profile of antagonist ligand SR8278 is such that it is not suitable for use in a clinical setting. Furthermore, the lack of information on the mechanism of action of SR8278 and the lack of suitable structure-activity relationships surrounding this molecule has hindered the discovery of other antagonistic compounds.

The present inventors have now generated a library of compounds, and have demonstrated that several such compounds possess improved REV-ERB inhibitory activity compared with SR8278. These compounds therefore have potential to improve the ex vivo expansion of NK cells, as well as to provide improved pharmacological properties, making them more appropriate for use in clinical applications. The compounds may also exhibit favourable pharmacological properties, such as good metabolic stability and low toxicity.

Accordingly, the present invention provides an ex vivo method for expanding an NK cell population, comprising the steps of:

a) culturing an haematopoietic progenitor cell (HPC) comprising sample obtained from an individual;
b) contacting said sample with a compound that inhibits the action of REV-ERB; and c) expanding said cells in vitro to produce an NK cell population;
wherein the compound has formula (I):

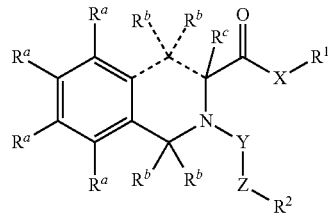

(I)

where: ------ represents bonds that are all either present or absent;
R¹ is selected from $C_{1-6}$ hydrocarbyl, and is optionally substituted with one or more groups independently selected from $C_{1-4}$ hydrocarbyl, —OR', —OC(O)R', —C(O)OR', —SR', —S(O)R', —S(O)$_2$R', —NR'$_2$, —NR'C(O)R', —C(O)NR'$_2$, —CN, —NO$_2$, -Ph, —CF$_3$ and halogen;
R² is selected from 5-10 membered heterocyclyl rings and $C_{1-6}$ hydrocarbyl, and is optionally substituted with one or more groups independently selected from $C_{1-4}$ hydrocarbyl, —OR', —OC(O)R', —C(O)OR', —SR', —S(O)R', —S(O)$_2$R', —NR'$_2$, —NR'C(O)R', —C(O)NR'$_2$, —CN, —NO$_2$, -Ph, —CF$_3$ and halogen;
X is selected from —O— and —NR'— or is absent;
Y is selected from —C(O)— or —CR'$_2$—;
Z is selected from —O— and —NR'— or is absent;
each $R^a$ is independently selected from H, $C_{1-4}$ hydrocarbyl, —OR', —OC(O)R', —C(O)OR', —SR', —S(O)R', —S(O)$_2$R', —NR'$_2$, —NR'C(O)R', —C(O)NR'$_2$, —CN, —NO$_2$, -Ph, —CF$_3$ and halogen;
each $R^b$ is independently selected from H, $C_{1-4}$ hydrocarbyl and —OR';
$R^c$ is selected from H and $C_{1-4}$ hydrocarbyl; and
each R' is independently selected from H, $C_{1-4}$ hydrocarbyl and -Ph;
or a pharmaceutically acceptable salt thereof, provided that the compound is not:

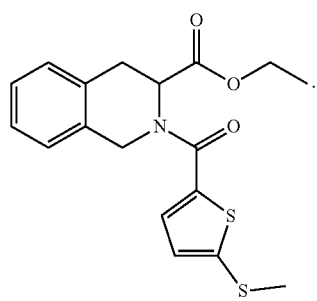 [SMILES: CCOC(=O)C1Cc2ccccc2CN1C(=O)c1ccc(SC)s1]

In some embodiments, ------ represents bonds that are all present and the compound is a closed ring structure according to formula Ia:

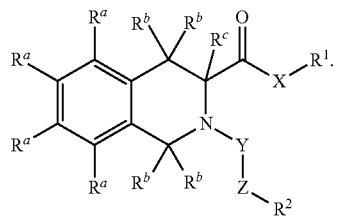

(Ia)

R¹ may be unsubstituted and, as such, is preferably selected from $C_{1-6}$ alkyl and $C_{1-6}$ alkenyl, more preferably, R¹ is selected from $C_{1-6}$ alkyl, even more preferably from $C_{1-4}$ alkyl, such as from methyl, ethyl and propyl.

R² may be selected from: (i) optionally substituted 5-10 membered heterocyclyl rings, preferably optionally substituted 5-10 membered heteroaryl rings, and the 5-10 membered heteroaryl ring is preferably an optionally substituted 5-, 6- or 9-membered heteroaryl rings, wherein optionally the 5-, 6-, or 9-membered heteroaryl ring is selected from optionally substituted: furanyl, thiophenyl, oxazolyl, isooxazolyl, isothiazolyl, thiazolyl, pyrazolyl, imidazolyl, pyrrolyl and triazolyl, pyridinyl, pyridazinyl, pyrimidinyl and pyrazinyl, indolyl, isoindolyl, indazolyl, benzimidazolyl, azaindolyl, benzofuranyl, isobenzofuranyl, benzisoxazolyl and benzoxazolyl; and (ii) optionally substituted phenyl, preferably substituted phenyl; and/or R² may be unsubstituted or substituted with one or two groups independently selected from $C_{1-4}$ alkyl, —OR', —OC(O)R', —C(O)OR', —SR', —S(O)R', —S(O)$_2$R', —NR'$_2$, —NR'C(O)R', —C(O)NR'$_2$, —CN, —NO$_2$, -Ph, —CF$_3$ and halogen, preferably R² is unsubstituted or substituted with one or two groups independently selected from -Me, —OMe, —CN, —NO$_2$, —F, —Cl, —I and —SMe.

X may be —O—; Y may be —C(O)—; Z may be —O— or is absent, preferably Z is absent; each $R^a$ may be independently selected from H, $C_{1-4}$ alkyl and —OR', preferably from H and $C_{1-4}$ alkyl, and more preferably, each $R^a$ is H; each $R^b$ may be independently selected from H and $C_{1-4}$ alkyl, preferably, each $R^b$ is H; $R^c$ may be H; and/or each R' may be independently selected from H and $C_{1-4}$ alkyl, preferably from H, methyl and ethyl, and more preferably from methyl and ethyl.

In some preferred embodiments $R^b$ and $R^c$ are all H, such that the compound has the formula (II):

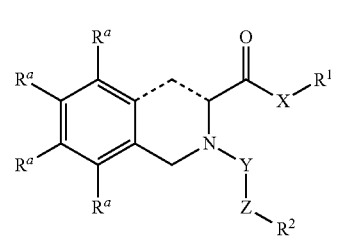

(II)

where R¹, R², $R^a$, X, Y and Z are defined herein.

In some preferred embodiments, $R^a$ are also all H, such that the compound has the formula (III):

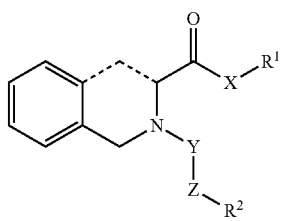

(III)

where R¹, R², X, Y and Z are defined herein;
preferably X is O, such that the compound has the formula (IV):

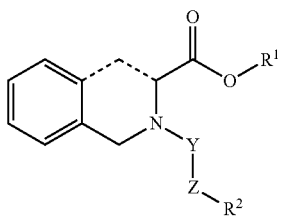

(IV)

where R¹, R², Y and Z are as defined herein;
more preferably, Y is C(O), such that the compound has the formula (V):

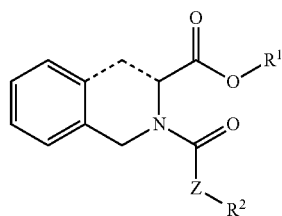

(V)

where R¹, R² and Z are as defined herein;
still more preferably, R¹ is ethyl, such that the compound has the formula (VI):

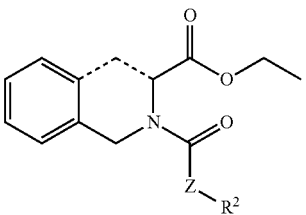

(VI)

where R² and Z are as defined herein;
yet still more preferably, the compound is a closed ring structure with the formula (VII):

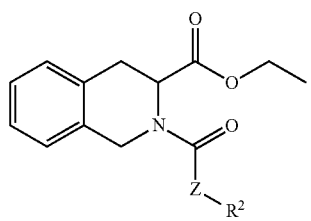

(VII)

where R² and Z are as defined herein.

In some embodiments of the method of the invention the compound has a formula selected from:

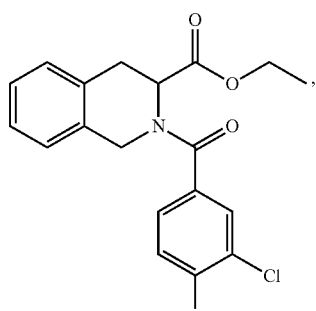

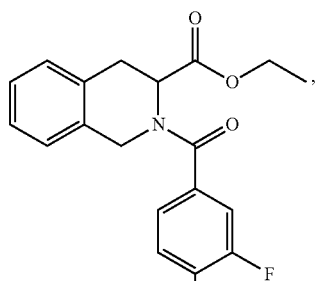

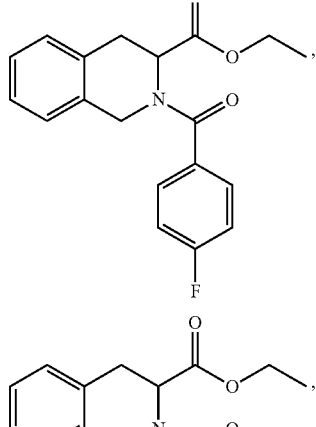

-continued
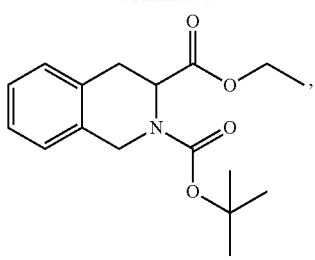
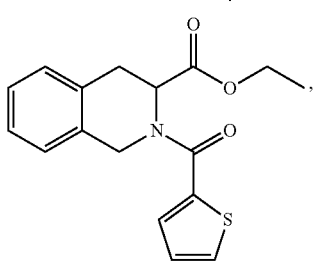
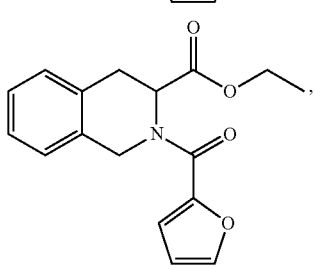
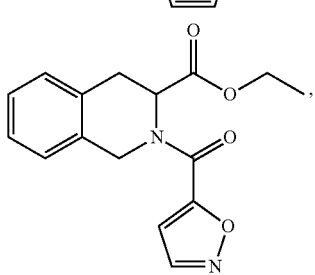
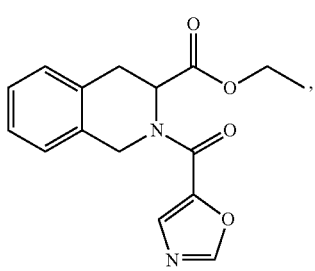
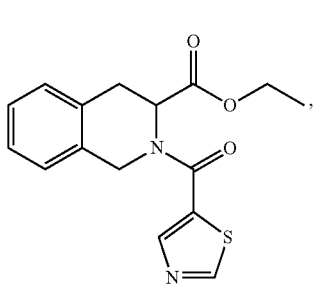
-continued
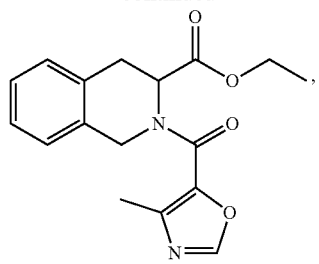
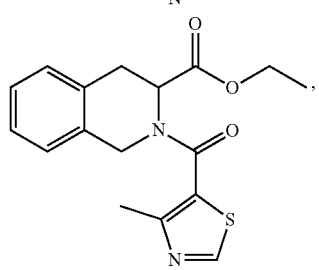
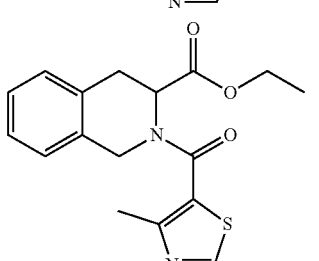
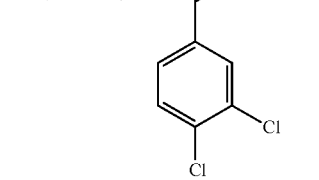
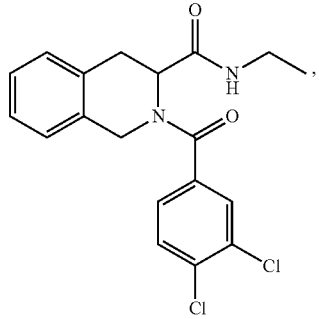

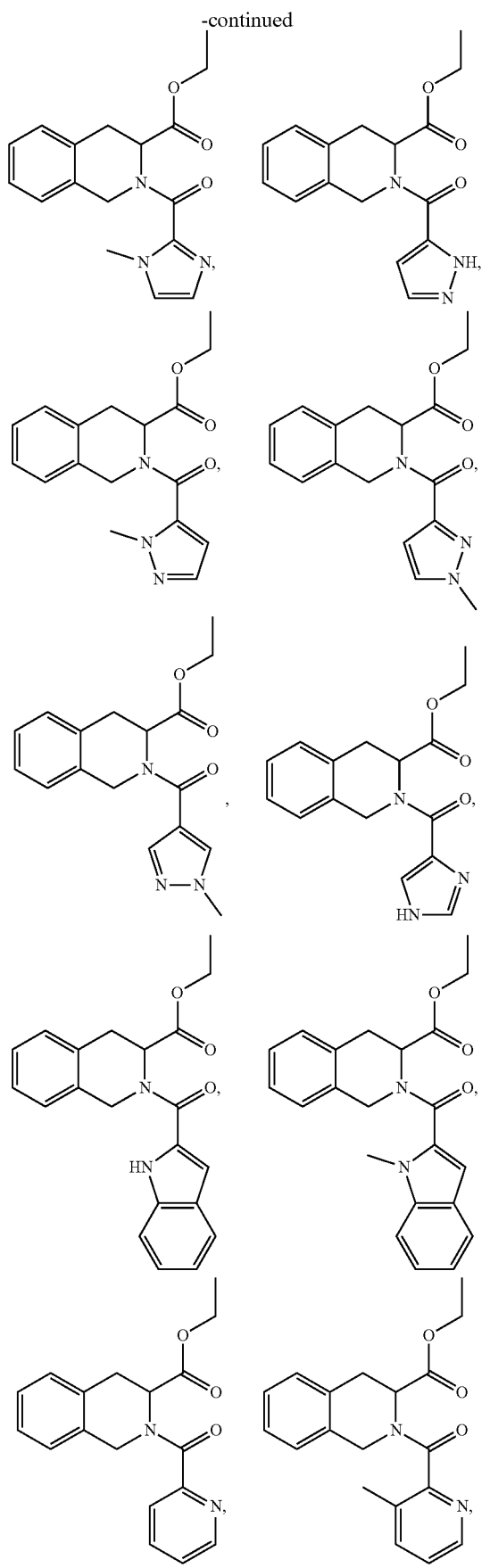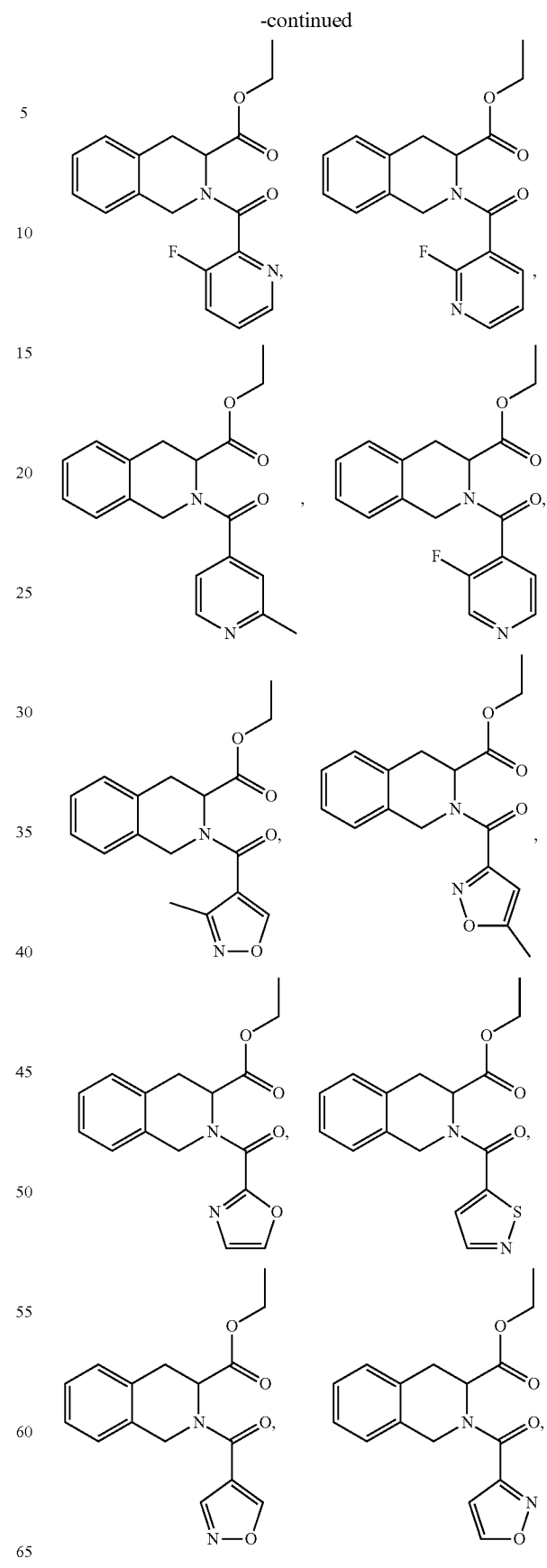

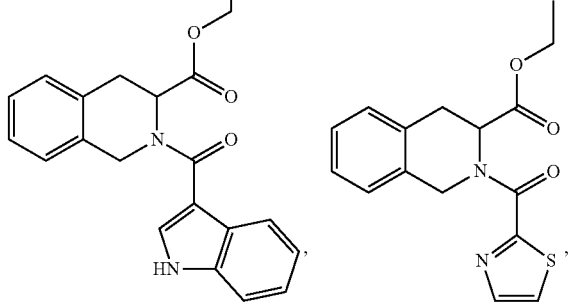
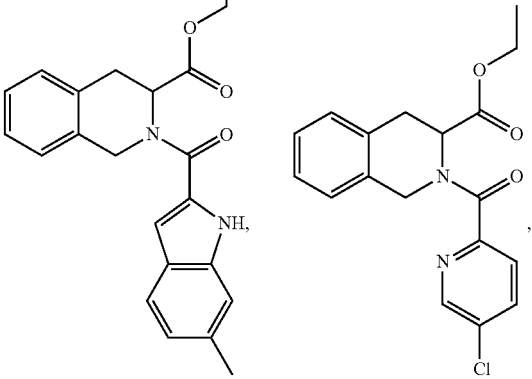
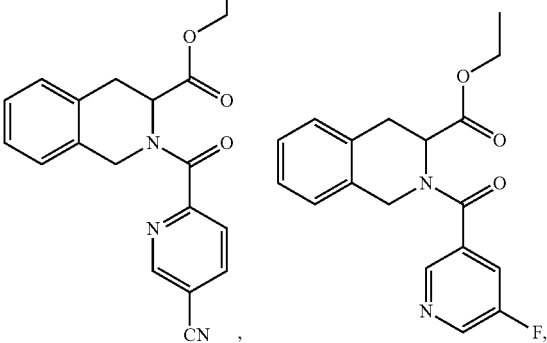
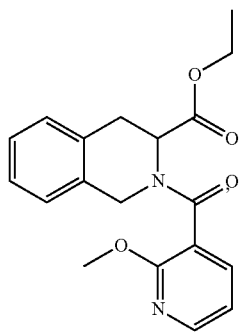
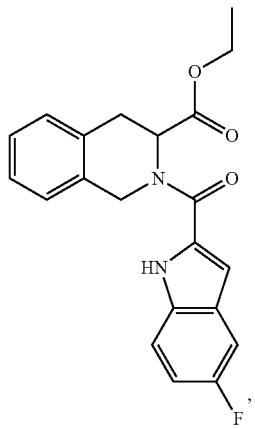

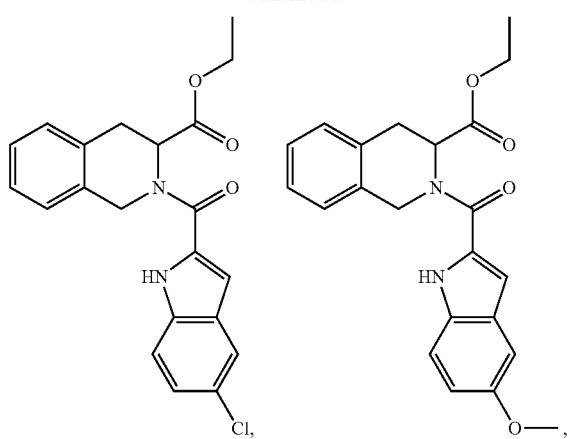
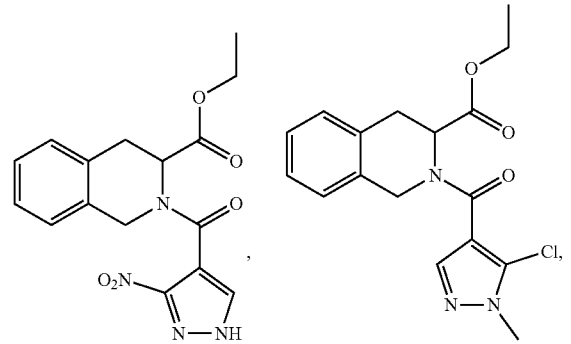
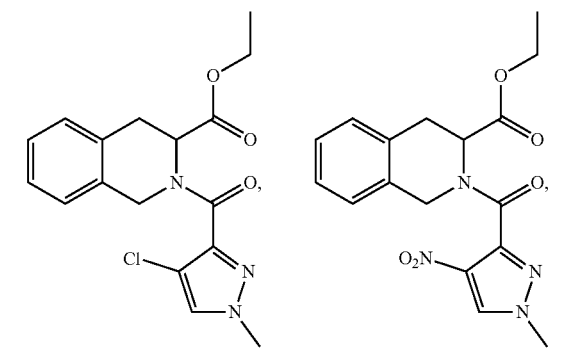
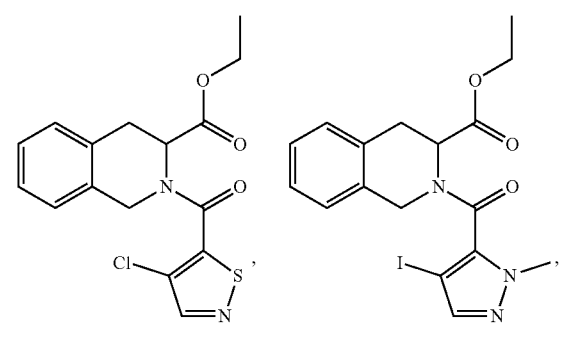
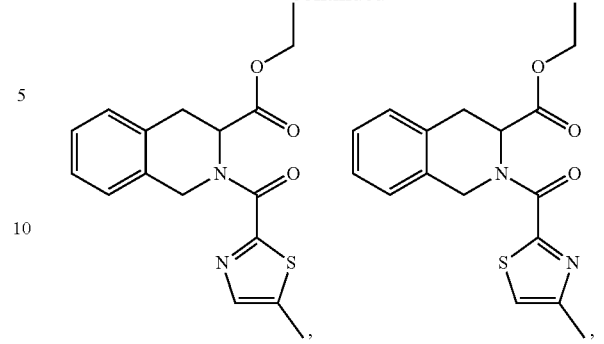
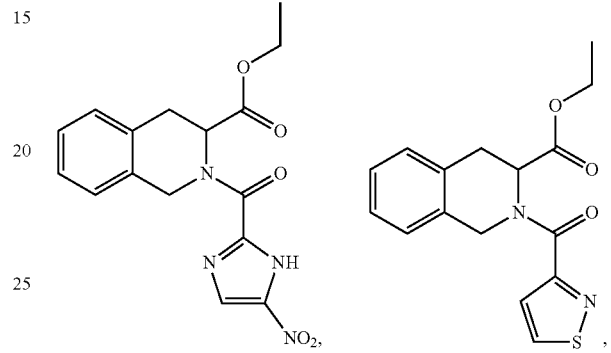
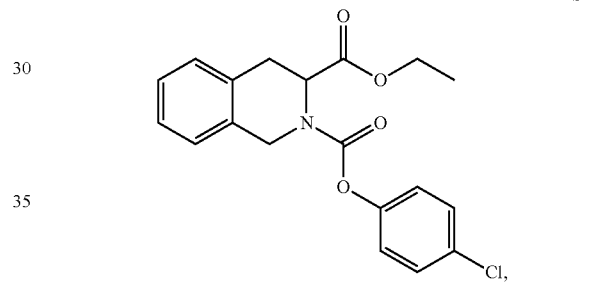
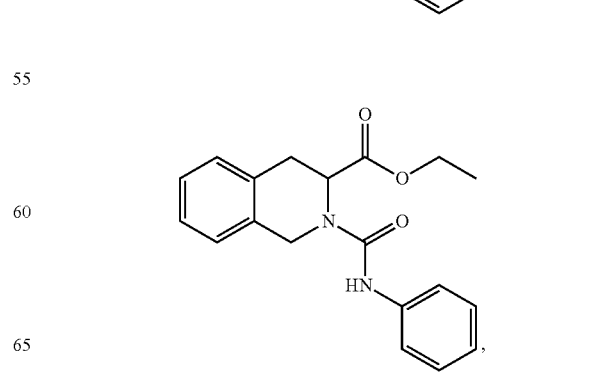

-continued
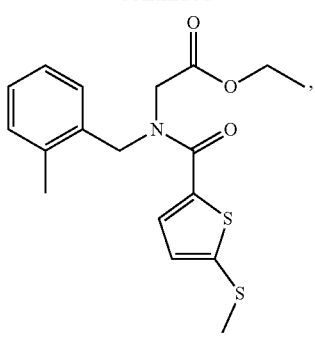
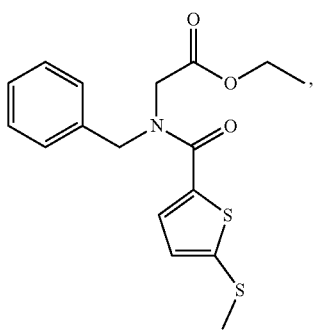
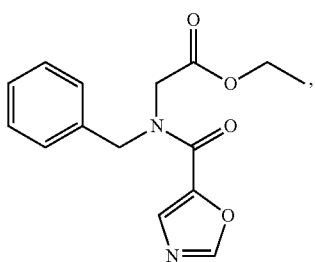
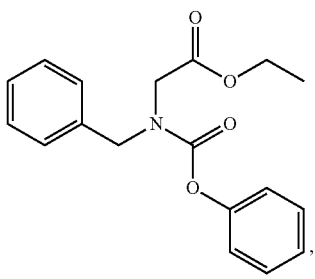
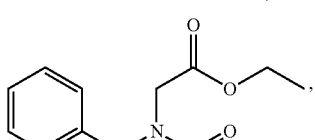
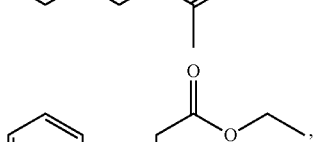
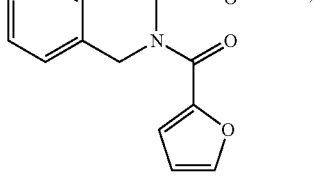
-continued
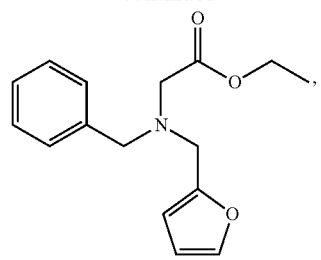
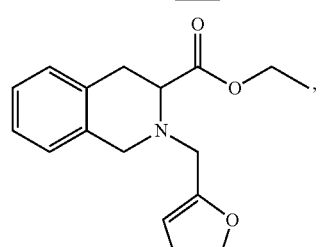
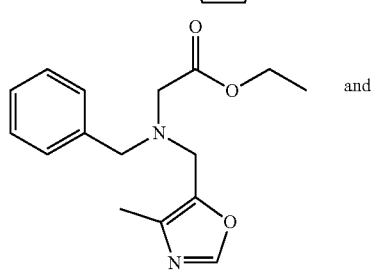
and
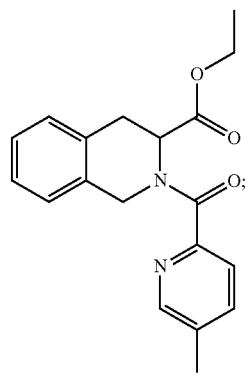
wherein preferably the compound has the formula:
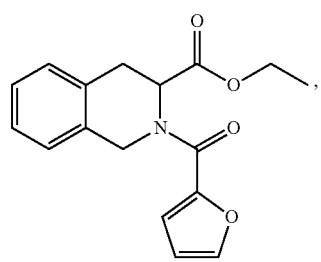

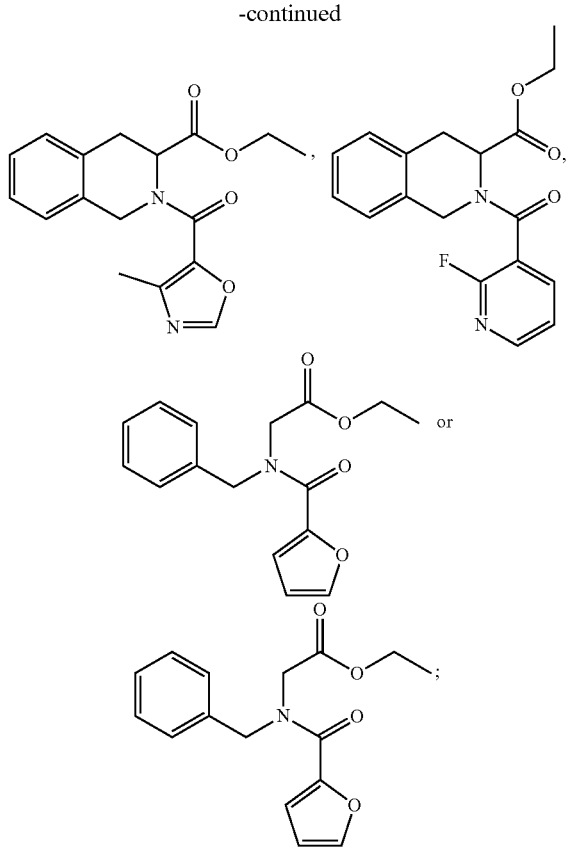

wherein more preferably the compound has the formula:

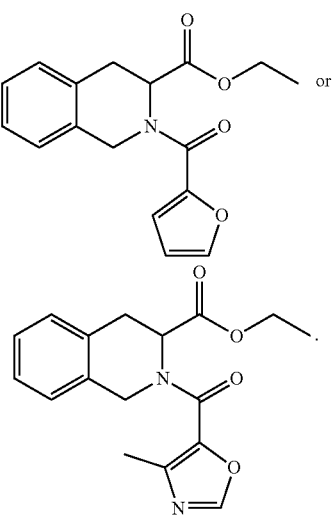

Typically said compound increases E4bp4 expression by decreasing REV-ERB activity. In some embodiments of the method of the invention, said compound decreases the activity of REV-ERB-α and/or REW-ERB-β, preferably REW-ERB-β, and more preferably REW-ERB-α and REW-ERB-β. In some preferred embodiments, said compound is a REV-ERB antagonist, preferably an antagonist of REV-ERB-α and REV-ERB-β.

According to the invention, said method may further comprise a step of culturing the HPCs in the presence of a Notch ligand, wherein optionally the vessel in which the HPCs are cultured is coated with the Notch ligand. In some embodiments (a) the Notch ligand is delta-like ligand 4 (DLL4), or a fragment thereof which retains the function of DLL4; and/or (b) the Notch ligand is present on or from 4 days after isolating said HPCs. The cells may be cultured in the presence of IL-15 after the step of culturing in the presence of the Notch ligand; and/or the HPCs may be cultured in the presence of the Notch ligand in combination with IL-7, Flt3L and/or stem cell factor (SCF), preferably the Notch ligand in combination with IL-7, Flt3L and SCF; wherein optionally either or both of the step of culturing in the cells in the presence of the Notch ligand and the step of culturing in the presence of IL-15 are carried out in the absence of a stromal support cell, and preferably wherein both steps are carried out in the absence of a stromal support cell.

According to the invention, the method may further comprise the step of contacting the HPCs with a compound which results in the alteration of post-translational modification of E4bp4, thereby causing an increase in E4bp4 activity; wherein optionally the alteration of post-translational modification of E4bp4 is a reduction in SUMOylation and/or phosphorylation of E4bp4, and preferably the compound which results in the alteration of post-translational modification of E4bp4: (a) reduces SUMOylation at one or more of residues K10, K116, K219, K337 and/or K394 of E4bp4, or a residue corresponding thereto, or any combination thereof; and/or (b) reduces phosphorylation at one or more of residues S286, S301 and/or S454 of E4bp4, or a residue corresponding thereto, or any combination thereof.

The sample of HPCs may be obtained from bone marrow, cord blood and/or peripheral blood.

The invention further provides an expanded NK cell population obtained by the method of the invention, wherein at least 85% of the NK cells are $CD56^+$ and $CD45^+$.

The invention further provides a composition comprising an expanded NK cell population of the invention and a pharmaceutically acceptable carrier, diluent and/or excipient.

Also provided by the invention is a compound which inhibits the action of REV-ERB activity for use in a method of therapy by increasing production of natural killer (NK) cells in a patient, wherein said compound is a compound of the invention as defined herein.

The invention further provides products containing a compound which inhibits the action of REV-ERB and a Notch ligand as a combined preparation for simultaneous, separate or sequential use in a method of therapy by increasing production of natural killer (NK) cells in a patient, wherein said compound is a compound of the invention, and optionally said Notch ligand is delta-like ligand 4 (DLL4), or a fragment thereof which retains the function of DLL4.

According to the invention, said method of therapy may be: (a) a method of treating a disease or disorder selected from cancer, an infectious disease (acute or chronic), an autoimmune disease or a disease or disorder related to female infertility or pregnancy; or (b) a method of treatment of a viral infection, a bacterial infection, a protest infection, a fungal infection and/or a helminth infection.

The invention further provides a method of treatment by increasing the number of NK cells in a patient in need thereof, comprising administering to said patient a therapeutically effective amount of a compound which inhibits the action of REV-ERB according to the invention, and optionally a Notch ligand, wherein preferably the Notch ligand is delta-like ligand 4 (DLL4), or a fragment thereof which retains the function of DLL4.

The compound or products for use of the invention, or the method of treatment of the invention may be used in combination with antibody-mediated immunotherapy, wherein optionally said compound or products is for administration before, simultaneously with, or after administration of the antibody-mediated immunotherapy.

The invention also provides a compound of formula (I) as defined herein, provided that the compound is not:

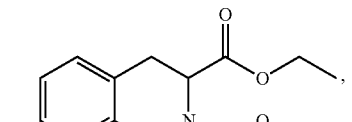

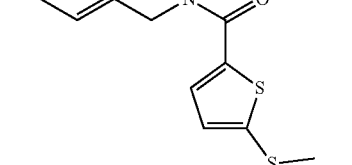

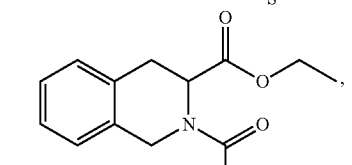

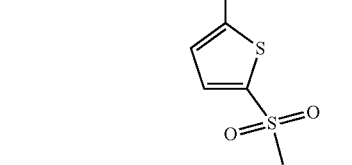

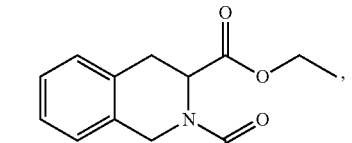

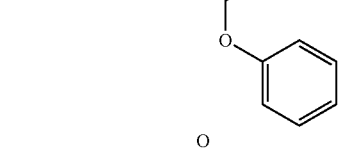

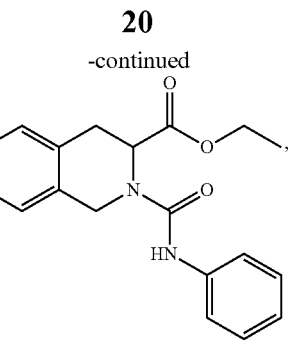

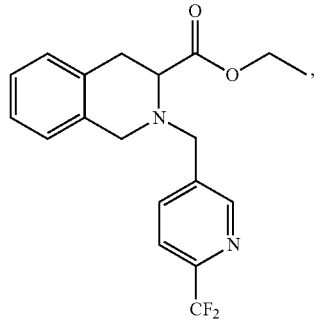

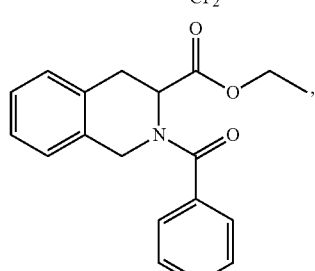

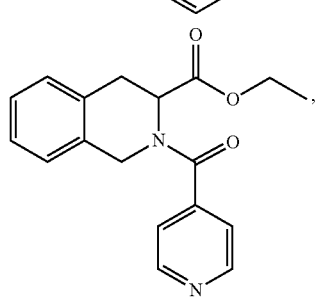

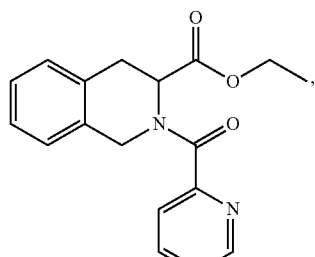

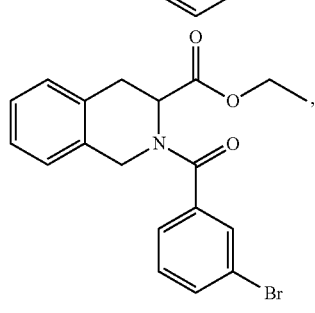

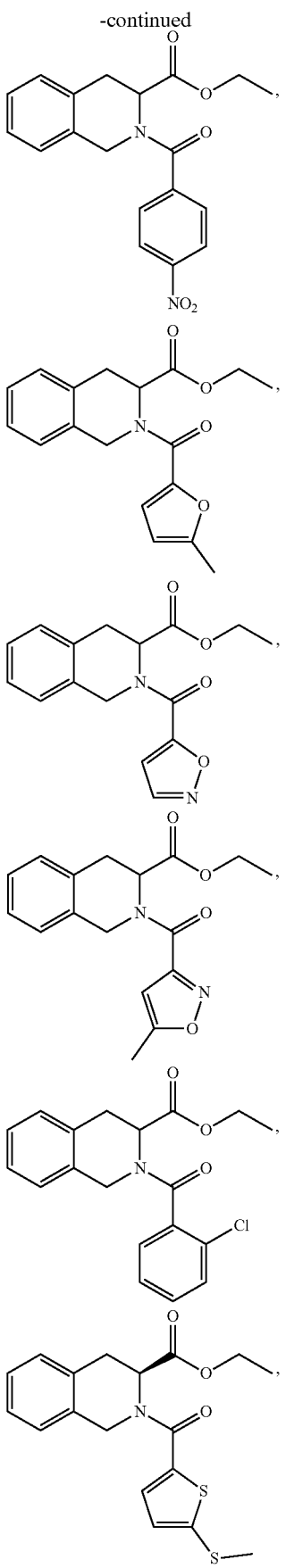
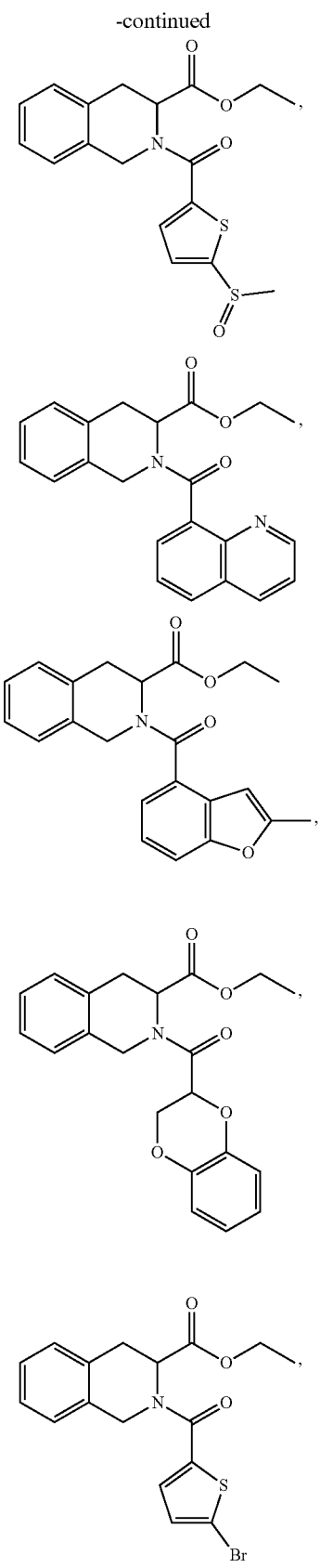

-continued
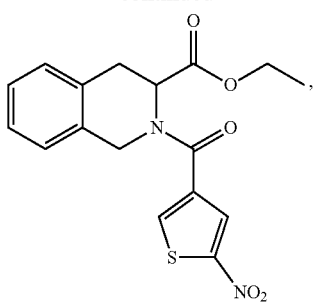
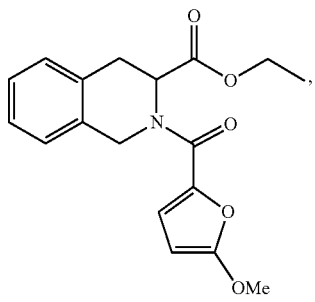
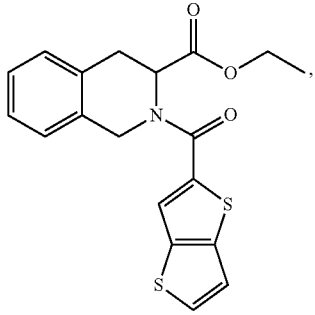
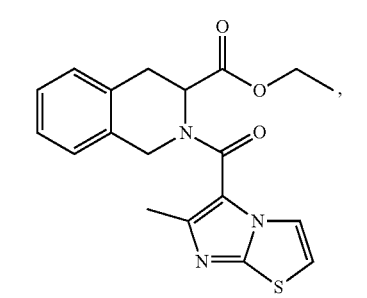
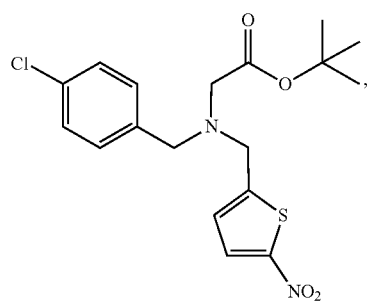
-continued
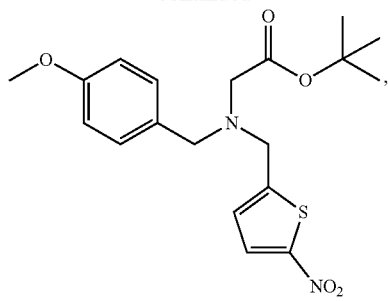
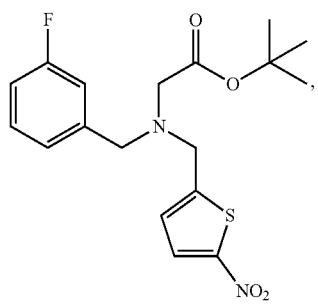
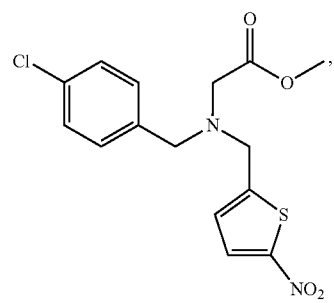
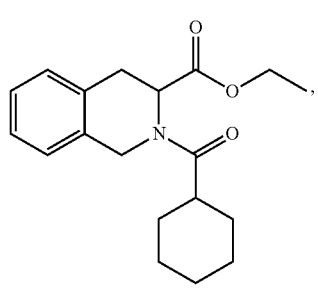
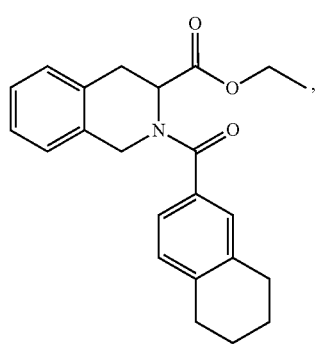

-continued

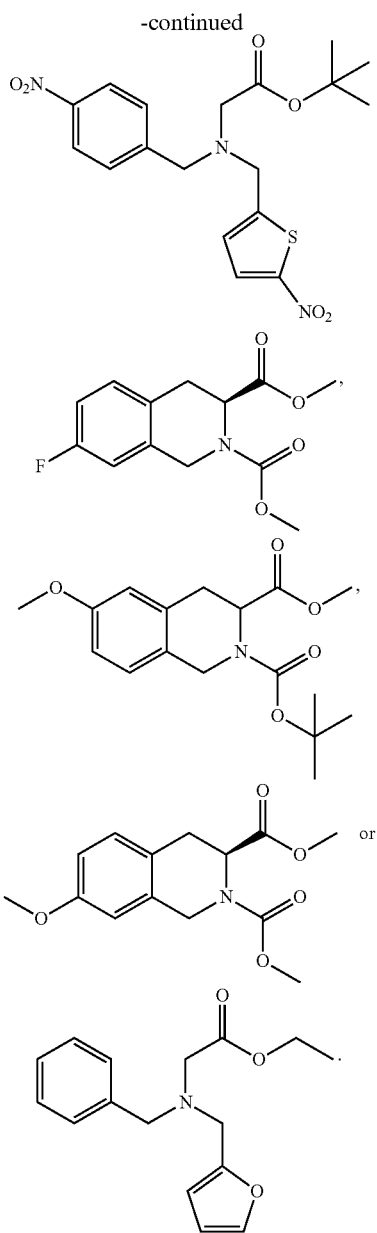

DETAILED DESCRIPTION OF THE INVENTION

Definitions

Figure 1:
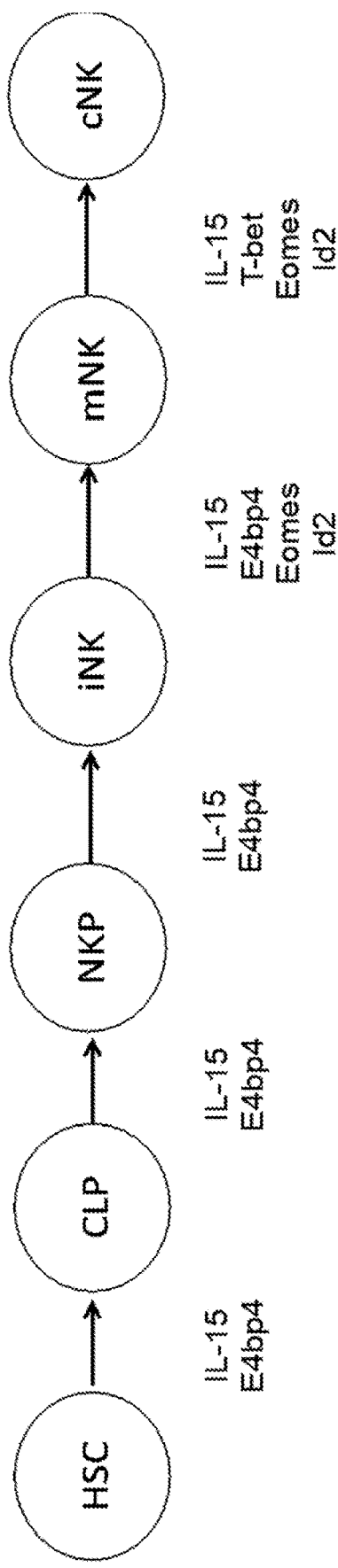
FIG. 1: NK cell developmental pathway. NK cells are differentiated from Hematopoietic Stem Cells (HSCs). NK cells develop from HSC into Common Lymphoid Progenitor (CLP) cells, NK progenitor (NKP) cells, immature NK (iNK) cells, mature NK (mNK) cells and finally into conventional NK (cNK) cells, which circulate in the bloodstream. Below the diagram of the pathway are the cytokines and transcription factors that are required for NK cell development. IL-15 is one of the main cytokines required for the development of NK cells. Others are transcription factors required for the transitions shown on the diagram.

As used herein, the singular forms "a," "an" and "the" include plural referents unless the context clearly dictates otherwise.

The term comprising encompasses both "comprising" (open definition) and "consisting of" closed definition). In other words, if an embodiment, description, aspect or disclosure comprises the recited feature(s), the present invention also encompasses said embodiment, description, aspect or disclosure consisting of said feature(s).

The term "chemically feasible" means a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed herein and do not form part of the present invention.

An "analogue" of a chemical structure, as the term is used herein, refers to a chemical structure that preserves substantial similarity with the parent structure, although it may not be readily derived synthetically from the parent structure. A related chemical structure that is readily derived synthetically from a parent chemical structure is referred to as a "derivative."

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

When a group is recited, wherein the group can be present in more than a single orientation within a structure resulting in more than single molecular structure, e.g., a carboxamide group C(=O)NR, it is understood that the group can be present in any possible orientation, e.g., X—C(=O)N(R)—Y or X—N(R)C(=O)—Y, unless the context clearly limits the orientation of the group within the molecular structure.

Hydrocarbyl groups are groups that consist only of carbon and hydrogen, though the groups may be substituted one or more times, as defined herein. Hydrocarbyl groups include straight chain and branched groups. Compounds of formula (I) typically have hydrocarbyl groups with from 1 to 6 carbon atoms, particularly from 1 to 4 carbon atoms or from 1 to 3 carbon atoms. As used herein, the term "hydrocarbyl" encompasses aromatic and non-aromatic groups. Preferred hydrocarbyl groups include alkyl, alkenyl and alkynyl groups which are described further below.

Alkyl groups include straight chain and branched alkyl groups and cycloalkyl groups having from 1 to about 20 carbon atoms, and typically from 1 to 12 carbons, from 1 to 8 carbon atoms, from 1 to 6 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl.

Representative substituted alkyl groups can be substituted one or more times, as defined herein.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, as defined herein.

Alkenyl groups are alkyl groups, e.g. as described above, but which comprise at least one carbon-carbon double bond. Thus, alkenyl groups include straight chain and branched alkenyl groups and non-aromatic cycloalkenyl groups. Alkenyl groups are preferably, but not necessarily, bonded to the rest of a molecule through a carbon which forms part of a double bond. Representative substituted alkenyl groups can be mono-substituted or substituted more than once, as defined herein.

Alkynyl groups are alkyl groups, e.g. as described above, but which comprise at least one carbon-carbon triple bond. Thus, alkynyl groups include straight chain and branched alkynyl groups. Alkynyl groups are preferably, but not necessarily, bonded to the rest of a molecule through a carbon which forms part of a triple bond. Representative substituted alkynyl groups can be mono-substituted or substituted more than once, as defined herein.

Heterocyclyl groups/rings or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas in compounds of formula (I) heterocyclyl rings typically have 5 to 10 ring members. A heterocyclyl ring can be a 5-membered ring with one heteroatom, a 6-membered ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom as described herein. Heterocyclyl groups can be unsubstituted, or can be substituted as discussed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. In compounds of formula (I) heteroaryl rings typically have 5 to about 10 ring members. A heteroaryl group is a variety of a heterocyclyl group that possesses an aromatic electronic structure. Likewise a heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Halogen refers to fluorine, chlorine, bromine or iodine.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH4+ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionisable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications.

Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), Int J. Pharm., 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patient's body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or subcombinations of the above-listed embodiments.

In various embodiments, a compound as shown in any of the Examples, or among the exemplary compounds, is provided.

Provisos may apply to any of the disclosed categories or embodiments wherein any one or more of the other above disclosed embodiments or species may be excluded from such categories or embodiments.

Natural Killer Cells

Natural Killer (NK) cells exhibit the highest level of cytotoxic activity within the immune system. NK cells are similar to B cells and T cells, but lack specific cell surface antigen receptors. Instead, NK cells have activatory and inhibitory receptors that recognise motifs.

NK cells circulate in the blood and the peripheral lymphoid organs such as lymph nodes and spleen. They can become activated by cytokines or upon encountering target cells. The recognition and elimination of target cells is based on balancing between inhibitory and activatory signals. Activatory signals are generated by activatory receptors ($NKG_2D$, $NKp_{46}$, $NKp_{30}$) binding to ligands, which can be present not only on cancerous, pathogen-infected and damaged cells, but also on healthy cells. On the other hand, inhibitory signals are generated when inhibitory receptors (KIR, $CD_{94}$/$NKG_2A$) on NK cells bind to Major Histocompatibility Complex (MHC) Class I molecules that are normally present on all healthy cells. MHC Class I molecules on target cells are absent or greatly downregulated, making them ideal NK cell targets. This allowed NK cells to distinguish between target and healthy cells. In order for NK cells to recognise and kill target cells, overall activatory signals must be greater than inhibitory signals.

NK cells recognise and kill cancerous, pathogen-infected and damaged cells without prior sensitisation, making them part of the innate immune response. For example, NK cells provide an early response to virus infection, occurring prior to T cell killing of infected cells. NK cells can kill target cells within minutes. NK cells also secrete cytokines and "weaponise" other parts of the immune system. For example, NK cells promote T cell effector function and enhance antibody-directed cellular cytotoxicity (ADCC).

NK cells are differentiated from haematopoietic stem cells (HSCs) via the pathway set out in FIG. 1. In more detail, NK cells develop from HSCs into Common Lymphoid Progenitor (CLP) cells, pre-NK progenitor (pre-NKP) cells, NK progenitor (NKP) cells, immature NK (iNK) cells, mature NK (mNK) cells and finally into conventional NK (cNK) cells, which circulate in the bloodstream. Although this terminology derives from NK cell development in mice, a corresponding pathway occurs in human NK cell development. For example, HSCs develop through multiple stages of precursors (stage 1, 2 and 3), before developing into mature NK cells (stages 4 and 5). For consistency, references HSCs, CLPs, pre-NKPs, NKPs, iNK, mNK, cNK and NK cells are used herein.

However, in the context of the present invention, these terms are interchangeable with stages 1 to 5 of the human nomenclature. Below the diagram of the pathway in FIG. 1 are the cytokines and transcription factors that are essential for NK cell development. IL-15 is one of the main cytokine required for the development of NK cells. Other extrinsic factors, such as specific stromal cells, are also required for the development and maturation of NK cells. According to the present invention, Hematopoietic Progenitor Cells (HPCs) are a heterogeneous population containing multi-potential progenitors such as HSCs, CLPs and also NKPs. HPCs are referred to as lineage negative cells, as they have not yet committed to a developmental pathway. Accordingly, in the context of the present invention, HSCs, CLP cells and NKP cells are all HPCs and a reference to HPCs is a reference to any of HSCs, CLP cells and/or CLP cells, or any combination thereof, unless explicitly stated to the contrary.

Due to the importance of NK cells in immune response, multiple clinical trials have tested the efficacy of NK cells in adoptive transfer protocols. Typically this is allogenic transfer, with the NK cells being isolated from a healthy donor and expanded. However, the downregulation of MHC Class I molecules on target cells is partial and the KIR genotype from donors and recipients may be similar. Due to this, NK cells transfused into recipients, even from different individuals may not attach target cells if their KIRs recognise MHC Class I molecules. Therefore, it is crucial that NK cell donors must be screened for their KIR genotype, where the donor must have the appropriate KIR allelic polymorphism to the recipient to allow recognition of target cells for destruction. Moreover, the expanded products were found to have lower clinical success rate than expected, with less ability to kill cancerous or infected cells.

An NK cell may be defined in terms of its marker expression, its function/activity, or a combination thereof. Such definitions are standard in the art and methods are known by which marker expression and/or NK cell activity may be assessed. Thus, one of skill in the art would readily be able to categorise a cell as an NK cell using standard methodology and definitions.

For example, mNK and cNK cells may be recognised by their expression of the surface markers CD16 (FcγRIII) and/or CD56, typically both CD16 and CD56 in humans, and NK1.1 or NK1.2 in some mice strains. NKp46 is another marker for mNK and cNK cells, and is expressed in humans and several mice strains. Thus, NKp46 may be used as a marker for NK cells either with or without CD16 and/or CD56 (in humans) or with or without NK1.1 or NK1.2 (in mice). Other examples of makers which can be used to identify/define NK cells according to the present invention include Ly49, natural cytotoxicity receptors (NCRs), CD94, NKG2, killer-cell immunoglobulin-like receptors (KIRs), and/or leukocyte inhibitory receptors (ILT or LIR), or any combination thereof, including in combination with CD16 and or CD56 (in humans) or NK1.1/NK1.2 (in mice). In some preferred embodiments mature NK cells according to the invention (i.e. mNK and cNK cells) are CD56$^+$ and CD45$^+$, and may be also be CD16$^+$. As used herein, the term mature human NK cell encompasses NK cells that are CD56$^{bright}$ (stage 4) and CD56$^{dim}$ (stage 5), both of which are CD56$^+$. Mature NK cells may also be defined by the absence of markers, such as CD34, and lymphocyte markers CD3 and/or CD19. Thus, mature NK cells of the invention may be CD56$^+$, CD45$^+$, CD16$^+$, CD3$^-$ and/or CD19$^-$, or any combination thereof, such as CD56$^+$, CD45$^+$, CD16$^+$, CD3$^-$ and CD19$^-$.

In addition or alternatively, an NK may be identified by/defined in terms of its activity. For example, an NK cell may be identified/defined by the presence of cytolytic granules within its cytoplasm, by its ability to secrete antimicrobial molecules such as α-defensins, and/or its ability to secrete cytokines such as TNF-α, IL-10, IFN-γ and TFG-β.

Unless otherwise stated herein, a reference to NK cells includes a reference to iNK, mNK and cNK cells. HSCs, CLP cells and NKPs will typically be referred to as such.

Expanded NK Cell Populations

As disclosed herein, the invention provides methods for generating an expanded population of NK cells (referred to interchangeably herein as an expanded NK cell population or an NK cell population). Any of the disclosure herein in relation to NK cells of the present invention may also be applied to an expanded NK cell population of the invention.

Accordingly, the present invention provides an expanded NK cell population. Typically an expanded NK cell population of the invention comprises iNK cells, mNK cells and/or cNK cells, or a combination thereof. Said population may comprise HPCs, such as HSCs, CLP cells and/or NKPs, or a combination thereof, although the numbers of such cells is typically low relative to the number of NK cells, as the majority of these HPCs have differentiated into NK cells in the population. Said population may comprise other immune and/or non-immune cells. Again, the number of any such cells is typically low relative to the number of NK cells present in the population.

As a non-limiting example, at least 60%, at least 70%, at least 80%, at least 85%, at least 90%, at least 91%, at least 92%, at least 93%, at least 94%, at least 95%, at least 96%, at least 97%, at least 98%, at least 99% or more, up to 100% of the cells of an expanded NK cell population of the invention may be NK cells. Typically at least 80%, preferably at least 90%, more preferably at least 95% of the cells of an expanded NK cell population of the invention are NK cells.

In some embodiments, at least 60%, at least 70%, at least 80%, at least 85%, at least 90%, at least 91%, at least 92%, at least 93%, at least 94%, at least 95%, at least 96%, at least 97%, at least 98%, at least 99% or more, up to 100% of the cells of an expanded NK cell population of the invention are mature NK cells (i.e. mNK cells and/or cNK cells). Preferably at least 80%, more preferably at least 90%, and even more preferably at least 95%, even more preferably at least 98% or more of the cells of an expanded NK cell population of the invention are mature NK cells.

The number of HPCs (including HSCs, CLP cells and/or NKPs) may be less than 40%, less than 30%, less than 25%, less than 20%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1% of the cells of the expanded NK cell population. Typically the number of HPCs (including HSCs, CLP cells and/or NKPs) is less than 20%, preferably less than 10%, more preferably less than 5%, even more preferably less than 2% or less of the cells of the expanded NK cell population.

The number of other immune and/or non-immune cells may be less than 40%, less than 30%, less than 25%, less than 20%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1% of the cells of the expanded NK cell population. Typically the number of other immune and/or non-immune cells is less than 20%, preferably less than 10%, more preferably less than 5% of the cells, even more preferably less than 2%, or less of the expanded NK cell population.

As described herein, the expanded NK cell populations made by the methods of the present invention offer several advantages over NK cell populations made by conventional adoptive transfer methods. In particular, the methods of the present invention enable the production of expanded populations with greater number of NK cells compared with conventional methods. Further, a greater proportion of the NK cells in a population of the invention are functional, preferably fully functional, compared with populations obtained by conventional methods, in which a large number of the NK cells are "exhausted".

As used herein, the term "exhausted" in the context of NK cells means that an NK cell or expanded NK cell population has lost at least some of its effector functions, such as cytotoxic function, cytokine production and/or ADCC. Thus, an exhausted NK cell or expanded NK cell population may exhibit impaired survival, impaired cytotoxic function, altered or impaired cytokine production and/or impaired ADCC. For example, an exhausted NK cell or exhausted NK cell population may exhibit at least a 50% reduction in one of its effector functions. For example, at least a 50% reduction in cytokine secretion, at least a 50% reduction in ADCC and/or at least 50% reduction in cytotoxic activity. These values may be quantified relative to any appropriate control as defined herein. Any appropriate technique can be used to determine effector function, and hence to quantify and reduction therein. Suitable techniques are known in the art. Alternatively and/or in addition, exhausted NK cells may exhibit altered marker expression, such as an increase in the expression of one or more inhibitory receptor (as described herein) and/or a decrease in the expression of one or more activatory receptor (as described herein). In some embodiments, increased expression of NKG2A and/or Tim3 may be used as a marker for NK cell exhaustion. Again, the expression of these markers may be quantified relative to any appropriate control as defined herein.

In contrast, the terms "functional" and "fully functional" in the context of NK cells means that an NK cell or expanded NK cell population has all of the expected effector functions when responding to a given immune challenge. Thus, a (fully) functional NK cell or expanded NK cell population will typically exhibit cytotoxic function, cytokine production and/or ADCC as would be observed in vivo when NK cells are activated in response to an immune challenge, and will typically exhibit enhanced survival compared with NK cells produced using conventional methods. Alternatively and/or in addition, (fully) functional NK cells may exhibit altered marker expression, such as an increase in the expression of one or more activatory receptor (as described herein) and/or a decrease in the expression of one or more inhibitory receptor (as described herein). As a non-limiting example, a functional (mature) human NK cell may be CD56$^+$ and/or CD45$^+$, preferably both CD56$^+$ and CD45$^+$.

As a non-limiting example, the cytotoxicity of NK cells can be determined using a degranulation assay in NK cells co-incubated with 'target cells'. A degranulation assay involves analysing the expression of CD107a within the NK cell population. The amount of CD107a correlates with cytokine secretion and NK cell-mediated lysis of target cells. NK cells can also be analysed for the expression of Interferon-γ (IFN-γ), which is the main cytokine secreted when functional NK cells are activated. NK cells that are functional should express similar or higher CD107a as well as IFN-γ when compared to a control.

Any increase in NK cell number/functionality in an expanded NK cell population made by a method of the present invention may be compared with the NK cell number/function of an NK cell population obtained from a control method as described herein. A control method may be any standard method known in the art for producing NK cell populations. For example, a control method may use conventional adoptive transfer techniques, rather than a method using a REV-ERB inhibitor according to the present invention. NK cells and NK cell populations produced by such control/standard methods may be used as control cells and populations as described herein.

As an expanded NK cell population of the present invention comprises significantly fewer exhausted NK cells compared to conventionally prepared NK cell populations, but instead contains a higher proportion of fully functional NK cells, this advantageously allows the use of smaller numbers of cells to treat patients.

As described herein, the methods of the invention produce expanded NK cell populations with a higher proportion of (fully) functional NK cells compared with conventional methods, which produce populations with large numbers of "exhausted" NK cells. Typically, in an expanded NK cell population of the invention at least 50%, at least 60%, at least 70%, at least 80%, at least 85%, at least 90%, at least 91%, at least 92%, at least 93%, at least 94%, at least 95%, at least 96%, at least 97%, at least 98%, at least 99% or more, up to 100% of the NK cells of an expanded NK cell population of the invention are (fully) functional. Typically at least 80%, preferably at least 90%, more preferably at least 95%, even more preferably at least 98% or more of the NK cells of an expanded NK cell population of the invention are fully functional, according to any definition (e.g. marker and/or effector function definition) herein.

An expanded NK cell population of the invention may be produced by any of the methods disclosed herein. Typically an expanded NK cell population of the invention is produced by an ex vivo method as disclosed herein.

E4bp4

E4bp4 (also known as Nfil3) is a basic leucine zipper protein transcription factor which is involved in the regulation of IL-3 expression, and is involved in the coordinating the circadian clock. The genomic DNA sequence of the human E4bp4 gene is given in SEQ ID NO: 1 (Genbank Accession No. X64318, version X64318.1). As shown in FIG. 1, E4bp4 is expressed in CLPs and is critical in the production of NK cells from blood stem cell progenitors. Mice with the E4bp4 gene deleted do not have functional NK cells, but have normal numbers of T and B cells. In contrast, overexpression of E4bp4 in HSCs in vitro increases NK cell production. Thus, E4bp4 is a lineage commitment factor, controlling the development of NKPs from HSCs (FIG. 1). E4bp4's critical function in NK cells is specific to the early stages of the developmental pathway, as specific ablation of E4bp4 in peripheral mNK cells does not affect NK cell number or response to cytomegalovirus infection. In addition E4bp4 regulates other transcription factors that are essential in NK cell development, such as Id2 and Eomes.

Although IL-7 and IL-15 have been shown to regulate E4bp4 expression, generally very little is known about how either extrinsic or intrinsic stimuli influence E4bp4. Transcription factors such as E4bp4 can be hard to target because of their structure and function. For example, they usually lack enzymatic activity or cofactor binding sites. However, the present inventors have previously demonstrated that E4bp4 expression can be increased using a compound which inhibits the activity of REV-ERB (see PCT/GB2018/050542, particularly the examples, which is herein incorporated by reference in its entirety). Further, the present inventors have demonstrated that the use of a REV-ERB inhibitor to increase E4bp4 expression results in an increase in NK cell number. Without wishing to be bound by theory, REV-ERB binds to porphyrin heme, and it is this characteristic that is believed to make REV-ERB a druggable target (see below). In sum, the inventors have shown that by targeting REV-ERB and inhibiting its activity, it is possible to increase E4bp4 expression and hence increase NK cell number. Accordingly, the present invention is concerned with compounds which inhibit the action of REV-ERB, and their use in increasing E4bp4 expression, and hence NK cell number.

Increase in E4bp4 Expression

Accordingly, the present invention provides ex vivo methods for producing expanded NK cell populations, and therapeutic methods and applications for increasing NK cell number in a patient in need thereof. As disclosed herein, said methods and applications involve the use of a compound which inhibits the action of REV-ERB. Typically said compounds act by increasing E4bp4 expression.

An increase in E4bp4 expression may be measured relative to a control. Thus, the expression of E4bp4 in a sample of HPCs, an expanded NK cell population or in a sample obtained from a patient to be treated according to the invention may be compared with the expression of E4bp4 in a control. Expression may be quantified in terms of gene and/or protein expression, and may be compared with expression of a control (e.g. housekeeping gene or protein). The actual amount of the E4bp4 gene, mRNA transcript and/or protein, such as the mass, molar amount, concentration or molarity of the E4bp4 gene, mRNA transcript and/or protein, or the number of mRNA molecules per cell in a sample of HPCs, an expanded NK cell population or in a sample obtained from a patient to be treated according to the invention and the control may be assessed and compared with the corresponding value from the control. Alternatively, the expression of the E4bp4 gene and/or protein in a sample of HPCs, an expanded NK cell population or in a sample obtained from a patient to be treated according to the invention may be compared with that of the control without quantifying the mass, molar amount, concentration or molarity of the one or more gene and/or protein.

Typically the control is an equivalent population or sample in which no increase in E4bp4 expression has been effected. As a non-limiting example, in the case where a patient is treated with a compound that inhibits REV-ERB activity in order to increase E4bp4 expression, a suitable control would be a different individual to which the compound has not been administered or the same individual prior to administration of the compound. Conventional methods for the ex vivo expansion of NK cells, including known methods may be considered control methods according to the present invention.

In the context of the present invention, a reference to increasing E4bp4 expression may be understood to mean that, the expression of E4bp4 is increased by at least 10%, at least 20%, at least 30%, at least 40%, at least 50%, at least 60, at least 70%, at least 80%, at least 85%, at least 90%, at least 95%, at least 100%, at least 150%, at least 200% compared with the control. Typically E4bp4 expression is increased by at least 50%, preferably at least 70%, more preferably at least 80%, even more preferably at least 90% or more compared with the control.

A reference to increasing E4bp4 expression may be understood to mean that, the expression of E4bp4 is increased by at least 1.5-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 4-fold, at least 5-fold, at least 6-fold, at least 7-fold, at least 8-fold, at least 9-fold, at least 10-fold or more relative to a control. Typically E4bp4 gene expression is increased by at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, or more compared with the control. Typically E4bp4 protein expression is increased by at least 2-fold, at least 3-fold, preferably at least 5-fold, more preferably at least 6-fold or more compared with the control.

The expression of the E4bp4 gene and/or protein according to the invention may be determined by quantitative and/or qualitative analysis. Typically, gene expression may be expressed in terms of mRNA levels.

The expression level of the E4bp4 gene and/or protein according to the invention encompasses the mass of the E4bp4 mRNA transcript and/or protein, the molar amount of the E4bp4 gene, mRNA transcript and/or protein, the concentration of the E4bp4 gene and/or protein and the molarity of the E4bp4 gene and/or protein. This expression level may be given in any appropriate units. For example, the concentration of the E4bp4 gene and/or protein may be given in pg/ml, ng/ml or µg/ml.

The expression level of the E4bp4 gene and/or protein according to the invention may be measured directly or indirectly.

The relative expression of the E4bp4 gene and/or protein according to the invention relative to a control may be determined using any appropriate technique. Suitable standard techniques are known in the art, for example Western blotting, enzyme-linked immunosorbent assays (ELISAs) and RT-qPCR.

The expression level of the E4bp4 gene and/or protein may be increased compared with a control for at least 6 hours, at least 12 hours, at least 24 hours, at least 30 hours, at least 36 hours, at least 42 hours, at least 48 hours, at least 54 hours, at least 60 hours, at least 72 hours, at least 4 days, at least 5 days, at least 6 days, at least 1 week. Preferably, the expression level of the E4bp4 gene and/or protein is increased for at least 12 to 72 hours. Typically this is assessed relative to the last administration of the compound which inhibits REV-ERB activity.

The expression level of the E4bp4 gene and/or protein may be increased compared with a control for at least one, at least two, at least three, at least four, at least five, at least ten, at least 20, at least 30, at least 40 or more passages of the NK cell precursors in culture. The expression level of the E4bp4 gene and/or protein may be altered indefinitely.

REV-ERB

REV-ERB proteins are members of the nuclear receptor family of intracellular transcription factors. The mRNA sequence of the human REV-ERBα gene (Nr1d1) is given in SEQ ID NO: 3 (Genbank Accession No. NM_021724, version NM_021724.4). The mRNA sequence of the human REV-ERBβ gene (Nr1d2) is given in SEQ ID NO: 5 (Genbank Accession No. AB307693, version AB307693.1). REV-ERB regulates the circadian clock, and has also been implicated in the regulation of cartilage breakdown.

The present inventors have previously demonstrated that inhibition of REV-ERB activity is sufficient to elicit a significant increase in E4bp4 expression, and that this in turn brings about an expansion of NK cells, resulting in an increase in NK cell number (see PCT/GB2018/050542, particularly the examples, which is herein incorporated by reference in its entirety). Inhibition of REV-ERB activity can bring about an increase in NK cell number, and that typically the resulting NK cells are (fully) functional as defined herein. The effect of REV-ERB inhibition is mediated in an E4pb4-dependent manner. Without wishing to be bound by theory, it is believed that inhibition of REV-ERB activity results in an increase in E4bp4 expression (E4bp4 expression is normally repressed by REV-ERB), and that the E4bp4 acts to stimulate the production of NK cells (as shown in FIG. 1). In particular, the present inventors have previously demonstrated that the small molecule SR8278 is capable of binding to the porphyrin heme moiety of REV-ERB, resulting in inhibition of REV-ERB activity and an increase in NK cell number.

However, the pharmacological profile of SR8278 is such that it is not ideal for use in a clinical setting. Furthermore, the lack of information on the mechanism of action of SR8278 and the lack of suitable structure-activity relationships surrounding this molecule has hindered the discovery of other compounds with REV-ERB inhibitory activity. Indeed, although many synthetic ligands for REV-ERB have been generated in the art, the vast majority of these have been identified as agonists, with over 300 REV-ERB agonists identified. The present inventors have generated a library of novel compounds, and have demonstrated that such compounds possess improved REV-ERB inhibitory activity compared with one known REV-ERB inhibitor, SR8278.

Accordingly, the present invention is concerned with such improved REV-ERB antagonists, i.e. compounds with improved inhibitory activity against the action of REV-ERB, and the use of such compounds in increasing E4bp4 expression, and hence NK cell number.

Inhibition of REV-ERB Activity

The present invention relates to the use of compounds to inhibit the action of REV-ERB, i.e. compounds which inhibit REV-ERB activity. REV-REB activity may be inhibited by any appropriate means. Suitable standard techniques are known in the art. Inhibition may take place via any suitable mechanism, depending for example on the nature (see below) of the compound used, e.g. steric interference in any direct or indirect interaction or inhibition of REV-ERB. In the context of the present invention a REV-ERB inhibitor (interchangeably referred to herein as a REV-ERB antagonist) is any compound which inhibits, decreases, suppresses or ablates the action of REV-ERB, whether in part or completely.

A decrease in REV-ERB activity may be measured relative to a control. Thus, the activity of REV-ERB in a sample of NK precursor or progenitor cells, an expanded NK cell population or in a sample obtained from a patient to be treated according to the invention may be compared with the activity of REV-ERB in a control. Activity may be quantified in any appropriate terms, for example binding of REV-ERB to the E4bp4 gene, or in terms of E4bp4 expression as defined herein. Any appropriate technique or method may be used for quantifying REV-ERB activity. Suitable techniques are known in the art, for example luciferase assays for quantifying expression of a reporter gene.

Typically the control is an equivalent population or sample in which no REV-ERB inhibitory compound has been added, for example a sample obtained from a different individual to which the compound has not been administered, or the same individual the prior to administration of the compound. Conventional methods for the ex vivo expansion of NK cells, including known methods may be considered control methods according to the present invention.

In the context of the present invention, a reference to inhibiting REV-ERB activity may be understood to mean that, the activity of REV-ERB is decreased by at least 10%, at least 20%, at least 30%, at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, up to total (100%) inhibition of REV-ERB activity, as compared with the control. Typically REV-ERB activity is decreased by at least 50%, preferably at least 70%, more preferably at least 80%, more preferably at least 90%, even more preferably at least 95% or more compared with the control.

The activity of REV-ERB may be determined by quantitative and/or qualitative analysis, and may be measured directly or indirectly.

The activity of REV-ERB relative to a control may be determined using any appropriate technique. Suitable standard techniques are known in the art, such as by quantifying E4bp4 expression, and/or luciferase assays.

The activity of REV-ERB may be inhibited compared with a control for at least 6 hours, at least 12 hours, at least 24 hours, at least 30 hours, at least 36 hours, at least 42 hours, at least 48 hours, at least 54 hours, at least 60 hours, at least 72 hours, at least 4 days, at least 5 days, at least 6 days, at least 1 week. Preferably, the activity of REV-ERB is decreased for at least 12 to 72 hours. Typically this is assessed relative to the last administration of the compound which inhibits REV-ERB activity.

The activity of REV-ERB may be inhibited compared with a control for at least one, at least two, at least three, at least four, at least five, at least ten, at least 20, at least 30, at least 40 or more passages of the cells (either in vivo, or cultured ex vivo or in vitro). The activity of REV-ERB may be inhibited and/or the expression level of the E4bp4 gene and/or protein may be altered indefinitely.

In the context of the present invention any reference to inhibiting REV-ERB activity may be understood to mean inhibiting the activity of REV-ERBα and/or REV-ERBβ. In preferred embodiments, the activity of both REV-ERBα and REV-ERBβ is inhibited. Thus, the invention relates to compounds which inhibit REV-ERB activity, including compounds which inhibit REV-ERBα activity (i.e. REV-ERBα inhibitors, also referred to as REV-ERBα antagonists) and/or to compounds which inhibit REV-ERBβ activity (i.e. REV-ERBβ inhibitors, also referred to as REV-ERBβ antagonists). In preferred embodiments, the invention relates to compounds which inhibit the activity of both REV-ERBa and REV-ERBβ (i.e. REV-ERBα and REV-ERBβ inhibitors, also referred to as REV-ERBα and REV-ERBβ antagonists).

REV-ERB Antagonists/Inhibitors

REV-ERB inhibitory compounds of the invention may be specific for REV-ERB. By specific, it will be understood that the compound binds to REV-ERBα and/or REV-ERBβ, with no significant cross-reactivity to any other molecule, particularly any other protein. For example, modulator that is specific for REV-ERBα and/or REV-ERBβ will show no significant cross-reactivity with human neutrophil elastase. Cross-reactivity may be assessed by any suitable method. Cross-reactivity of REV-ERBα and/or REV-ERBβ inhibitor with a molecule other than REV-ERBα and/or REV-ERBβ may be considered significant if the inhibitor binds to the other molecule at least 5%, 10%, 15%, 20%, 25%, 30%, 35%, 40%, 45%, 50%, 55%, 60%, 65%, 70%, 75%, 80%, 85%, 90% or 100% as strongly as it binds to REV-ERBα and/or REV-ERBβ. An inhibitor that is specific for REV-ERBα and/or REV-ERBβ may bind to another molecule such as human neutrophil elastase at less than 90%, 85%, 80%, 75%, 70%, 65%, 60%, 55%, 50%, 45%, 40%, 35%, 30%, 25% or 20% the strength that it binds to REV-ERBα and/or REV-ERBβ. Preferably, the inhibitor binds to the other molecule at less than 20%, less than 15%, less than 10% or less than 5%, less than 2% or less than 1% the strength that it binds to REV-ERBα and/or REV-ERBβ.

REV-ERB inhibitory compounds of the invention may have off-target effects. An off-target effect is activity against a target other than REV-ERB. Typically compounds with off-target effects are encompassed by the present invention if the activity against the non-REV-ERB target is not significant compared with the activity against REV-ERB. Whether an off-target effect is significant may depend on the intended use of the compound. As a non-limiting example, a compound which may exert an off-target effect on the central nervous system would not be significant for a compound used in an ex vivo method as disclosed herein, but may be significant (depending on the magnitude of the off-target effect) for an in vivo therapeutic indication as disclosed herein. The presence and magnitude of any potential off target effects can be readily assessed using standard methods known in the art.

Small Molecules

The compounds of the invention used to inhibit REV-ERB activity as described herein are small molecules. As defined herein, small molecules are low molecular weight compounds, typically organic compounds. Typically, a small molecule has a maximum molecule weight of 900 Da, allowing for rapid diffusion across cell membranes. In some embodiments, the maximum molecular weight of a small molecule is 500 Da. Typically a small molecule has a size in the order of 1 nm.

According to the present invention, small molecules may be able to exert an inhibitory effect on REV-ERB activity by binding to the porphyrin heme moiety of REV-ERB. Thus in some preferred embodiments, a compound that inhibits the action of REV-ERB according to the present invention is a compound which binds to the porphyrin heme moiety of REV-ERB, and hence inhibits the activity of REV-ERB. Alternatively, the small molecule may act via a different mechanism, for example, by binding to a non-heme portion of REV-ERB. Standard techniques are known in the art for the production of small molecules, which can then readily be tested for REV-ERB inhibitory activity as described herein

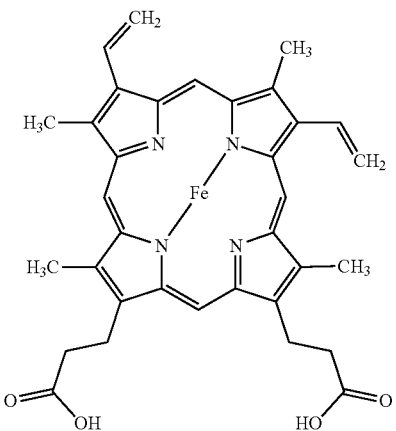

Structure of Porphyrin Heme

The inventors have generated new compounds that inhibit REV-ERB activity (referred to interchangeably herein as inhibiting the action of REV-ERB) based on the scaffold of SR8278, particularly by varying the amide substituent and/or the ethyl ester group. Accordingly, the compounds used in the present invention have formula (I):

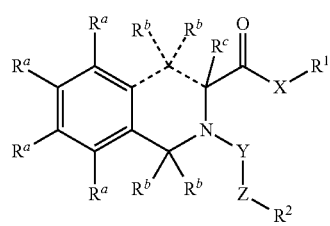
(I)

where: ------ represents bonds that are all either present or absent;

$R^1$ is selected from $C_{1-6}$ hydrocarbyl, and is optionally substituted with one or more groups independently selected from $C_{1-4}$ hydrocarbyl, —OR', —OC(O)R', —C(O)OR', —SR', —S(O)R', —S(O)$_2$R', —NR'$_2$, —NR'C(O)R', —C(O)NR'$_2$, —CN, —NO$_2$, -Ph, —CF$_3$ and halogen;

$R^2$ is selected from 5-10 membered heterocyclyl rings and $C_{1-6}$ hydrocarbyl, and is optionally substituted with one or more groups independently selected from $C_{1-4}$ hydrocarbyl, —OR', —OC(O)R', —C(O)OR', —SR', —S(O)R', —S(O)$_2$R', —NR'$_2$, —NR'C(O)R', —C(O)NR'$_2$, —CN, —NO$_2$, -Ph, —CF$_3$ and halogen;

X is selected from —O— and NR' or is absent;

Y is selected from —C(O)— and —CR'$_2$—;

Z is selected from —O— and —NR'— or is absent;

each $R^a$ is independently selected from H, $C_{1-4}$ hydrocarbyl, —OR', —OC(O)R', —C(O)OR', —SR', —S(O)R', —S(O)$_2$R', —NR'$_2$, —NR'C(O)R', —C(O)NR'$_2$, —CN, —NO$_2$, -Ph, —CF$_3$ and halogen;

each $R^b$ is independently selected from H, $C_{1-4}$ hydrocarbyl and —OR';

$R^c$ is selected from H and $C_{1-4}$ hydrocarbyl; and each R' is independently selected from H, $C_{1-4}$ hydrocarbyl and -Ph;

or a pharmaceutically acceptable salt thereof, provided that the compound is not:

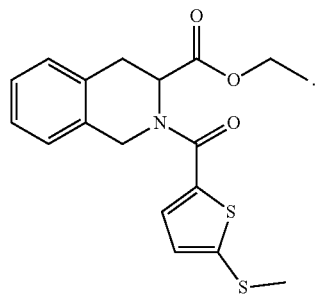
(SR8278)

As described above, ------ represents bonds that are all either present or absent.

Accordingly, the present invention relates to both closed ring structures of formula (Ia) and open ring structures of formula (Ib):

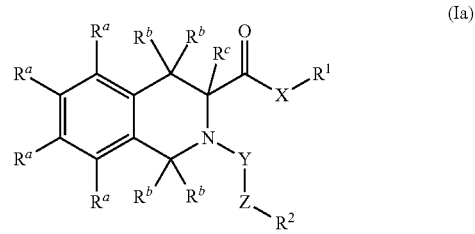
(Ia)

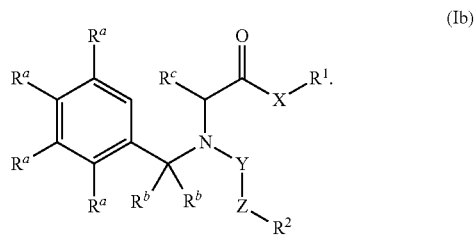
(Ib)

Preferably, ------ represents bonds that are all present and the compound is a closed ring structure of formula (Ia).

In compounds of formula (I), $R^1$ is selected from $C_{1-6}$ hydrocarbyl, and is optionally substituted with one or more groups independently selected from $C_{1-4}$ hydrocarbyl (preferably $C_{1-4}$ alkyl), —OR', —OC(O)R', —C(O)OR', —SR', —S(O)R', —S(O)$_2$R', —NR'2, —NR'C(O)R', —C(O)NR'$_2$, —CN, —NO$_2$, -Ph, —CF$_3$ and halogen. $R^1$ is preferably unsubstituted and, as such, is preferably selected from $C_{1-6}$ hydrocarbyl, preferably from $C_{1-6}$ alkyl and $C_{1-6}$ alkenyl. More preferably, $R^1$ is selected from $C_{1-6}$ alkyl, preferably from $C_{1-4}$ alkyl, such as from methyl, ethyl and propyl. Ethyl groups are particularly preferred.

In compounds of formula (I), $R^2$ is selected from 5-10 membered heterocyclyl rings and $C_{1-6}$ hydrocarbyl, and is optionally substituted. Preferably, $R^2$ is selected from optionally substituted 5-10 membered heterocyclyl rings.

The 5-10 membered heterocyclyl ring of $R^2$ preferably contains one to four, and more preferably one or two, heteroatoms. The heteroatoms are preferably selected from oxygen, nitrogen and sulfur. It will be appreciated that a heterocyclyl ring may comprise multiple of the same heteroatom, e.g. two nitrogen atoms, or a mixture of heteroatoms, e.g. a nitrogen atom and an oxygen atom.

$R^2$ is preferably selected from 5-10 membered heteroaryl rings, and more preferably from 5-, 6- or 9-membered heteroaryl rings. Non-limiting examples of 5-membered heteroaryl rings include furanyl, thiophenyl, oxazolyl, isooxazolyl, isothiazolyl, thiazolyl, pyrazolyl, imidazolyl, pyrrolyl and triazolyl. Non-limiting examples of 6-membered heteroaryl rings include pyridinyl, pyridazinyl, pyrimidinyl and pyrazinyl. Non-limiting examples of 9-membered heteroaryl rings include indolyl, isoindolyl, indazolyl, benzimidazolyl, azaindolyl, benzofuranyl, isobenzofuranyl, benzisoxazolyl and benzoxazolyl. Optionally substituted 5-membered heteroaryl rings are particularly preferred.

Where $R^2$ is optionally substituted $C_{1-6}$ hydrocarbyl, it is preferably selected from optionally substituted phenyl and optionally substituted $C_{1-6}$ alkyl.

Where $R^2$ is optionally substituted phenyl, the phenyl group is preferably substituted.

Where $R^2$ is optionally substituted $C_{1-6}$ alkyl, the alkyl group is preferably unsubstituted, and as such $R^2$ is preferably selected from $C_{2-4}$ alkyl, such as from ethyl, propyl (e.g. -iPr) and butyl (e.g. -tBu).

$R^2$ is optionally substituted with one or more groups independently selected from $C_{1-4}$ hydrocarbyl (preferably $C_{1-4}$ alkyl), —OR', —OC(O)R', —C(O)OR', —SR', —S(O)R', —S(O)$_2$R', —NR'$_2$, —NR'C(O)R', —C(O)NR'$_2$, —CN, —NO$_2$, -Ph, —CF$_3$ and halogen. Preferably, $R^2$ is unsubstituted or substituted with one or two of these groups. Particularly preferred substituents for $R^2$ include -Me, —OMe, —CN, —NO$_2$, —F, —Cl, —I and SMe.

In compounds of formula (I), X is selected from —O— and —NR'— or is absent. X is preferably —O—.

In compounds of formula (I), Y is selected from —C(O)— and —CR'$_2$—. Y is preferably —C(O)—.

In compounds of formula (I), Z is selected from —O— and —NR'— or is absent. Preferably, Z is selected from —O— or is absent. Where $R^2$ is an alkyl group, Z is preferably selected —O— and —NR'— and preferably is —O—. Where $R^2$ is a heterocyclyl ring, Z is preferably absent.

In compounds of formula (I), each $R^a$ is independently selected from H, $C_{1-4}$ hydrocarbyl (preferably $C_{1-4}$ alkyl), —OR', —OC(O)R', —C(O)OR', —SR', —S(O)R', —S(O)$_2$R', —NR'$_2$, —NR'C(O)R', —C(O)NR'$_2$, —CN, —NO$_2$, -Ph, —CF$_3$ and halogen. Preferably, each $R^a$ is independently selected from H, $C_{1-4}$ alkyl and —OR', and more preferably from H and $C_{1-4}$ alkyl. More preferably, each $R^a$ is preferably H.

In compounds of formula (I), each $R^b$ is independently selected from H, $C_{1-4}$ hydrocarbyl (preferably $C_{1-4}$ alkyl) and —OR'. Preferably, each $R^b$ is independently selected from H and $C_{1-4}$ alkyl, and more preferably is H.

In compounds of formula (I), $R^c$ is selected from H and $C_{1-4}$ hydrocarbyl (preferably $C_{1-4}$ alkyl). Preferably, $R^c$ is H.

In compounds of formula (I), each R' is independently selected from H and $C_{1-4}$ hydrocarbyl (preferably $C_{1-4}$ alkyl) and -Ph. Preferably, each R' is independently selected from H and $C_{1-4}$ alkyl, more preferably from H, methyl and ethyl, and more preferably from methyl and ethyl.

In preferred embodiments, $R^b$ and $R^c$ are all H, and so the compounds used in the present invention have the formula (II):

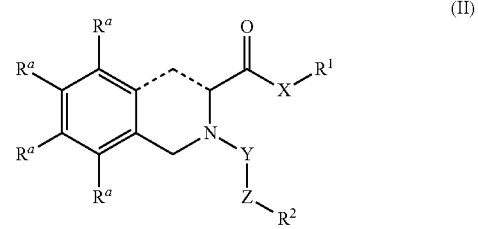

where $R^1$, $R^2$, $R^a$ and X, Y and Z are as defined previously.

In further preferred embodiments, $R^a$ are also all H, and so the compounds used in the present invention have the formula (III):

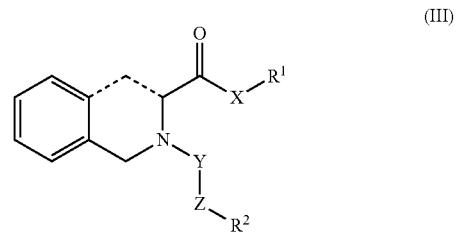

where $R^1$, $R^2$, X, Y and Z are as defined previously.

In further preferred embodiments, X is —O— and the compounds used in the present invention have the formula (IV):

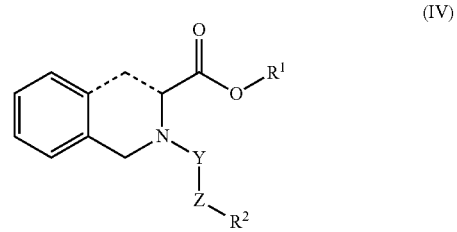

where $R^1$, $R^2$, Y and Z are as defined previously.

In further preferred embodiments, Y is —C(O)— and the compounds used in the present invention have the formula (V):

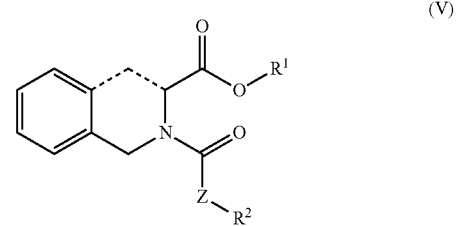

where $R^1$, $R^2$ and Z are as defined previously.

Still further preferred are compounds in which $R^1$ is ethyl, which have the formula (VI):

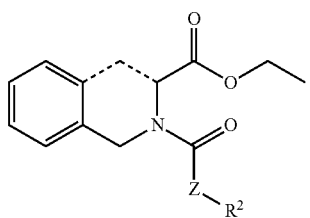

(VI)

where $R^2$ and Z are as defined previously.

For instance, the compound may be a closed ring structure and have the formula (VII):

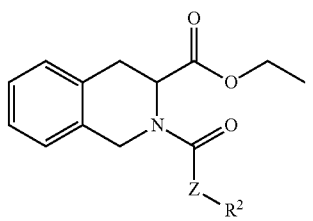

(VII)

where $R^2$ and Z are as defined previously.

Specific examples of compounds according to the present invention are set out in Table 1 below:

TABLE 1

| Exemplary compounds of the invention | |
|---|---|
| Compound | Structure |
| 1 | 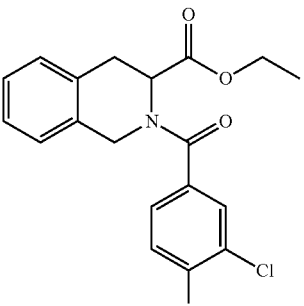 |
| 2 | 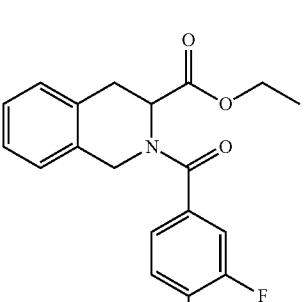 |

TABLE 1-continued

| Exemplary compounds of the invention | |
|---|---|
| Compound | Structure |
| 3 | 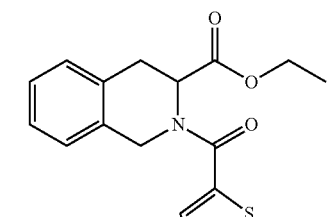 |
| 4 | 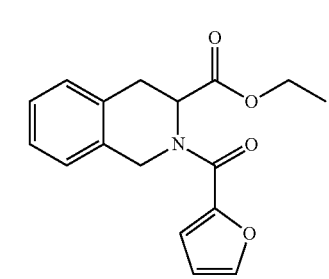 [SMILES: CCOC(=O)C1Cc2ccccc2CN1C(=O)c1ccco1] |
| 5 |  |
| 6 |  |
| 7 |  |

TABLE 1-continued

Exemplary compounds of the invention

| Compound | Structure |
|---|---|
| 8 | (tetrahydroisoquinoline-N-C(O)-isoxazol-5-yl, with ethyl ester) |
| 9 | (tetrahydroisoquinoline-N-C(O)-oxazol-5-yl, with ethyl ester) |
| 10 | (tetrahydroisoquinoline-N-C(O)-thiazol-5-yl, with ethyl ester) |
| 11 | (tetrahydroisoquinoline-N-C(O)-(4-methyloxazol-5-yl), with ethyl ester) |
| 12 | (tetrahydroisoquinoline-N-C(O)-(4-methylthiazol-5-yl), with ethyl ester) |
| 13 | (tetrahydroisoquinoline-N-C(O)-(4-methyl-2-phenylthiazol-5-yl), with ethyl ester) |
| 14 | (tetrahydroisoquinoline-N-C(O)-(3,4-dichlorophenyl), with methyl ester) |
| 15 | (tetrahydroisoquinoline-N-C(O)-(3,4-dichlorophenyl), with N-ethyl carboxamide) |
| 16 | (tetrahydroisoquinoline-N-C(O)-(1-methylimidazol-2-yl), with ethyl ester) |

TABLE 1-continued

Exemplary compounds of the invention

| Compound | Structure |
|---|---|
| 17 | 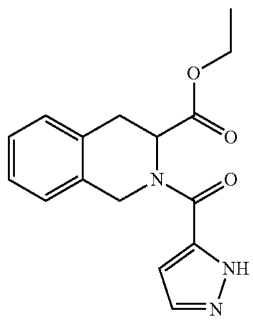 [SMILES: CCOC(=O)C1Cc2ccccc2CN1C(=O)c1ccn[nH]1] |
| 18 | 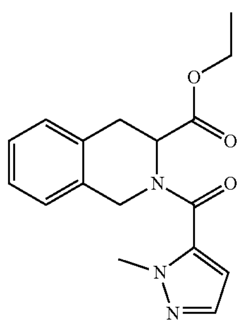 [SMILES: CCOC(=O)C1Cc2ccccc2CN1C(=O)c1ccnn1C] |
| 19 | 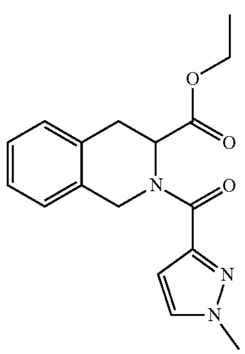 [SMILES: CCOC(=O)C1Cc2ccccc2CN1C(=O)c1ccn(C)n1] |
| 20 | 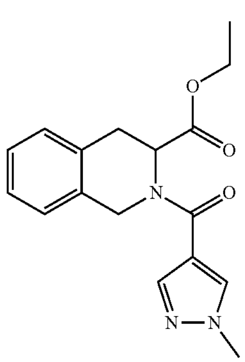 [SMILES: CCOC(=O)C1Cc2ccccc2CN1C(=O)c1cnn(C)c1] |
| 21 | |
| 22 | |
| 23 | |
| 24 | |

TABLE 1-continued

Exemplary compounds of the invention

| Compound | Structure |
|---|---|
| 25 | (ethyl 1,2,3,4-tetrahydroisoquinoline-3-carboxylate N-acylated with 3-methylpyridine-2-carbonyl) |
| 26 | (ethyl 1,2,3,4-tetrahydroisoquinoline-3-carboxylate N-acylated with 3-fluoropyridine-2-carbonyl) |
| 27 | (ethyl 1,2,3,4-tetrahydroisoquinoline-3-carboxylate N-acylated with 2-fluoropyridine-3-carbonyl) |
| 28 | (ethyl 1,2,3,4-tetrahydroisoquinoline-3-carboxylate N-acylated with 6-methylpyridine-3-carbonyl) |
| 29 | (ethyl 1,2,3,4-tetrahydroisoquinoline-3-carboxylate N-acylated with 3-fluoropyridine-4-carbonyl) |
| 30 | (ethyl 1,2,3,4-tetrahydroisoquinoline-3-carboxylate N-acylated with 3-methylisoxazole-4-carbonyl) |
| 31 | (ethyl 1,2,3,4-tetrahydroisoquinoline-3-carboxylate N-acylated with 5-methylisoxazole-3-carbonyl) |
| 32 | (ethyl 1,2,3,4-tetrahydroisoquinoline-3-carboxylate N-acylated with oxazole-2-carbonyl) |

TABLE 1-continued

Exemplary compounds of the invention

| Compound | Structure |
|---|---|
| 33 | ethyl 1,2,3,4-tetrahydroisoquinoline-3-carboxylate N-acylated with isothiazole-5-carbonyl |
| 34 | ethyl 1,2,3,4-tetrahydroisoquinoline-3-carboxylate N-acylated with isoxazole-4-carbonyl |
| 35 | ethyl 1,2,3,4-tetrahydroisoquinoline-3-carboxylate N-acylated with isoxazole-3-carbonyl |
| 36 | ethyl 1,2,3,4-tetrahydroisoquinoline-3-carboxylate N-acylated with 1H-indole-3-carbonyl |
| 37 | ethyl 1,2,3,4-tetrahydroisoquinoline-3-carboxylate N-acylated with thiazole-2-carbonyl |
| 38 | ethyl 1,2,3,4-tetrahydroisoquinoline-3-carboxylate N-acylated with 1H-imidazole-2-carbonyl |
| 39 | ethyl 1,2,3,4-tetrahydroisoquinoline-3-carboxylate N-acylated with 1H-pyrazole-4-carbonyl |
| 40 | ethyl 1,2,3,4-tetrahydroisoquinoline-3-carboxylate N-acylated with 1-methyl-1H-imidazole-4-carbonyl |

TABLE 1-continued

Exemplary compounds of the invention

| Compound | Structure |
|---|---|
| 41 | 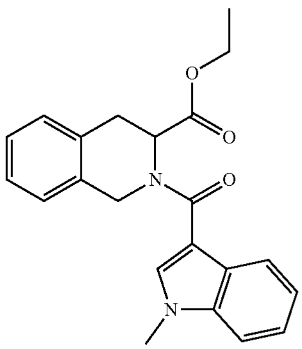 [SMILES: CCOC(=O)C1Cc2ccccc2CN1C(=O)c1cn(C)c2ccccc12] |
| 42 | 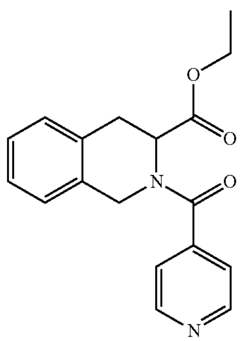 [SMILES: CCOC(=O)C1Cc2ccccc2CN1C(=O)c1ccncc1] |
| 43 | 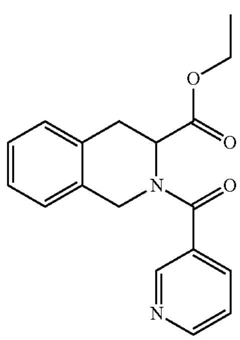 [SMILES: CCOC(=O)C1Cc2ccccc2CN1C(=O)c1cccnc1] |
| 44 | 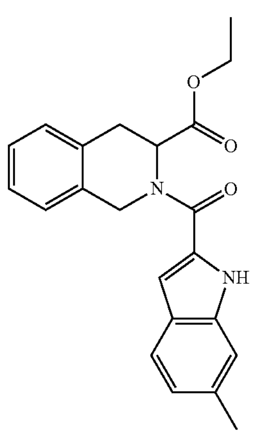 [SMILES: CCOC(=O)C1Cc2ccccc2CN1C(=O)c1cc2ccc(C)cc2[nH]1] |
| 45 | 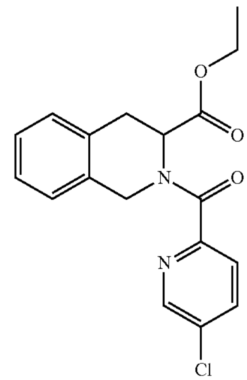 [SMILES: CCOC(=O)C1Cc2ccccc2CN1C(=O)c1ccc(Cl)cn1] |
| 46 | 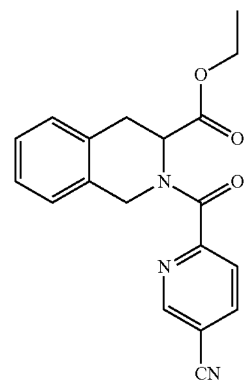 [SMILES: CCOC(=O)C1Cc2ccccc2CN1C(=O)c1ccc(C#N)cn1] |
| 47 | 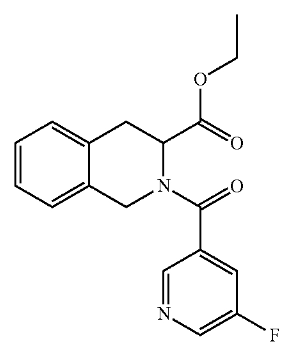 [SMILES: CCOC(=O)C1Cc2ccccc2CN1C(=O)c1cncc(F)c1] |
| 48 | 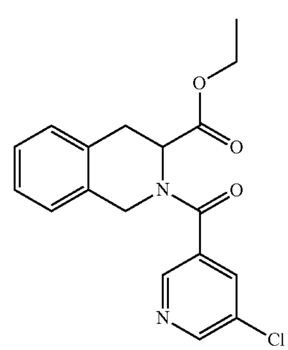 [SMILES: CCOC(=O)C1Cc2ccccc2CN1C(=O)c1cncc(Cl)c1] |

TABLE 1-continued

Exemplary compounds of the invention

| Compound | Structure |
|---|---|
| 49 | (ethyl 1,2,3,4-tetrahydroisoquinoline-3-carboxylate N-acylated with 2-methoxypyridine-3-carbonyl) |
| 50 | (ethyl 1,2,3,4-tetrahydroisoquinoline-3-carboxylate N-acylated with 5-methoxypyridine-3-carbonyl) |
| 51 | (ethyl 1,2,3,4-tetrahydroisoquinoline-3-carboxylate N-acylated with 5-fluoro-1H-indole-2-carbonyl) |
| 52 | (ethyl 1,2,3,4-tetrahydroisoquinoline-3-carboxylate N-acylated with 5-chloro-1H-indole-2-carbonyl) |
| 53 | (ethyl 1,2,3,4-tetrahydroisoquinoline-3-carboxylate N-acylated with 5-methoxy-1H-indole-2-carbonyl) |
| 54 | (ethyl 1,2,3,4-tetrahydroisoquinoline-3-carboxylate N-acylated with 3-nitro-1H-pyrazole-4-carbonyl) |
| 55 | (ethyl 1,2,3,4-tetrahydroisoquinoline-3-carboxylate N-acylated with 5-chloro-1-methyl-1H-pyrazole-4-carbonyl) |
| 56 | (ethyl 1,2,3,4-tetrahydroisoquinoline-3-carboxylate N-acylated with 4-chloro-1-methyl-1H-pyrazole-3-carbonyl) |

TABLE 1-continued
Exemplary compounds of the invention
| Compound | Structure |
|---|---|
| 57 | 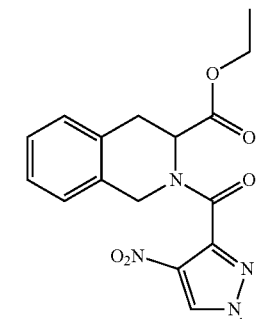 |
| 58 | 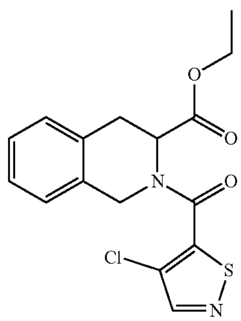 [SMILES: CCOC(=O)C1Cc2ccccc2CN1C(=O)c1sncc1Cl] |
| 59 | 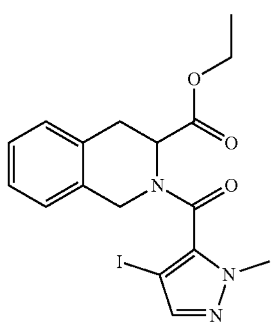 [SMILES: CCOC(=O)C1Cc2ccccc2CN1C(=O)c1c(I)cnn1C] |
| 60 | 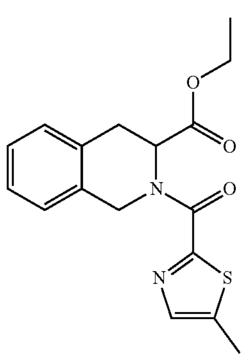 [SMILES: CCOC(=O)C1Cc2ccccc2CN1C(=O)c1ncc(C)s1] |
| 61 | 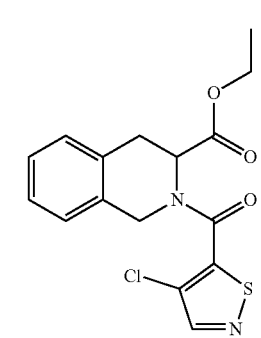 |
| 62 | |
| 63 | |
| 64 | |

TABLE 1-continued

Exemplary compounds of the invention

| Compound | Structure |
|---|---|
| 65 | ethyl 2-(phenoxycarbonyl)-1,2,3,4-tetrahydroisoquinoline-3-carboxylate |
| 66 | ethyl 2-(phenylcarbamoyl)-1,2,3,4-tetrahydroisoquinoline-3-carboxylate |
| 67 | ethyl 2-(N-(2-methylbenzyl)-5-(methylthio)thiophene-2-carboxamido)acetate |
| 68 | ethyl 2-(N-benzyl-5-(methylthio)thiophene-2-carboxamido)acetate |
| 69 | ethyl 2-(N-benzyloxazole-5-carboxamido)acetate |
| 70 | ethyl 2-(N-benzyl-phenoxycarbonylamino)acetate |
| 71 | ethyl 2-(N-benzylacetamido)acetate |
| 72 | ethyl 2-(N-benzylfuran-2-carboxamido)acetate |
| 73 | ethyl 2-(N-benzyl-(furan-2-ylmethyl)amino)acetate |
| 74 | ethyl 2-((furan-2-ylmethyl)-1,2,3,4-tetrahydroisoquinoline-3-carboxylate |
| 75 | ethyl 2-(N-benzyl-4-methyloxazole-5-carboxamido)acetate |

TABLE 1-continued

Exemplary compounds of the invention

| Compound | Structure |
|---|---|
| 76 | 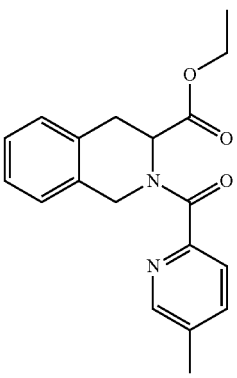 [SMILES: CCOC(=O)C1Cc2ccccc2CN1C(=O)c1ccc(C)cn1] |

Compounds 7, 11, 27, 72 and 73 are preferred.
Compounds 7 and 11 are particularly preferred:

(compound 7)

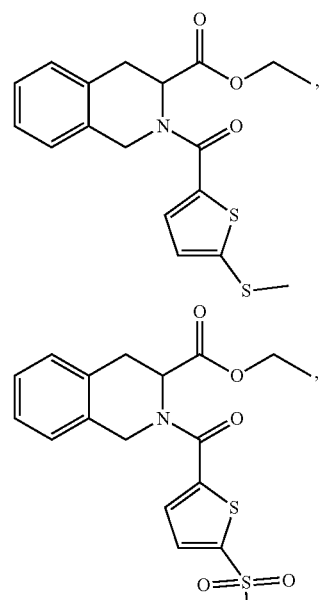

(compound 11)

The compound of formula (I) is not SR8278, i.e. is not:

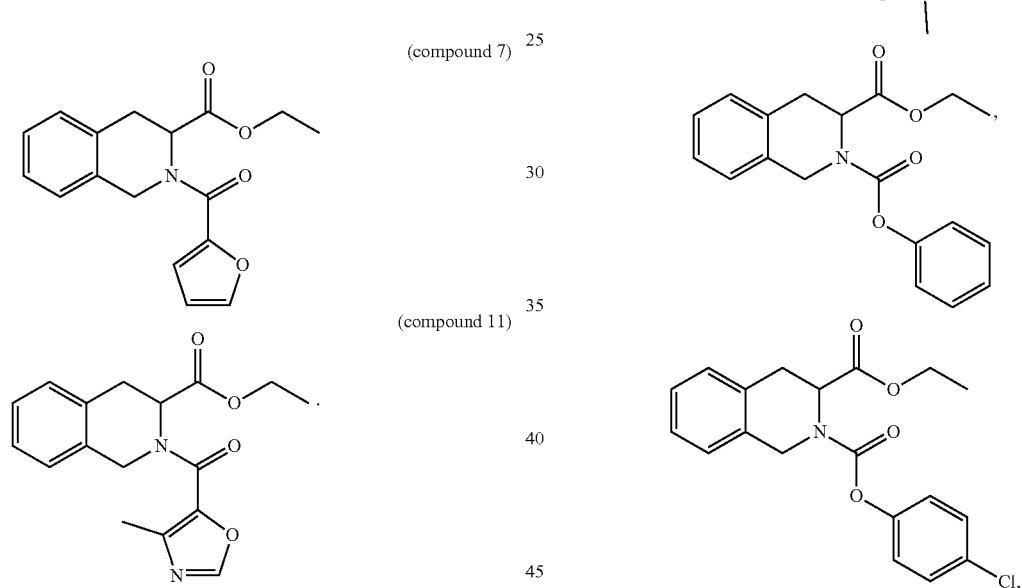

In some embodiments, the compound of formula (I) is also not disclosed in either WO 2013/033310 or WO 2015/103527. For instance, in relation to compounds per se of the present invention, the compound of formula (I) is not selected from:

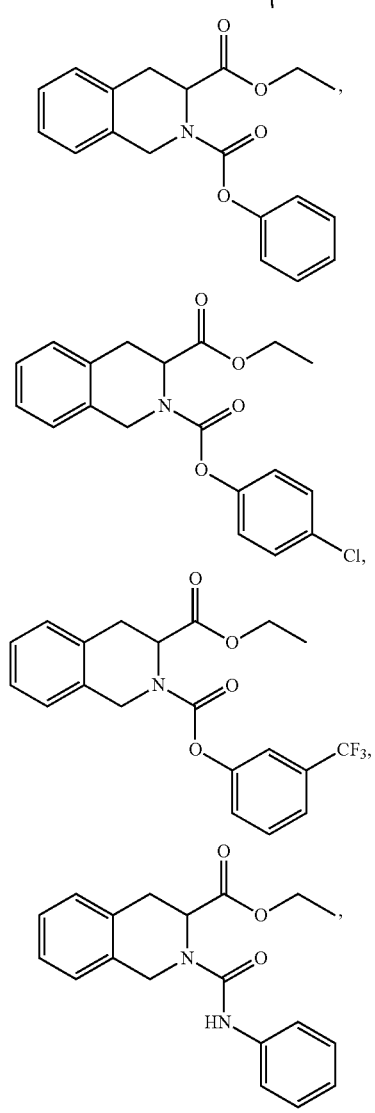

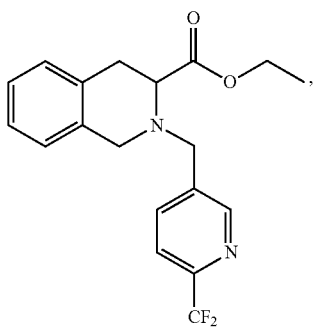
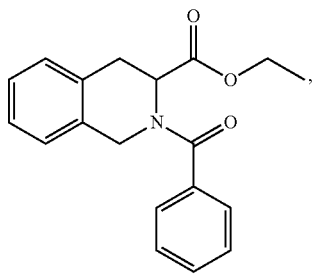
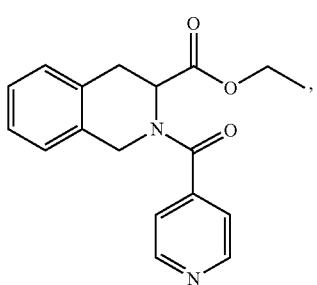
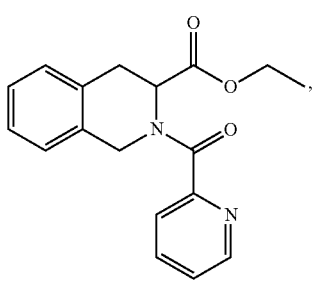
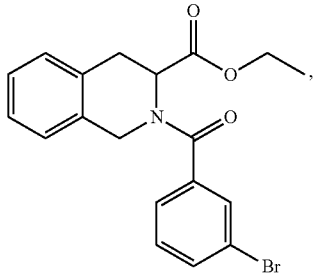
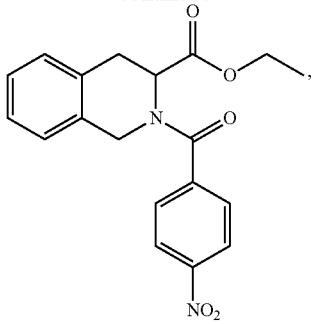
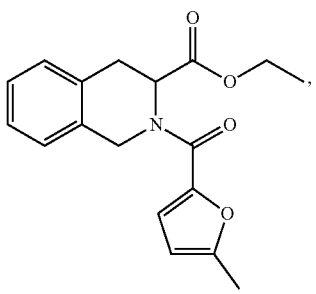
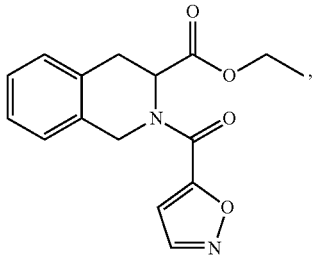
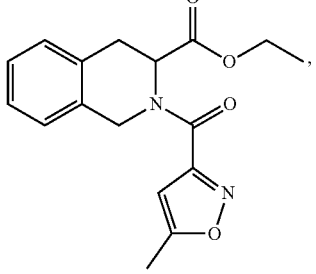
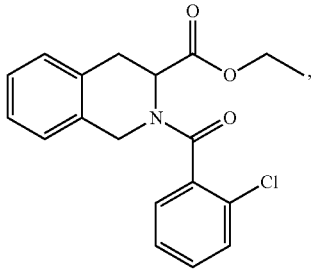
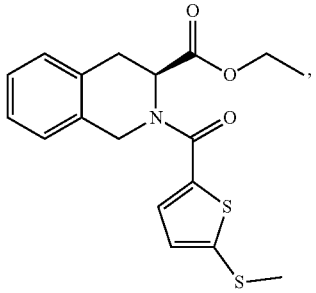

67
-continued
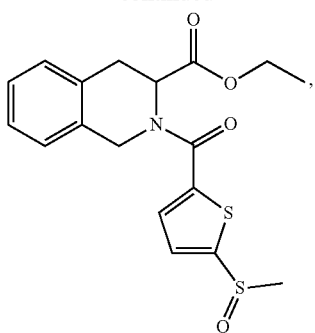
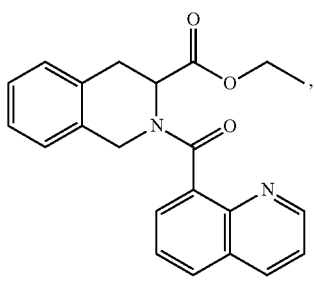
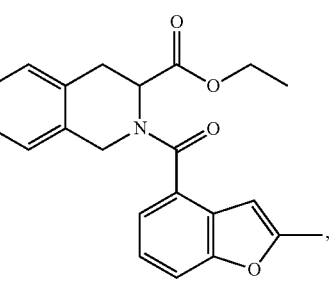
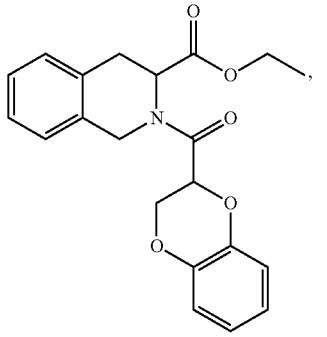
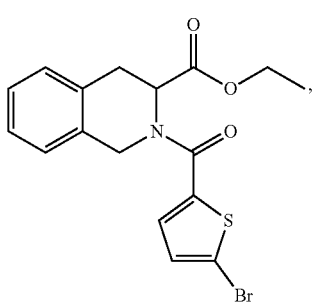
68
-continued
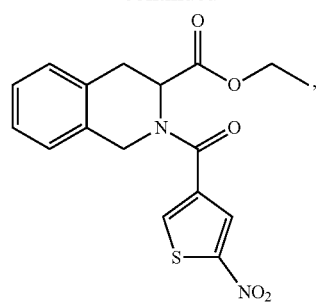
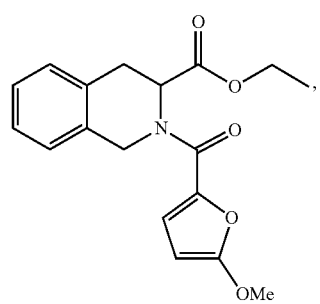 [SMILES: CCOC(=O)C1Cc2ccccc2CN1C(=O)c1ccc(SC)s1]
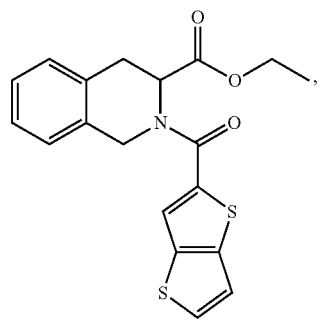
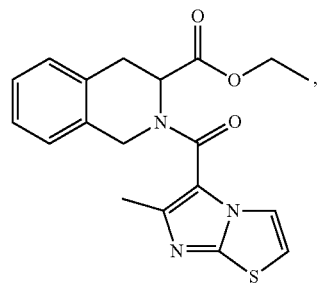
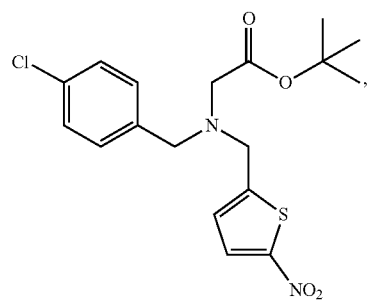

-continued
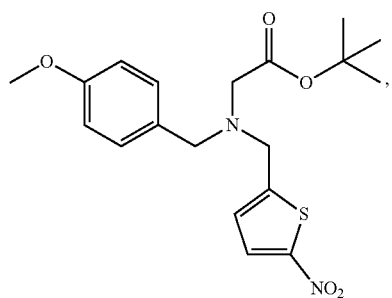
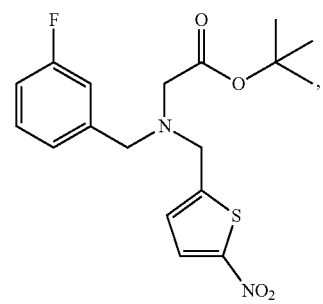
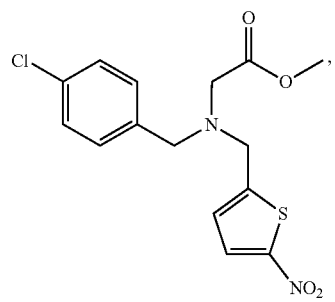
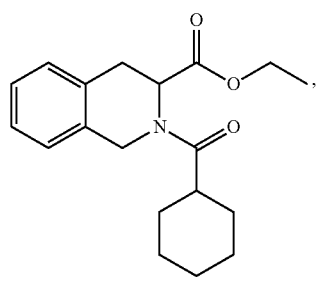
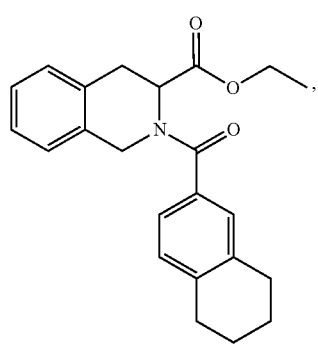
-continued
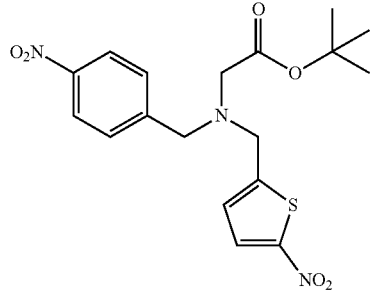
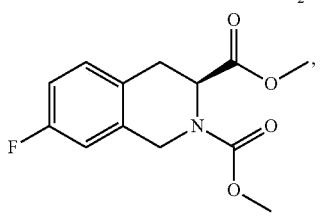
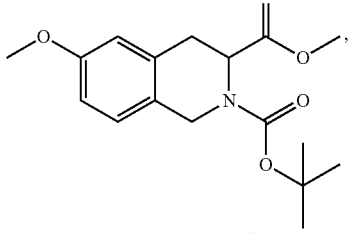
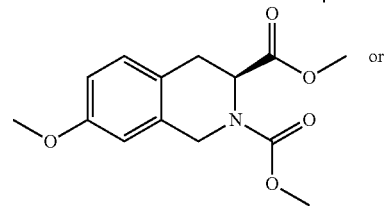
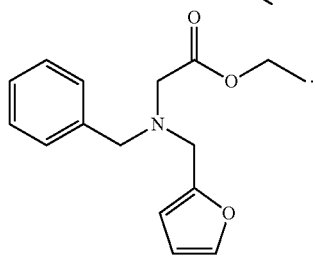
In some embodiments, and in relation to compounds per se of the present invention, the compound of formula (I) is not
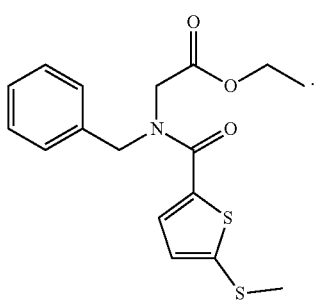 [SMILES: CCOC(=O)CN(Cc1ccccc1)C(=O)c1ccc(SC)s1]
Although the compounds per se identified above are not products of the present invention. These compounds may nevertheless be used in the methods and medical uses/ therapeutic indications described herein.

It will be understood that when compounds of the present invention contain one or more chiral centres, the compounds may exist in, and may be isolated as pure enantiomeric or diastereomeric forms or as racemic mixtures. The present invention therefore includes any possible enantiomers, diastereomers, racemates or mixtures thereof of the compounds of the invention. Thus, compounds of formula (I) may be used in a racemic mixture, or as single enantiomers, i.e.:

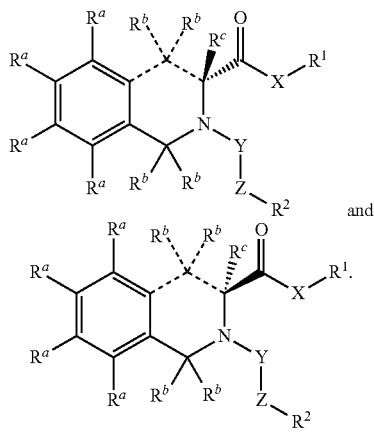

The compounds of formula (I) may have rotameric forms, or may not have rotational activity. Rotameric forms include slow rotating forms and fast rotating forms. In some preferred embodiments, fast rotating forms of the compounds of formula (I) are preferred. For example,

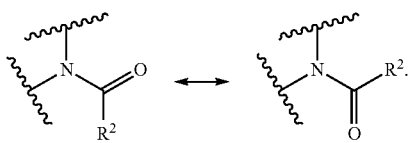

A compound of the formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. Thus, compounds of formula (I) according to the invention encompass tautomers (including keto-enol and amide-imidic acid forms).

Accordingly, a structure depicted herein as one tautomer is intended to also include the other tautomer.

Compounds may be used in the form of pro-drugs which convert into compounds of formula (I) in the body, as well as in salt, hydrate and solvate forms, as defined in the Definitions section herein.

The compounds of the present invention typically have improved REV-ERB inhibitory activity compared with SR8278. This inhibitory activity may be measured by any appropriate means, such as conventional means known in the art and/or the methods described herein. In the context of the present invention, a reference to a compound with improved REV-ERB inhibitory activity may be understood to mean that, the compound decreases REV-ERB activity by at least 10%, at least 20%, at least 30%, at least 40%, at least 50%, at least 60, at least 70%, at least 80%, at least 85%, at least 90%, at least 95%, at least 100%, at least 150%, at least 200% more than the decrease in REV-ERB activity obtained using a control REV-ERB inhibitory compound, such as SR8278. Typically REV-ERB activity is decreased by at least 40%, at least 50%, preferably at least 70%, more preferably at least 80%, even more preferably at least 90% or more compared with the decrease in REV-ERB activity obtained using a control REV-ERB inhibitory compound, such as SR8278.

A reference to a compound with improved REV-ERB inhibitory activity may be understood to mean that, said compound is at least 1.5-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 4-fold, at least 5-fold, at least 6-fold, at least 7-fold, at least 8-fold, at least 9-fold, at least 10-fold or more, more effective in inhibiting REV-ERB activity relative to a control REV-ERB inhibitory compound, such as SR8278. In other words, that the inhibition of REV-ERB by the improved REV-ERB antagonist is at least 1.5-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 4-fold or at least 5-fold or more greater than the inhibition in REV-ERB activity by a control REV-ERB inhibitory compound, such as SR8278. Typically an improved REV-ERB inhibitory compound is at least 1.5-fold, at least 2-fold or more effective in inhibiting REV-ERB activity relative to a control REV-ERB inhibitory compound, such as SR8278.

The small molecules of the invention may be used in the form of proteolysis targeting chimeras (also referred to as PROTACs or PROTAC reagents). PROTACs are heterobifunctional small molecules that simultaneously bind a target protein and ubiquitin ligase, enabling ubiquitination and degradation of the target. In more detail, a PROTAC reagent typically comprises a ligand for the target protein (in the case of the present invention, REV-ERB) and a ligand for an E3 ligase recognition domain. Through the use of such a PROTAC, an E3 ligase is recruited to the PROTAC-bound REV-ERB, inducing ubiquitin transfer from the E3 ligase complex to the target protein (in the case of the present invention, REV-ERB). Once the PROTAC has induced a sufficient degree of ubiquitination of the target, it is then recognised and degraded by the proteasome.

As a non-limiting example, a PROTAC reagent may be produced by conjugating a ligand for an E3-ligase to a small molecule inhibitor as described herein via a linker. In a preferred embodiment, a PROTAC reagent comprises a ligand for the E3 RING Cullin ligase von-Hippel Lindau protein (VHL) or cereblon—a part of a CRL4 E3 RING Cullin ligase complex, connected to a small molecule inhibitor of the invention via a linker.

Variant Sequences

A sequence identity of at least 80% includes at least 82%, at least 84%, at least 86%, at least 88%, at least 90%, at least 91%, at least 92%, at least 93%, at least 94%, at least 95%, at least 96%, at least 97%, at least 98%, at least 99%, and 100% sequence identity (to each and every sequence presented herein and/or to each and every SEQ ID NO presented herein).

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22 (22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262 (5131) Science 208-214 (1993); Align-M, see, e.g., Ivo Van Walle et al., Align-M—A New Algorithm for Multiple Alignment of Highly Divergent Sequences, 20 (9) Bioinformatics:1428-1435 (2004). Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992.

Variants of the specific sequences provided above may alternatively be defined by reciting the number of nucleotides or amino acids that differ between the variant sequences and the specific reference sequences provided above. Thus, in one embodiment, the sequence may comprise (or consist of) a nucleotide sequence that differs from the specific sequences provided above at no more than 5, no more than 4, no more than 3, no more than 2 nucleotide positions, for example at no more than 1 nucleotide position. Conservative substitutions are preferred.

Variant nucleic acid molecules and peptides as described herein typically still retain the activity of the corresponding molecules. Thus, for example, the variant REV-ERB molecules of the invention retain the ability of wild-type REV-ERB to inhibit the expression of E4bp4. The variant molecules may retain at least 50%, at least 60%, at least 70%, at least 80%, at least 90%, up to and including 100% of the activity of the corresponding wild-type sequences. This applies equally to any other variants as described herein.

The compounds of the invention may be labelled (or tagged). Any appropriate label may be used. Suitable labels are known in the art.

Notch Ligand

The Notch signalling pathway is primarily associated with promoting T cell development and repressing concomitant B cell development. Mammals have four types of Notch receptor—Notch1, Notch2, Notch3 and Notch4, all of which are single-pass heterodimeric transmembrane protein. Mammals have two types of canonical Notch ligands—Delta type and Jagged type, collectively known as DSL ligands. There are three delta-like ligands (DLLs), DLL1, DLL3 and DLL4 and two jagged (JAG) ligands, JAG1 and JAG2. DLL and JAG ligands typically comprise the following domains: a module at the N-terminus of Notch ligand (MNNL) domain and a Delta/Serrate/Lag-2 (DSL) domain, together with a number of EGF repeats. DLL3 comprises six EGF repeats. DLL1 and DLL4 comprise eight EGF repeats. JAG1 and JAG2 comprise 16 EGF repeats. There are also numerous non-canonical ligands, which may be membrane-bound or secreted.

Unless explicitly stated herein, a reference herein to a Notch ligand is a reference to any Notch ligand, such as a ligand of Notch1, Notch2, Notch3 and/or Notch 4, preferably a ligand of at least Notch1. The protein sequence of human Notch1 is given in SEQ ID NO: 10 (GenBank Accession No. CR457221, version CR457221.1). Typically the Notch ligand of use in the present invention is a canonical Notch ligand. In some preferred embodiments, the Notch ligand is a DLL, more preferably DLL4. The protein sequence of human DLL4 is given in SEQ ID NO: 8 (GenBank Accession No. AF253468, version AF253468.1).

A reference herein to a Notch ligand also embraces fragments thereof, provided said fragment retains the Notch-binding and activatory activity of the Notch ligand from which it is derived. Fragments of Notch ligands suitable for use in the present invention have previously been described by the present inventors (see PCT/GB2018/050818, which is herein incorporated by reference in its entirety, particularly pages 15 and 16 and the Examples). Preferred examples of Notch ligand fragments include Notch ligand (N-EGF1) and Notch ligand (N-EGF2), such as DLL4 (N-EGF1) and DLL4 (N-EGF2).

Alternatively or in addition, a Notch ligand, fragment thereof, or molecule that mimics the effect (e.g. function/activity) of a Notch ligand, such as DLL4 may comprise modifications, such as amino acid mutations which alter, typically increase, the affinity of the ligand/fragment/mimetic for its Notch receptor. Techniques for identifying such modifications are known in the art. For example, amino acids which increase the affinity of a Notch ligand/fragment/mimetic can be identified using yeast surface display. Again, such modifications have previously been described by the present inventors (see PCT/GB2018/050818, which is herein incorporated by reference in its entirety, particularly page 16). In some preferred embodiments, the DLL4 ligand of the invention, a fragment or mimetic thereof comprises the amino acid substitutions, G28S, F107L and L206P, more preferably G28S, F107L, N118I, I143F, H194Y, L206P and/or K215E.

As a further non-limiting example, a functional fragment of DLL4 comprises at least residues 65 to 114 and 179 to 219 of full-length DLL4, preferably held in the correct conformation to allow interaction with the Notch ligand.

In addition, the invention encompasses the use of molecules that would mimic the effect (e.g. activity/function) of a Notch ligand (also referred to herein as mimetics). For example, the use of peptides, stapled peptides, peptoids and peptidomimetics that would mimic the effect of the desired Notch ligand (such as DLL4) is embraced by the present invention. Peptidomimetics may have advantages over peptides in terms of stability and bioavailability associated with a natural peptide. Peptidomimetics can have main- or sidechain modifications of the parent peptide designed for biological function. Examples of classes of peptidomimetics include, but are not limited to, peptoids and β-peptides, as well as peptides incorporating D-amino acids.

Methods for producing synthetic peptides and peptidomimetics (such as peptoids) are known in the art, as are the sequences of canonical and non-canonical Notch ligands. Thus, it would be routine for one of skill in the art to produce suitable molecules which mimic the effect of a desired Notch ligand using known techniques and based on the known Notch ligand sequences. As a non-limiting example, peptidomimetics may be designed to interact with key residues of Notch (e.g. Notch1) that are known to be involved in binding to DLL4, such as one or more of residues 415 (E415), 418 (L418), 420 (A420), 421 (N421), 422 (P422), 424 (E424), 425 (H425), 436 (F436), 447 (P447), 448 (R448), 450 (E450), 452 (D452), 469 (D469), 477 (I477), 480 (P480) of Notch (Notch1), or any combination thereof.

The methods of the invention may encompass the use of any Notch ligand or fragment thereof which is capable of increasing NK cell production or molecule which mimics the effects thereof, particularly which may act synergistically with a compound of the invention which inhibits REV-ERB activity as disclosed herein, or a compound which results in the alteration of post-translational modification of E4bp4, and hence an increase in E4bp4 activity as disclosed herein.

The present inventors have previously shown that E4bp4 directly binds to the regulatory region of the Notch1 gene in vivo and so could enhance the transcriptional regulation of Notch, and that Notch1 expression E4bp4$^{-/-}$ mice is significantly reduced. Following on from this, the present inventors found that short-term exposure of Notch ligands to murine HSCs and very early progenitors can promote NK cell development, even in the absence of the critical transcription factor E4bp4. Further, the present inventors have shown that the Notch ligand Delta-like ligand 4 (DLL4) is particularly effective in stimulating the expansion of NK cells.

Accordingly, the present invention relates to the expansion of NK cells by exposure of the HPCs to a Notch ligand in combination with the use of a compound which inhibits the action of REV-ERB as described herein. In ex vivo or in vitro methods of the invention, this can comprise a step of culturing the HPCs in the presence of a Notch ligand. For in vivo methods, this may comprise administering the compound together with a Notch ligand. In preferred embodiments, the Notch ligand is DLL4, or a fragment or variant thereof which retains the function of DLL4.

Variant sequences are described herein in relation to REV-ERB. That disclosure applies, inter alia, equally and independently to variants of Notch ligands and fragments/mimetics thereof. The variant Notch ligands/fragments/mimetics of the invention typically at least retain the activity of the corresponding Notch ligands/fragments/mimetics of the invention. Thus, for example, the variant DLL4 ligands or fragments thereof of the invention retain the ability of the corresponding DLL4 molecules to bind to Notch1, and/or to enhance NK cell production. In some embodiments, the variant DLL4 ligands/fragments/mimetics have greater activity than the corresponding unmodified DLL4 ligand/fragment/mimetic. Such variants have previously been described by the present inventors (see PCT/GB2018/050818, which is herein incorporated by reference in its entirety, particularly pages 17 and 18). By way of non-limiting example, a Notch ligand/fragment/mimetic/variant thereof (e.g., a DLL4 ligands/fragments/mimetics/variant thereof) may have a $K_D$ value for binding to Notch1 of less than 1 μM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM or less, preferably less than 500 nM, less than 400 nM, less than 300 nM or less. In some embodiments, a variant Notch ligand/fragment/mimetic (e.g., a variant DLL4 ligands/fragments/mimetics) can increase the number of NK cells, or give rise to an increase in NK cell production, of at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 3 fold or more relative to the corresponding unmodified Notch ligand/fragment/mimetic. The variant Notch ligand/fragment/mimetic (e.g., variant DLL4 ligands/fragments/mimetics) may increase number of NK cells by at least 10%, at least 20%, at least 30%, at least 40%, at least 50%, at least 60, at least 70%, at least 80%, at least 85%, at least 90%, at least 95%, at least 100%, at least 150%, at least 200%, at least 300% or more compared with the corresponding unmodified DLL4 ligand/fragment/mimetic.

The Notch ligands/fragments/mimetics of the invention may be labelled (or tagged). Any appropriate label may be used. Suitable labels are known in the art.

Post-Translational Modification of E4bp4

The present inventors have previously shown that alteration of post-translational modification of E4bp4 can increase E4bp4 activity (see PCT/GB2018/050818, which is herein incorporated by reference in its entirety, particularly pages 33 to 36 and Examples 1 to 5). Furthermore, increasing E4bp4 activity by alteration of post-translational modification results in an increase in NK cell number (as defined herein).

Accordingly, methods of the present invention may further comprises a step of contacting an haematopoietic progenitor cell (HPC) comprising sample obtained from an individual/patient with a compound which results in the alteration of post-translational modification of E4bp4, thereby causing an increase in E4bp4 activity. Thus, compounds which alter the post-translational modification of E4pb4 as described herein may be used in combination with the methods and compounds of the invention which inhibit REV-ERB activity. This combination may further be used in combination with the use of a Notch ligand (e.g. DLL4) as described herein.

Similarly, a compound which alters or affects the post-translational modification of E4bp4 may therefore be used according to the invention for increasing production of NK cells in a patient, wherein said compound increases E4bp4 activity, or for use in a method of treatment by increasing the number of NK cells in a patient in need thereof, together with the indications disclosed herein relating to increased E4bp4 expression by decreasing REV-ERB activity, and optionally the indications disclosed herein relating to increasing NK cell number by culturing HPCs in the presence of a Notch ligand.

Any of the disclosure herein in relation to methods of increasing NK cell number, methods of expanding NK cells in the context of compounds which inhibit the action of REV-ERB, and/or Notch ligands, expanded NK cell populations produced by said methods and therapeutic indications relating to said compounds and populations applies inter alia to the disclosed methods of increasing E4bp4 activity to increase NK cell number. As non-limiting examples, the feeder cell layers, growth factors and/or other culture conditions and diseases to be treated may be the same in relation to the post-translational modification aspects as for the REV-ERB inhibition and/or Notch ligand aspects disclosed herein. The REV-ERB inhibitor compound, Notch ligand and/or E4bp4 post-translational modifier may be used simultaneously, separately or sequentially. When a compound which alters the post-translational modification of E4bp4 is used in combination with a compound which inhibits the action of REV-ERB, typically the sample is contacted with REV-ERB inhibitory compound before being contacted with the post-translational modifier. If a Notch ligand is also used, typically the E4bp4 post-translational modifier is used after the REV-ERB inhibitory compound and the Notch ligand; preferably the REV-ERB inhibitory compound are used together, or more preferably the REV-ERB inhibitory compound is used before the Notch ligand (as described herein).

Types of Post-Translational Modification

Said method encompasses any alteration of post-translational modification which results in an increase in E4bp4 activity. Non-limiting examples of post-translation modification include phosphorylation, SUMOylation, the addition of a hydrophobic group (e.g. myristoylation, palmitoylation), addition of a cofactor, the addition of small chemical groups (e.g. acylation, alkylation, amidation, glycosylation), glycation, carbamylation, cabonylation, chemical modifications (e.g. deamidation) and/or structural changes. Typically alteration of post-translational modification according to the invention results in a reduction in phosphorylation at one or more phosphorylation site within wild-type (unmodified) E4bp4 and/or a reduction in SUMOylation at one or more SUMOylation site within wild-type (unmodified) E4bp4, or a combination thereof. As previously shown by the inventors (see PCT/GB2018/050818, which is herein incorporated by reference in its entirety, particularly pages 33 to 36 and Examples 1 to 5), wild-type (unmodified) E4bp4 is typically SUMOylated at one or more of residues K10, K116, K219, K337 and/or K394 or residues corresponding thereto, or any combination thereof. Typically wild-type (unmodified) E4bp4 is SUMOylated at least at residue K219 (or a corresponding residue). Alternatively or in addition, wild-type (unmodified) E4bp4 is typically phosphorylated at residues S286, S301 and S454, or residues corresponding thereto, or any combination thereof. Accordingly, in some embodiments, a compound which alters the post-translational modification of E4bp4 reduces, inhibits or ablates SUMOylation at residue K219 (or a residue corresponding thereto), and/or reduces, inhibits or ablates phosphorylation at residues 5286, S301 and S454 (or corresponding residues), or any combination thereof. Thus, according to the present invention, a compound may be used to (a) reduce SUMOylation at one or more of residues K10, K116, K219, K337 and/or K394 of E4bp4, or a residue corresponding thereto, or any combination thereof; and/or reduce phosphorylation at one or more of residues S286, S301 and/or S454, or a residue corresponding thereto, or any combination thereof.

Any compound which is capable of altering or affecting the post-translational modification of E4bp4, wherein said alteration increases the activity of E4bp4 may be used according to the present invention. In some embodiments, said compound inhibits, reduces or ablates the phosphorylation and/or SUMOylation that occurs in wild-type (unmodified) E4bp4. Any appropriate kinase inhibitor may be used to inhibit, reduce or ablate phosphorylation of E4bp4. Suitable kinase inhibitors are known in the art and their selection would be routine to one of skill in the art. For example, based on current understanding of kinases which phosphorylate E4bp4, it may be appropriate to use inhibitors of phosphoinositide-dependent protein kinase-1 (PDK1) and/or casein kinase 1epsilon (CK1epsilon). Non-limiting examples of suitable kinase inhibitors include 4-(4-(2,3-Dihydrobenzo[1,4]dioxin-6-yl)-5-pyridin-2-yl-1H-imidazol-2-yl)benzamide (D4476) and 4,5,6,7-Tetrabromo-2-azabenzimidazole, 4,5,6,7-Tetrabromobenzotriazole (TBB).

Increase in E4bp4 Activity

An increase in E4bp4 activity (e.g. as brought about by post-translational modification of E4bp4) may be measured relative to a control. Thus, the activity of E4bp4 in a sample of NK precursor or progenitor cells, an expanded NK cell population or in a sample obtained from an individual/patient to be treated according to the invention may be compared with the activity of E4bp4 in a control. Activity may be quantified in any appropriate terms, for example an increase in the expression of any downstream target of E4bp4. Any appropriate technique or method may be used for quantifying E4bp4 activity. Suitable techniques are known in the art, for example luciferase assays for quantifying expression of a reporter gene.

Typically the control is an equivalent population or sample which has not been treated according to the present invention. For example, in instances where a compound is used to alter or affect the post-translational modification of E4bp4, the corresponding control may be a population or sample in which no compound has been added to alter or affect the post-translational modification of E4bp4. As another example, in instances where a compound is used to inhibit the action of REV-ERB, the corresponding control may be a population or sample in which no compound has been added to inhibit the action of REV-ERB. As another example, in instances where a compound is used to inhibit the action of REV-ERB and a compound is used to alter or effect the post-translational modification of E4bp4, the corresponding control may be a population or sample in which no compound has been added to inhibit the action of REV-ERB or to alter or effect the post-translational modification of E4bp4.

A control may be a sample obtained from a different individual treated according to the invention, or the same individual the prior to treatment. Conventional methods for the ex vivo expansion of NK cells, including known methods may be considered control methods according to the present invention.

In the context of the present invention, a reference to increasing E4bp4 activity may be understood to mean that, the activity of E4bp4 is increased by at least 1.5-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 4-fold, at least 5-fold, at least 6-fold, at least 7-fold, at least 8-fold, at least 9-fold, at least 10-fold or more relative to a control. Typically E4bp4 activity is increased by at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, or more compared with the control. E4bp4 activity may be measured indirectly be determining the increase in NK cell number. Thus, the number of NK cells may be increased by at least 1.5-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 4-fold, at least 5-fold, at least 6-fold, at least 7-fold, at least 8-fold, at least 9-fold, at least 10-fold or more relative to a control. Typically the number of NK cells is increased by at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, or more compared with the control.

The activity of E4bp4 may be determined by quantitative and/or qualitative analysis, and may be measured directly or indirectly. The activity of E4bp4 relative to a control may be determined using any appropriate technique. Suitable standard techniques are known in the art.

The activity of E4bp4 may be increased compared with a control for at least 6 hours, at least 12 hours, at least 24 hours, at least 30 hours, at least 36 hours, at least 42 hours, at least 48 hours, at least 54 hours, at least 60 hours, at least 72 hours, at least 4 days, at least 5 days, at least 6 days, at least 1 week. Preferably, the activity of E4bp4 is increased for at least 12 to 72 hours. Typically this is assessed relative to the last administration of the compound which post-translationally modified E4bp4.

The activity of E4bp4 may be increased compared with a control for at least one, at least two, at least three, at least four, at least five, at least ten, at least 20, at least 30, at least 40 or more passages of the cultured cells. The activity of E4bp4 may be increased indefinitely.

Methods of Expanding NK Cells

The present invention relates to a method for expanding an NK cell population. Said method may be in vitro, in vivo or ex vivo. Said method comprises containing HPCs with a compound that inhibits the action of REV-ERB (as described herein) and expanding said cells to produce an NK cell population. The methods of the invention allow for the rapid expansion of NK cells, reducing the time needed for their culture, and hence the risk of exhaustion, enhancing the cytotoxicity of the NK cells when transfused into a patient.

When said method is carried out in vivo, said method is a therapeutic method as described herein. In such embodiments, all the disclosure herein in relation to therapeutic indications and applications of the invention is applicable to said methods.

Typically the method of the invention is ex vivo. Accordingly, the invention provides an ex vivo method for expanding an NK cell population comprising the steps of: (a) culturing an NK precursor cell comprising sample obtained from an individual; (b) contacting said sample with a compound that inhibits the action of REV-ERB; and (c) expanding said cells in vitro to produce an NK cell population. The compound may be any REV-ERB inhibitory compound of the invention as described herein. Typically said compound increases E4bp4 expression by decreasing REV-ERB activity as described herein. In a preferred embodiment, the compound has the formula (II) as defined herein, more preferably the compound has the formula (III) as defined herein, even more preferably the compound has the formula (IV) as defined herein, and even more preferably, the compound has the formula (V) as defined herein. Examples of specific compounds which may be used in the methods of the invention are described herein, with compounds 7 and 11 being particularly preferred.

Additional external stimuli, such as growth factors and/or cytokines, may be used to further enhance the production of NK cells. Non-limiting examples of suitable external stimuli include IL-7, IL-15, Flt3L, stem cell factor (SCF), thrombopoietin (TPO), IL-3 and/or IL-6, or any combination thereof. In some preferred embodiments, IL-7, Flt3L and/or SCF, or any combination thereof is used. More preferably IL-7, Flt3L and SCF are used.

As a non-limiting example, IL-7 may be used at a concentration of about 1 ng/ml to about 100 ng/ml, about 1 ng/ml to about 50 ng/ml, about 1 ng/ml to about 25 ng/ml, about 1 ng/ml to about 10 ng/ml or less. In some embodiments IL-7 is used at a concentration of about 50 ng/ml, about 25 ng/ml, about 20 ng/ml, about 15 ng/ml, about 10 ng/ml or about 5 ng/ml, preferably about 10 ng/ml. As a non-limiting example, Flt3L may be used at a concentration of about 1 ng/ml to about 100 ng/ml, about 1 ng/ml to about 50 ng/ml, about 1 ng/ml to about 25 ng/ml, about 1 ng/ml to about 10 ng/ml or less. In some embodiments Flt3L is used at a concentration of about 50 ng/ml, about 25 ng/ml, about 20 ng/ml, about 15 ng/ml, about 10 ng/ml or about 5 ng/ml, preferably about 10 ng/ml. As a non-limiting example, SCF may be used at a concentration of about 1 ng/ml to about 200 ng/ml, about 1 ng/ml to about 150 ng/ml, about 1 ng/ml to about 100 ng/ml, about 1 ng/ml to about 50 ng/ml or less. In some embodiments SCF is used at a concentration of about 150 ng/ml, about 125 ng/ml, about 120 ng/ml, about 110 ng/ml, about 100 ng/ml, about 90 ng/ml, about 80 ng/ml or about 75 ng/ml, preferably about 100 ng/ml.

As a non-limiting example, IL-15 may be used at a concentration of about 1 ng/ml to about 100 ng/ml, about 1 ng/ml to about 50 ng/ml, about 1 ng/ml to about 40 ng/ml, about 1 ng/ml to about 30 ng/ml, about 1 ng/ml to about 20 ng/ml, about 1 ng/ml to about 10 ng/ml or less. In some embodiments IL-15 is used at a concentration of about 50 ng/ml, about 40 ng/ml, about 35 ng/ml, about 30 ng/ml, about 25 ng/ml, about 20 ng/ml or about 10 ng/ml, preferably about 30 ng/ml.

Alternatively or in addition, the HPCs may be cultured on or with suitable support/stromal cells or cell layer. Any appropriate stromal cell may be used, including, but not limited to OP9 stromal cells and/or EL08-1D2 stromal cells.

In some embodiments, the ex vivo method comprises a single stage in which the HPCs in a sample obtained from a patient are cultured, contacted with a compound of the invention and expanded to form an NK cell population, typically under substantially constant culture conditions. Typically this involves incubating the HPCs with factors such as IL-3, IL-7, SCF, Flt3L and/or IL-15, preferably all of these factors. The HPCs are preferably also cultured on or with stromal cells/cell layer, such as EL08-1D2 stromal cells.

In some embodiments, the ex vivo method comprises two stages. The first is a lymphoid production stage, in which the HPCs in a sample obtained from a patient are cultured. Typically this involves incubating the HPCs with cytokines and growth factors associated with lymphoid production, such as Flt3L, IL-7 and/or SCF. This stage may last for at least one, at least two, at least three, at least four, or more days. In some preferred embodiments, this stage lasts for two days. The second stage of the ex vivo method is a stage of NK cell expansion. Typically this involves transferring the cultured HSCs to a suitable stromal (support) cell layer, such as OP9 stromal cells and culturing in cytokines and growth factors associated with NK cell development, such as IL-15. A compound of the invention is typically added during this second stage, and preferably at the start of this second stage. The second stage lasts for the remainder of the ex vivo culture period (as defined above). The culture medium may be changed as often as required during this second stage in order to facilitate NK cell expansion. This second stay may last for at least one, at least two, at least three, at least four, at least five, at least six, at least seven, at least eight, at least nine, at least ten, at least 11, at least 12, at least 13, at least 14 or more days. In some preferred embodiments, this stage lasts for at least one week.

The HPC comprising sample may be cultured ex vivo for at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days or more. Typically said sample is cultured for at least 9 days in order to produce an expanded NK cell population. These culture periods are for the total culture period of the ex vivo method, i.e. if there are two stages, these periods are for the total (stage 1 plus stage 2). An example culture scheme for HPCs for the production of NK cells is set out in FIG. 2A.

The REV-ERB inhibitor compound of the invention may be added to the sample comprising HPCs within one week, within six days, within five days, within four days, within three days, within two days, within one day of isolating the HPCs in the sample, or on the same day as isolating the NK cell precursors. Typically this is the same day that the sample is obtained from the patient. Preferably the compound of the invention is added to the sample within two days of isolating the HPCs in the sample, even more preferably on day two following isolation of the HPCs. In some embodiments the compound is added at multiple time points, for example when the culture medium is changed. As a non-limiting example, the compound of the invention may be added two days after isolating the HPCs, and then added again at day five post-isolation of the HPCs. This disclosure applies to all methods of the invention, e.g. for one stage and two stage methods as described herein, and/or methods which also use a Notch ligand and/or a compound which alters the post-translational modification of E4bp4 as described herein.

Any appropriate concentration of a compound of the invention may be used, provided that it inhibits the action of REV-ERB as described herein and has utility in expanding an NK cell population. As a non-limiting example, in any aspect of the invention, a compound of the invention may be used at a final concentration of about 2 to about 20 µM, about 2 to about 15 µM, about 5 to about 15 µM, about 5 to about 14 µM, about 4 to about 13 µM, about 5 to about 12 µM, about 5 to about 11 µM, or preferably about 5 to about 10 µM.

The present inventors have previously demonstrated that combining the use of a Notch ligand (such as DLL4) and REV-ERB inhibition results in a potent means for enhancing NK cell production, allowing for the production of large numbers of functional NK cells that are suitable for in vivo therapeutic use more rapidly than the current methods.

Thus, the invention provides an ex vivo method for expanding an NK cell population comprising the steps of: (a) culturing an HPC comprising sample obtained from an individual/patient with a compound that inhibits the action of REV-ERB (as described herein); (b) culturing said cells in the presence of a Notch ligand (such as DLL4); and (c) expanding said cells in vitro to produce an NK cell population. Step (a) and (b) may be carried out concurrently or in any order. For example, step (a) may be carried out first, followed by step (b), such that the cells are first exposed to a REV-ERB inhibitory compound and then cultured in the presence of a Notch ligand. Alternatively, step (b) may be carried out first, followed by step (a), such that the cells are first cultured in the presence of a Notch ligand and then in the presence of a REV-ERB inhibitory compound. Alternatively, steps (a) and (b) may be carried out concurrently, such that the cells are simultaneously cultured in the presence of a REV-ERB inhibitory compound and a Notch ligand.

In some preferred embodiments, step (a) may be carried out first, followed by step (b), such that the cells are first cultured in the presence of a REV-ERB inhibitory compound and then in the presence of a Notch ligand. Thus, in those embodiments the invention provides an ex vivo method for expanding an NK cell population comprising the steps of: (a) culturing an HPC comprising sample obtained from an individual/patient with a compound that inhibits the action of REV-ERB (as described herein); (b) culturing said cells in the presence of a Notch ligand (such as DLL4); and (c) expanding said cells in vitro to produce an NK cell population.

Typically the Notch ligand is a Notch ligand as described herein. Preferably, the Notch ligand is DDL4, or a fragment thereof which retains the function of DLL4, as described herein.

The Notch ligand (such as DLL4) may be present in solution (e.g. in the culture medium) or used to coat the vessel in which the HPCs are cultured. Preferably the Notch ligand (e.g. DLL4) is used to coat the vessel in which the HPCs are cultured. As a non-limiting example, in any aspect of the invention where a Notch ligand is used, the Notch ligand (e.g. DLL4) may be used at a concentration of about 1 µg/ml to about 100 µg/ml, about 1 µg/ml to about 50 µg/ml, about 1 µg/ml to about 25 µg/ml, about 1 µg/ml to about 10 µg/ml or less. In some embodiments the Notch ligand (e.g. DLL4) is used at a concentration of about 50 µg/ml, about 25 µg/ml, about 20 µg/ml, about 15 µg/ml, about 10 µg/ml, or about 5 µg/ml, preferably about 10 µg/ml. Additional substrates and/or linkers may be used to facilitate the attachment of the Notch ligand (such as DLL4) to the surface of the culture vessels. Examples of such substrates are known in the art, such as poly-L-lysine.

As described above, HPCs may be cultured in the presence or absence of a stromal support cell or feeder cell, or population thereof. In some preferred embodiments where a Notch ligand is used, the cells are cultured in the absence of a stromal support cell or population thereof.

In some embodiments, the ex vivo method comprises a single stage in which the HPCs in a sample obtained from an individual/patient are cultured, contacted with a compound of the invention and a Notch ligand and expanded to form an NK cell population, typically under substantially constant culture conditions (i.e. steps (a) and (b) of the method are carried out concurrently). Typically this involves incubating the HPCs with factors such as IL-3, IL-7, SCF, Flt3L and/or IL-15, preferably all of these factors. The HPCs may be cultured in the presence or absence of stromal cells/cell layer, such as EL08-1D2 stromal cells.

Figure 2:
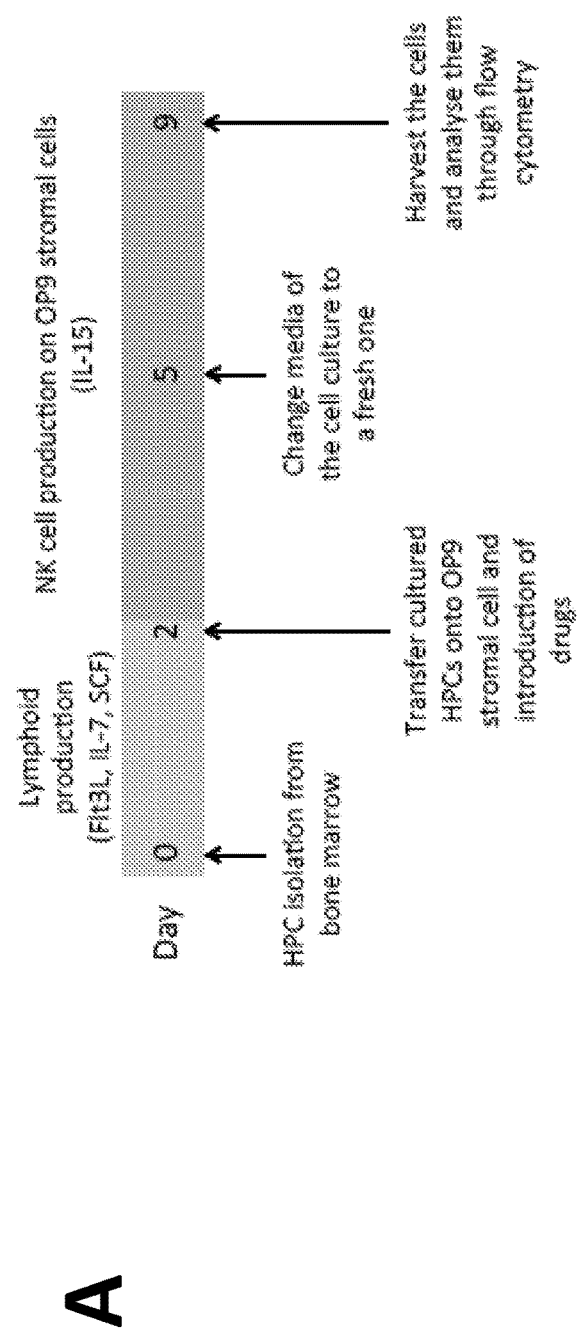
FIG. 2: (A) Timeline of example one-stage NK cell expansion method. HPCs may be isolated and cultured plus Flt3L, IL-7 and SCF cytokines. At Day 2, they may then transferred onto OP9 stromal cells plus or minus REV-ERB inhibitor compound in culture medium, optionally plus the IL-15 cytokine. (B) Schematic representation of example two-stage culture of NK cell development using a REV-ERB inhibitory compound and a Notch ligand.
Figure 2:
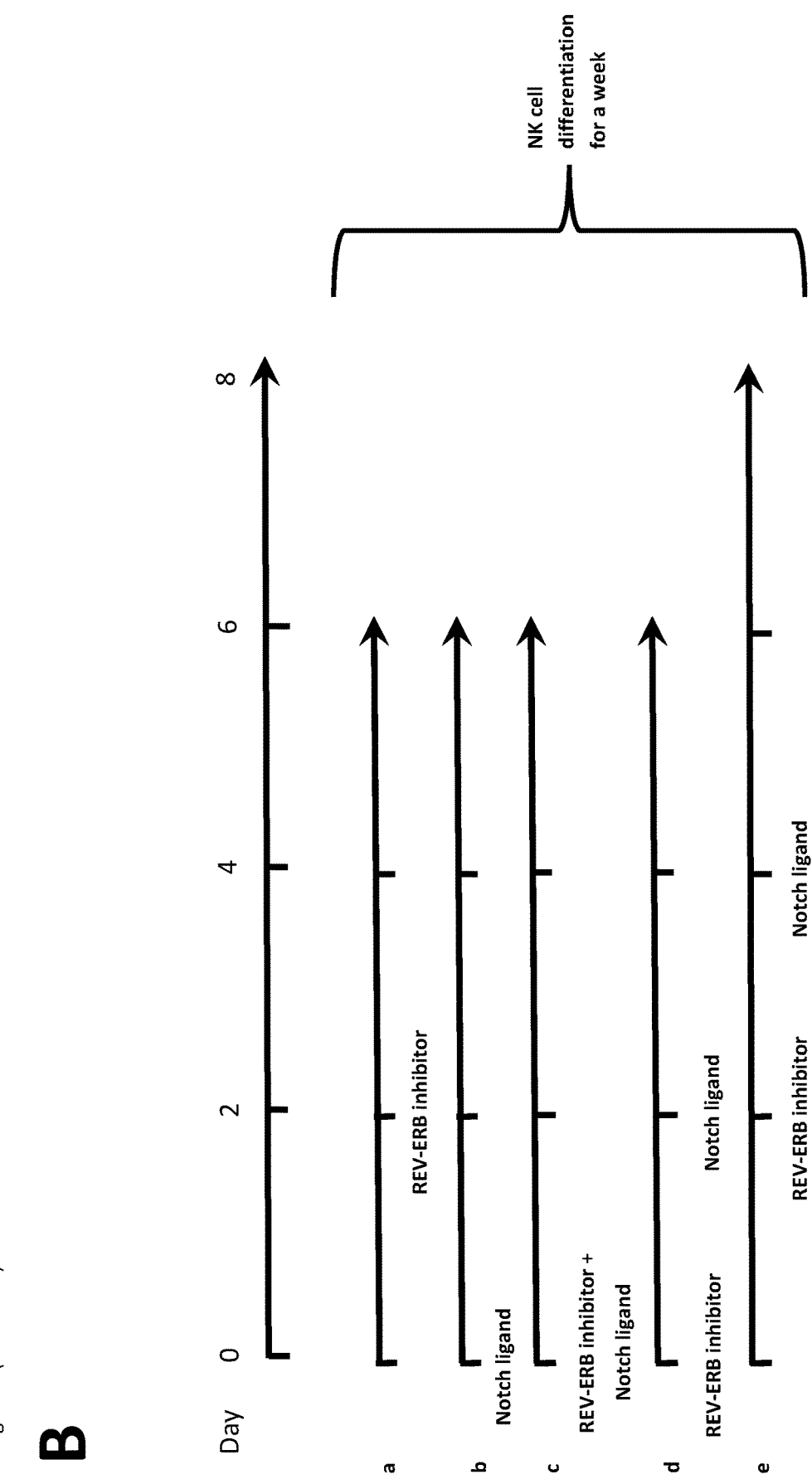

In some embodiments, the ex vivo method comprises two stages (analogous to the scheme shown in FIG. 2). The first is a lymphoid production stage, in which the HPCs in a sample obtained from an individual/patient are cultured. Typically this involves incubating the HPCs with cytokines and growth factors associated with lymphoid production, such as Flt3L, IL-7 and/or SCF. This stage may last for at least one, at least two, at least three, at least four, or more days. In some preferred embodiments, this stage lasts for two days.

This is followed by a stage of NK cell expansion. Typically this involves culturing the cells in cytokines and growth factors associated with NK cell development, such as IL-15, and may involve transferring the cultured HSCs to a suitable stromal (support) cell layer, such as OP9 stromal cells. The second stage lasts for the remainder of the ex vivo culture period (as defined herein). The culture medium may be changed as often as required during this second stage in order to facilitate NK cell expansion. Any REV-ERB inhibitory compounds, Notch ligands and/or compounds which alter the posttranslational modification of E4bp4 that are present in the culture medium before it is replaced may be administered again with the fresh culture medium, either at the same or different concentration. As a non-limiting example, if a compound of the invention is added two days after isolating the HPCs, and the medium changed at day five post-isolation of the HPCs, the compound may be administered again at day 5 post-isolation with the fresh medium.

In some embodiments, the REV-ERB inhibitory compound of the invention is added in stage 1 (lymphoid production) and the Notch ligand in the second stage (NK cell expansion). In other embodiments, the Notch ligand is added in stage 1 (lymphoid production) and the REV-EB inhibitory compound in the second stage (NK cell expansion). In yet other embodiments, both the REV-ERB inhibitory compound and the Notch ligand added in the first stage (lymphoid production). In further embodiments, both the REV-ERB inhibitory compound and the Notch ligand added in the second (NK cell expansion phase). If the REV-ERB inhibitory compound and the Notch ligand added in the same stage (either stage 1 or stage 2), that stage may be further divided so that: (i) the REV-ERB inhibitory compound is added before the Notch ligand; or (ii) the Notch ligand is added before the REV-ERB inhibitory compound. Alternatively, the Notch ligand and REV-ERB inhibitory compound may be added simultaneously in the same stage. FIG. 2B illustrates some embodiments of the different method schemes for the REV-ERB inhibitory compound and Notch ligand combination aspects of the invention. The timings of administration included in FIG. 2B are non-limiting; any appropriate timings for administration, such as those described herein, may be used. In some preferred embodiments the REV-ERB inhibitor is added in stage 1 (e.g. at day 0 or on day 2), with the Notch ligand being added later (e.g. at day 2 or 4 respectively).

Typically the REV-ERB inhibitory compound is added during the first stage, and the Notch ligand is added during the second stage, and preferably at the start of this second stage.

The HPC comprising sample may be cultured ex vivo for at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days or more. Typically said sample is cultured for at least 9 days in order to produce an expanded NK cell population. These culture periods are for the total culture period of the ex vivo method, i.e. if there are two stages, these periods are for the total (stage 1 plus stage 2).

The REV-ERB inhibitory compound of the invention may be added to the sample comprising HPCs within one week, within six days, within five days, within four days, within three days, within two days, within one day of isolating the HPCs in the sample, or on the same day as isolating the NK cell precursors. Typically this is the same day that the sample is obtained from the patient. Preferably the REV-ERB inhibitory compound of the invention is added to the sample within two days of isolating the HPCs in the sample, such as on the day of isolation of the HPCs. Most preferably the REV-ERB inhibitory compound of the invention is added to the sample two days post isolation of the HPCs. In some embodiments the compound is added at multiple time points, for example when the culture medium is changed. As a non-limiting example, the compound of the invention may be added two days after isolating the HPCs, and then added again at day five post-isolation of the HPCs.

The Notch ligand of the invention may be added to the sample comprising HPCs within one week, within six days, within five days, within four days, within three days, within two days, within one day of isolating the HPCs in the sample, or on the same day as isolating the NK cell precursors. Typically this is the same day that the sample is obtained from the patient. Preferably the Notch ligand of the invention is added to the sample within four days of isolating the HPCs in the sample, such as on day two following isolation of the HPCs. Most preferably the Notch ligand of the invention is added to the sample two or four days post isolation of the HPCs. Thus, typically the Notch ligand is present on or from 4 days after isolating the HPCs.

Preferred embodiments of the invention comprise (i) adding the REV-ERB inhibitory compound and the Notch ligand to the sample on the day of isolation of the HPCs; (ii) adding the REV-ERB inhibitory compound to the sample on the day of isolation of the HPCs and adding the Notch ligand to the sample on day two post isolation of the HPCs; or (iii) adding the REV-ERB inhibitory compound to the sample on day two post isolation of the HPCs and adding the Notch ligand to the sample on day four post isolation of the HPCs; with option (iii) being particularly preferred. As demonstrated previously by the inventors, these particular conditions maximise the synergy between the REV-ERB inhibition and the Notch ligand, and hence maximising the expansion of NK cells.

Additionally, the cells may be cultured in the presence of additional external stimuli (as described herein) in combination with a Notch ligand. As a non-limiting example, a Notch ligand may be used with IL-15. For example, the cells may be first exposed to a Notch ligand and then IL-15. Alternatively, the cells may first be cultured in the presence of IL-15 and then in the presence of a Notch ligand. Alternatively, the cells may be simultaneously cultured in the presence of a Notch ligand and IL-15. Preferably the cells are first cultured in the presence of a Notch ligand and then IL-15.

The HPCs may be cultured in the presence of a Notch ligand (such as DLL4) for at least 6 hours, at least 12 hours, at least 24 hours, at least 30 hours, at least 36 hours, at least 42 hours, at least 48 hours, at least 54 hours, at least 60 hours, at least 72 hours, at least 4 days, at least 5 days, at least 6 days, at least 1 week. Typically for 72 hours to 1 week. The cells may be cultured in the presence of IL-15 for at least 6 hours, at least 12 hours, at least 24 hours, at least 30 hours, at least 36 hours, at least 42 hours, at least 48 hours, at least 54 hours, at least 60 hours, at least 72 hours, at least 4 days, at least 5 days, at least 6 days, at least 1 week, at least 2 weeks, at least 3 weeks or longer, until the desired number of NK cells is produced. For example, the step of culturing in ||-15 may be is 1 week or more in length, 7 to 9 days in length, or about two weeks in length.

Alternatively, these durations may be measured in terms of the number of cell passages. For example, at least one, at least two, at least three, at least four, at least five, at least ten, at least 20, at least 30, at least 40 or more passages of the cells (either in vivo, or cultured ex vivo or in vitro).

The durations of exposure to Notch ligand and IL-15 are independent, and any duration for Notch culture may be used in combination with any duration of IL-15 culture. In some preferred embodiments, Notch exposure/culture is 72 hours to 1 week in length and IL-15 exposure/culture is 1 week (or more) in length.

Typically IL-7, Flt3L and/or SCF are used together with the Notch ligand. In some preferred embodiments, the HPCs are cultured in the presence of IL-7, Flt3L and SCF together with the Notch ligand.

The methods of the invention (both those including and excluding a step of contacting the HPCs with a Notch ligand) may further comprise a step of contacting the HPCs with a compound which results in the alteration of post-translational modification of E4bp4, thereby causing an increase in E4bp4 activity, as described herein. Optionally the alteration of post-translational modification of E4bp4 is a reduction in SUMOylation and/or phosphorylation of E4bp4 as described herein. In some preferred embodiments the compound which results in the alteration of post-translational modification of E4bp4: reduces SUMOylation at one or more of residues K10, K116, K219, K337 and/or K394 of E4bp4, or a residue corresponding thereto, or any combination thereof; and/or reduces phosphorylation at one or more of residues S286, S301 and/or S454 of E4bp4, or a residue corresponding thereto, or any combination thereof.

Any appropriate concentration of a compound which results in the alteration of post-translational modification of E4bp4 may be used, provided that it increases the activity of E4bp4 as described herein and has utility in expanding an NK cell population. As a non-limiting example, in any aspect of the invention, a compound which results in the alteration of post-translational modification of E4bp4 may be used at a final concentration of about 0.1 to about 20 µM, about 0.1 to about 15 µM, about 0.5 to about 15 µM, about 0.5 to about 14 µM, about 0.5 to about 12 µM, about 0.5 to about 11 µM, or about 0.5 to about 10 µM, such as from about 5 to about 10 µM. In some preferred embodiments, a compound which results in the alteration of post-translational modification of E4bp4 may be used at a final concentration of about 0.5 to about 5 µM, more preferably of about 0.5 to about 2 µM, even more preferable of about 0.5 to about 1 µM.

The REV-ERB inhibitor compound, Notch ligand and/or compound which alters E4bp4 post-translational modification may be used simultaneously, separately or sequentially as described herein.

Each of the REV-ERB inhibitor compound, Notch ligand and/or compound which alters E4bp4 post-translational modification may independently be used as a single treatment or application or in multiple treatments or applications (in both in vitro, ex vivo or in vivo methods as described herein). For multiple applications, at least two, at least three, at least four, at least five, at least six, at least seven, at least eight, at least nine or more applications may be used. The multiple applications may be applied at any appropriate time points according to a method or treatment of the invention. By way of non-limiting example, a REV-ERB inhibitory compound of the invention, a Notch ligand and/or a compound which alters E4bp4 post-translational modification may each independently be applied twice a day, once daily, every other day, once every three days or weekly. Typically the REV-ERB inhibitory compounds of the invention, the Notch ligand and/or a compound which alters E4bp4 post-translational modification may independently be applied as necessary when the culture medium is changed.

The method of the invention may further comprise modulating (increasing or decreasing the expression and/or activity of one or more additional gene and/or protein in the HPCs in order to enhance NK cell expansion. This modulation may be elicited by a compound of the invention, including the same compound of the invention as used to inhibit the activity of REV-ERB. Alternatively, one or more additional compounds may be used to modulate the expression and/or activity of the one or more additional gene and/or protein. Said modulation may occur directly or indirectly. Indirect modulation encompasses downstream effects caused by a compound of the invention inhibiting the activity of REV-ERB.

In all methods of the invention, the sample comprising HPCs obtained from an individual/patient may be a sample obtained from bone marrow, cord blood and/or peripheral blood. Thus, the sample may be a cord or peripheral blood sample, or a bone marrow sample or biopsy. The sample may be obtained from the individual who is to be treated with the NK cell population produced by a method of the invention (i.e. a patient). Alternatively, the sample is obtained from a healthy individual.

According to the present invention, a sample comprising HPCs is any sample from an individual which comprises a sufficient number of HPCs (as described herein), such that an expanded NK cell population can be obtained by contacting said sample with a compound according to the present invention. Typically the sample comprises HSCs. Preferably said sample is enriched for HSCs, such as a cord or peripheral blood sample or a bone marrow sample or biopsy as described herein.

A method of the invention may result in an increase in, the number of NK cells of at least 1.5-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 4-fold, at least 5-fold, at least 6-fold, at least 7-fold, at least 8-fold, at least 9-fold, at least 10-fold or more relative to a control. Typically the number of NK cells is increased by at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, or more compared with the control.

A method of the invention may accelerate the production of phenotypically mature NK cells. In other words, the method of the invention may reduce the time taken to arrive at a population of mature NK cells. A reduction in the run time of the method offers a further advantage over the conventional methods for NK cell expansion known in the art. As a non-limiting example, current clinical procedures for the expansion of NK cells can take more than two weeks to generate an NK cell population that comprises about 20% mature NK cells. In contrast, a method of the invention may achieve an equivalent population in 10 days or less, preferably in one week or less. A method of the invention may achieve a population of at least 40% mature NK cells, preferably at least 45%, at least 46%, at least 47%, at least 48%, or at least 49% mature NK cells, even more preferably at least 50% mature NK cells in three weeks or less, 20 days or less, 19 days or less, 18 days or less, 17 days or less, 16 days or less, 15 days or less, two weeks or less, 13 days or less, or 12 days or less. Preferably a method of the invention can achieve a population of at least 45% mature NK cells within two weeks or less.

Typically an ex vivo method of the present invention involves a final step to purify the expanded NK cell population. This ensures a pure population for therapeutic administration as described herein. Purification of the expanded NK cell population may be by any appropriate means. Standard cell purification methods are known in the art, such as cell sorting, including fluorescence-activated cell sorting (FACS) and magnetic-activated cell sorting (MACS).

In some methods of the invention, including but not limited to those involving the combination of a Notch ligand and a REV-ERB inhibitory compound, the % of NK cells in the final cell population may be very high (typically greater than 85%, preferably greater than 90%, more preferably greater than 95%, and may approach 100%). In such instances, a final purification step may optionally be omitted.

Therapeutic Indications

The invention provides a REV-ERB antagonist for use in a method of therapy by increasing the production of NK cells in a patient.

The REV-ERB antagonist for use in said method of therapy may be any REV-ERB antagonist as described herein. Typically the REV-ERB antagonist for use in said method increases E4bp4 expression by decreasing REV-ERB activity.

Typically the method of therapy comprises administering a compound which inhibits the action of REV-ERB (as described herein) to a patient or subject.

The invention also provides products containing a compound which inhibits the action of REV-ERB and a Notch ligand as a combined preparation for simultaneous, separate or sequential use in a method of therapy by increasing the production of NK cells in a patient.

The Notch ligand for use in said method of therapy may be any Notch ligand as described herein. In some preferred embodiments, the Notch ligand is DLL4 or a fragment thereof which retains the function of DLL4. Any REV-ERB antagonist and any Notch ligand of the invention may be used in combination.

Typically a method of therapy relating to said REV-ERB antagonist and Notch ligand products comprises administering the products (as described herein) to a patient or subject. The Notch ligand and REV-ERB antagonist may be administered simultaneously, separately or sequentially. For separate or sequential administration, the Notch ligand may be administered first, followed by the REV-ERB antagonist, or vice versa.

Sequential administration may mean that the two products are administered immediately one after the other, or that the second product is administered within 1 minute, within two minutes, within three minutes, within four minutes, within five minutes, within 10 minutes, within 15 minutes, within 20 minutes, within 25 minutes, within 30 minutes, within 45 minutes, within one hour, or more of the first product being administered.

Separate administration may mean that the second product is administered within one hour, within two hours, within three hours, within six hours, within 12 hours, within 24 hours, within 2 days, within 3 days, within 4 days, within 5 days, within 6 days, within 7 days or more of the first product being administered.

As used herein, the term "increasing the number of NK cells" and "increasing production of NK cells" can be understood to mean that the compound of the invention elicits a significant increase in the number of NK cells in a patient. This increase in NK cell number may be measured relative to a control (as described herein in the context of increasing E4bp4 expression and inhibiting REV-ERB activity).

A reference to an increase in the number of NK cells and/or increasing NK cell production may be quantified in terms of a fold increase relative to a control. Typically a compound of the invention can increase the number of NK cells, or give rise to an increase in NK cell production, of at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 3 fold or more relative to a control.

Alternatively, a reference to increasing the number of NK cells and/or increasing NK cell production may be understood to mean that, the number of NK cells is increased by at least 10%, at least 20%, at least 30%, at least 40%, at least 50%, at least 60, at least 70%, at least 80%, at least 85%, at least 90%, at least 95%, at least 100%, at least 150%, at least 200%, at least 300% or more compared with the control. Typically the number of NK cells is increased by at least 50%, preferably at least 70%, more preferably at least 80%, even more preferably at least 90% or more compared with a control.

In some embodiments, an increase in the number of NK cells and/or increase in NK cell production may be defined in terms of the absolute number of NK cells in a sample or patient, such as the percentage of NK cells, for example the percentage of NK cells in the circulating lymphocyte population. For example, a compound of the invention may cause an increase in NK number, resulting in a percentage of NK cells of at least 10%, at least 15%, at least 20%, at least 25%, at least 30%, at least 35%, at least 40%, at least 45%, at least 50%, at least 55%, at least 60%, at least 65%, at least 70%, at least 75%, at least 80% or more.

The number of NK cells may be determined by quantitative and/or qualitative analysis, and may be measured directly or indirectly. The number of NK cells relative to a control may be determined using any appropriate technique. Suitable standard techniques, such as flow cytometry, FACS and MACS, are known in the art.

The number of NK cells may be increased compared with a control for at least 6 hours, at least 12 hours, at least 24 hours, at least 30 hours, at least 36 hours, at least 42 hours, at least 48 hours, at least 54 hours, at least 60 hours, at least 72 hours, at least 4 days, at least 5 days, at least 6 days, at least 1 week, at least 2 weeks, at least 3 weeks, at least 1 month or more. Typically this is assessed relative to the last administration of the compound which inhibits REV-ERB activity.

The number of NK cells may be quantified in terms of the total number of NK cells in a sample from a patient or culture sample (from an ex vivo method of the invention).

In the context of the therapeutic uses and methods of the invention, a "subject" or "patient" (these terms are used interchangeably herein) is any animal patient that would benefit from an increase in the number of NK cells. Typical animal patients are mammals, such as primates. Preferably the patient is a human.

Thus, the present invention provides a method of treatment by increasing the number of NK cells in a patient in need thereof, comprising administering to said patient a therapeutically effective amount of a compound which inhibits the action of REV-ERB (as described herein). Also provided is a method of treatment by increasing the number of NK cells in a patient in need thereof, comprising administering to said patient a therapeutically effective amount of a compound which inhibits the action of REV-ERB (as described herein) and a Notch ligand (as described herein).

Additionally, the present invention provides the use of a compound which inhibits the action of REV-ERB in the manufacture of a medicament. Said medicament increases the number of NK cells in a patient. Additionally, the present invention provides the use of a compound which inhibits the action of REV-ERB and a Notch ligand in the manufacture of a medicament. Said medicament increases the number of NK cells in a patient.

The therapeutic use or method of the invention may comprise administering a therapeutically effective amount of a compound or products of the invention, either alone or in combination with other therapeutic agents, to a subject.

As used herein, the term "treatment" or "treating" embraces therapeutic or preventative/prophylactic measures.

The compounds of the invention may also be used as a preventative therapy. As used herein, the term "preventing" includes preventing the onset of symptoms associated with a disease or disorder that may be treated by increasing NK cell number and/or reducing the severity or intensity of said symptoms. The term "preventing" includes inducing or providing protective immunity against such diseases or disorders, particularly infectious diseases as described herein. Immunity may be quantified using any appropriate technique, examples of which are known in the art.

A compound or products of the invention may be administered to a patient already having a disease or disorder which may be treated by increasing NK cell number. For example, the patient may be suspected of having an infectious disease or cancer as described herein, and may or may not be showing symptoms of said disease or disorder. When administered to such a patient, a compound or products of the invention can cure, delay, reduce the severity of, or ameliorate one or more symptoms, and/or prolong the survival of a subject beyond that expected in the absence of such treatment.

Alternatively, a compound or products of the invention may be administered to a patient who may ultimately be infected with a particular infectious disease, or develop a disease or disorder as described herein, in order to cure, delay, reduce the severity of, or ameliorate one or more symptoms, and/or prolong the survival of a subject beyond that expected in the absence of such treatment, or, in the case of infectious diseases help prevent that patient from transmitting said disease.

The treatments and preventative therapies of the present invention are applicable to a variety of different subjects of different ages. In the context of humans, the therapies are applicable to children (e.g. infants, children under 5 years old, older children or teenagers) and adults. In the context of other animal subjects (e.g. mammals such as primates), the therapies are applicable to immature subjects and mature/adult subjects.

The invention relates to the treatment of any disease or disorder which may be beneficially treated with by increasing the number of NK cells in a patient. Such diseases and disorders include cancer, infectious diseases (acute and chronic), autoimmune diseases and diseases or disorders related to female infertility or pregnancy. Infectious diseases that may be treated according to the present invention include viral infection, and infection by other pathogens, including bacteria, protists, fugal, or helminth pathogens. Typically said pathogens are intracellular pathogens which have at least one intracellular phase in their life cycle. Infections of particular interest include viral infections, and zoonotic infections that are of particular importance from a public health perspective. Cancers that may be treated according to the present invention include bladder cancer, blood cancers, leukaemia, bone cancers, bowel cancer, brain tumours, breast cancer, kidney cancer, liver cancer, lung cancer, melanoma, ovarian cancer, pancreatic cancer, prostate cancer, skin cancer, stomach cancer, testicular cancer and uterine cancer. Autoimmune diseases that may be treated according to the present invention include systemic lupus erythematosus, rheumatoid arthritis, multiple sclerosis and obesity-induced insulin resistance. As used herein, the term diseases or disorders related to female infertility or pregnancy includes, but is not limited to, fetal growth restriction, preterm labour, defects in uterine vascular remodelling and preeclampsia.

The compounds or products of the invention may be used in combination with one or more additional therapeutic agents or treatments, which typically may be selected from a conventional treatment for the disease or disorder to be treated. As a non-limiting example, if a compound or products of the invention are for use in the treatment of a cancer, such as lung cancer, then said compound or products may be used in combination with conventional treatments for lung cancer, such as radiotherapy, chemotherapy or surgery. When used in combination with one or more additional therapeutic agent or treatment, a compound or products of the invention may be administered before, simultaneously with, or after the administration of the one or more additional therapeutic agent or treatment.

In some preferred embodiments, a compound or products of the invention is for use in combination with antibody-mediated immunotherapy. Antibody-mediated immunotherapy involves the administration of antibodies to a patient to target disease-specific antigens. Such antibodies could be used to increase the specificity and killing activity of NK cells, which express receptors for the Fc regions of IgG antibodies. Activation of these Fc receptors, leads to NK cell activation, resulting in cytokine secretion and release of cytotoxic granules by the activated NK cell, causing lysis of the cell expressing the disease antigen. Such combination therapy is particularly preferred for the treatment of cancer (using antibodies to tumour-specific antigens). Any antibody used in immunotherapy may be used in combination with a compound of the invention. Non-limiting examples of such antibodies include anti-CD20 mAbs (non-Hodgkin's lymphoma, chronic lymphocytic lymphoma), anti-ganglioside D2 (anti-GD2) mAbs (neuroblastoma, melanoma), anti-human epidermal growth factor (anti-HER2) mAbs (breast and gastric cancers), anti-epidermal growth factor receptor (anti-EGFR) mAbs (colorectal and head and neck cancer).

In other aspects, the invention provides the use of an expanded NK cell population (as described herein) in a therapeutic use or method as described herein. Any and all of the disclosure herein in relation to therapeutic indications of a compound or products of the invention may apply equally and independently to therapeutic applications of the expanded NK cell populations of the invention. As a non-limiting example, the present invention provides an expanded NK cell population (as described herein) for use in a method of therapy, for example in the treatment of cancer, an infectious diseases, an autoimmune disease or a disease or disorder related to female infertility or pregnancy. As another non-limiting example, the invention provides a method of treatment by increasing the number of NK cells in a patient in need thereof, comprising administering to said patient a therapeutically effective amount of an expanded NK cell population.

Pharmaceutical Compositions and Formulations

The "compound" and products described herein may be comprised in a "therapeutic/prophylactic composition", "formulation" or "medicament" of the invention.

The compound or expanded NK cell population of the invention (as defined above) can be combined or administered in addition to a pharmaceutically acceptable carrier, diluent and/or excipient. Alternatively or in addition the compound or expanded NK cell population of the invention can further be combined with one or more of a salt, excipient, diluent, adjuvant, immunoregulatory agent and/or antimicrobial compound.

The compound of formula (I) may be in the form of a salt, particularly a pharmaceutically acceptable salt. Pharmaceutically acceptable salts include acid addition salts formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Administration of immunogenic compositions, therapeutic formulations, medicaments and prophylactic formulations is generally by conventional routes e.g. intravenous, subcutaneous, intraperitoneal, or mucosal routes. The administration may be by parenteral injection, for example, a subcutaneous, intradermal or intramuscular injection. For example, formulations comprising antibodies or expanded NK cell populations of the invention may be particularly suited to administration intravenously, intramuscularly, intradermally, or subcutaneously. Administration of small molecule REV-ERB inhibitors may be injection, such as intravenously, intramuscularly, intradermally, or subcutaneously, or by oral administration (small molecules with molecule weight of less than 500 Da typically exhibiting oral bioavailability).

Accordingly, immunogenic compositions, therapeutic formulations, medicaments and prophylactic formulations of the invention may be prepared as injectables, either as liquid solutions or suspensions. Solid forms suitable for solution in, or suspension in, liquid prior to injection may alternatively be prepared. The preparation may also be emulsified, or the peptide encapsulated in liposomes or microcapsules.

The active immunogenic ingredients (such as the compounds or expanded NK cell populations of the invention) are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine.

Generally, the carrier is a pharmaceutically-acceptable carrier. Non-limiting examples of pharmaceutically acceptable carriers include water, saline, and phosphate-buffered saline. In some embodiments, however, where the composition comprises a compound of the invention, this may be in lyophilized form, in which case it may include a stabilizer, such as BSA. In some embodiments, it may be desirable to formulate the composition with a preservative, such as thiomersal or sodium azide, to facilitate long term storage.

Examples of additional adjuvants which may be effective include but are not limited to: complete Freunds adjuvant (CFA), Incomplete Freunds adjuvant (IFA), Saponin, a purified extract fraction of Saponin such as Quil A, a derivative of Saponin such as QS-21, lipid particles based on Saponin such as ISCOM/ISCOMATRIX, E. coli heat labile toxin (LT) mutants such as LTK63 and/or LTK72, aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-di-palmitoyl-sn-glycero-3-hydroxyphosphoryl oxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion, the MF59 formulation developed by Novartis, and the AS02, AS01, AS03 and AS04 adjuvant formulations developed by GSK Biologicals (Rixensart, Belgium).

Examples of buffering agents include, but are not limited to, sodium succinate (pH 6.5), and phosphate buffered saline (PBS; pH 6.5 and 7.5).

Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders.

The dosage ranges for administration of the compounds or products of the present invention are those which produce the desired therapeutic effect. It will be appreciated that the dosage range required depends on the precise nature of the compound, the route of administration, the nature of the formulation, the age of the patient, the nature, extent or severity of the patient's condition, contraindications, if any, and the judgement of the attending physician. Variations in these dosage levels can be adjusted using standard empirical routines for optimisation. Similarly, the dose of a compound or products of the invention for use in a method of the invention, particularly an ex vivo method, can be readily determined by one of skill in the art, and is any dose that produces the desired increase in NK cell number and/or elicits the desired expansion in NK cells, to produce an expanded NK cell population. As a non-limiting example, doses of compound 7 or 11 according to the present invention may give rise to a final concentration of about 2 to about 20 µM, about 2 to about 15 µM, about 5 to about 15 µM, about 5 to about 14 µM, about 4 to about 13 µM, about 5 to about 12 µM, about 5 to about 11 µM, or preferably about 5 to about 10 µM.

The invention also provides the use of an expanded NK cell population (as described herein) in a pharmaceutical formulation. Any and all of the disclosure herein in relation to formulations of a compound of the invention may apply equally and independently to therapeutic applications of the expanded NK cell populations of the invention.

Key to SEQ ID NOs

E4bp4 gene sequence (X64318.1)

SEQ ID NO: 1

```
  1  gcccctttct ttctcctcgt cggcccgaga gcaggaacac gataacgaag gaggcccaac 61  ttcattcaat aaggagcctg acggatttat cccagacggt agaacaaaag gaagaatatt
```

-continued

```
 121 gatggatttt aaaccagagt ttttaaagag cttgagaata cggggaaatt aatttgttct
 181 cctacacaca tagatagggt aaggttgttt ctgatgcagc tgagaaaaat gcagaccgtc
 241 aaaaaggagc aggcgtctct tgatgccagt agcaatgtgg acaagatgat ggtccttaat
 301 tctgctttaa cggaagtgtc agaagactcc acaacaggtg aggacgtgct ctcagtgaa
 361 ggaagtgtgg ggaagaacaa atcttctgca tgtcggagga acgggaatt cattcctgat
 421 gaaagaaag atgctatgta ttgggaaaaa aggcggaaaa ataatgaagc tgccaaaaga
 481 tctcgtgaga agcgtcgact gaatgacctg gttttagaga acaaactaat tgcactggga
 541 gaagaaaacg ccacttttaaa agctgagctg cttttcactaa aattaaagtt tggtttaatt
 601 agctccacag catatgctca agagattcag aaactcagta attctacagc tgtgtacttt
 661 caagattacc agacttccaa atccaatgtg agttcatttg tggacgagca cgaaccctcg
 721 atggtgtcaa gtagttgtat ttctgtcatt aaacactctc cacaaagctc gctgtccgat
 781 gtttcagaag tgtcctcagt agaacacacg caggagagct ctgtgcaggg aagctgcaga
 841 agtcctgaaa acaagttcca gattatcaag caagagccga tggaattaga gagctacaca
 901 agggagccaa gagatgaccg aggctcttac acagcgtcca tctatcaaaa ctatatgggg
 961 aattctttct ctgggtactc acactctccc ccactactgc aagtcaaccg atcctccagc
1021 aactccccga gaacgtcgga aactgatgat ggtgtggtag gaaagtcatc tgatggagaa
1081 gacgagcaac aggtccccaa gggccccatc cattctccag ttgaactcaa gcatgtgcat
1141 gcaactgtgg ttaaagttcc agaagtgaat tcctctgcct tgccacacaa gctccggatc
1201 aaagccaaag ccatgcagat caaagtagaa gcctttgata tgaatttga ggccacgcaa
1261 aaactttcct cacctattga catgacatct aaaagacatt tcgaactcga aaagcatagt
1321 gccccaagta tggtacattc ttctcttact cctttctcag tgcaagtgac taacattcaa
1381 gattggtctc tcaaatcgga gcactggcat caaaagaac tgagtggcaa aactcagaat
1441 agtttcaaaa ctggagtgtg tgaaatgaaa gacagtggct acaaagtttc tgacccagag
1501 aacttgtatt tgaagcaggg gatagcaaac ttatctgcag aggttgtctc actcaagaga
1561 cttatagcca cacaaccaat ctctgcttca gactctgggt aaattactac tgagtaagag
1621 ctgggcattt agaaagatgt catttgcaat agagcagtcc attttgtatt atgctgaatt
1681 ttcactggac ctgtgatgtc atttcactgt gatgtgcaca tgttgtctgt ttggtgtctt
1741 tttgtgcaca gattatgatg aagattagat tgtgttatca ctctgcctgt gtatagtcag
1801 atagtcatat gcgtaaggct gtatatatta agntttttatt tttgttgttc tattataaag
1861 tgtgtaagtt accagtttca ataaggatt ggtgacaaac acagaaaaaa aaaaaaaaa
1921 aaa
```

E4bp4 amino acid sequence (X64318.1)

SEQ ID NO: 2

MQLRKMQTVKKEQASLDASSNVDKMMVLNSALTEVSEDSTTGEDVLLSEGSVGKNKSSACRRKREFIPDEKKDAM
YWEKRRKNNEAAKRSREKRRINDLVLENKLIALGEENATLKAELLSLKLKFGLISSTAYAQEIQKLSNSTAVYFQ
DYQTSKSNVSSFVDEHEPSMVSSSCISVIKHSPQSSLSDVSEVSSVEHTQESSVQGSCRSPENKFQIIKQEPMEL
ESYTREPRDDRGSYTASIYQNYMGNSFSGYSHSPPLLQVNRSSSNSPRISETDDGVVGKSSDGEDEQQVPKGPIH
SPVELKHVHATVVKVPEVNSSALPHKLRIKAKAMQIKVEAFDNEFEATQKLSSPIDMTSKRHFELEKHSAPSMVH
SSLTPFSVQVTNIQDWSLKSEHWHQKELSGKTQNSFKTGVVEMKDSGYKVSDPENLYLKQGIANLSAEVVSLKRL
IATQPISASDSG

-continued

REV-ERBα gene sequence (NM_021724.4)

SEQ ID NO: 3

```
   1  gggcacgagg cgctccctgg gatcacatgg tacctgctcc agtgccgcgt gcggcccggg
  61  aaccctgggc tgctggcgcc tgcgcagagc cctctgtccc agggaaaggc tcgggcaaaa
 121  ggcggctgag attggcagag tgaaatatta ctgccgaggg aacgtagcag ggcacacgtc
 181  tcgcctcttt gcgactcggt gccccgtttc tccccatcac ctacttactt cctggttgca
 241  acctctcttc ctctgggact tttgcaccgg gagctccaga ttcgccaccc cgcagcgctg
 301  cggagccggc aggcagaggc accccgtaca ctgcagagac ccgaccctcc ttgctacctt
 361  ctagccagaa ctactgcagg ctgattcccc ctacacactc tctctgctct tcccatgcaa
 421  agcagaactc cgttgcctca acgtccaacc cttctgcagg gctgcagtcc ggccacccca
 481  agaccttgct gcagggtgct tcggatcctg atcgtgagtc gcgggtccca ctccccgccc
 541  ttagccagtg cccaggggc aacagcggcg atcgcaacct ctagtttgag tcaaggtcca
 601  gtttgaatga ccgctctcag ctggtgaaga catgacgacc ctggactcca acaacaacac
 661  aggtggcgtc atcacctaca ttggctccag tggctcctcc ccaagccgca ccagccctga
 721  atccctctat agtgacaact ccaatggcag cttccagtcc ctgacccaag gctgtcccac
 781  ctacttccca ccatccccca ctggctccct cacccaagac ccggctcgct cctttgggag
 841  cattccaccc agcctgagtg atgacggctc cccttcttcc tcatcttcct cgtcgtcatc
 901  ctcctcctcc ttctataatg ggagccccc tgggagtcta caagtggcca tggaggacag
 961  cagccgagtg tcccccagca agagcaccag caacatcacc aagctgaatg catggtgtt
1021  actgtgtaaa gtgtgtgggg acgttgcctc gggcttccac tacggtgtgc acgcctgcga
1081  gggctgcaag ggcttttttcc gtcggagcat ccagcagaac atccagtaca aaaggtgtct
1141  gaagaatgag aattgctcca tcgtccgcat caatcgcaac cgctgccagc aatgtcgctt
1201  caagaagtgt ctctctgtgg gcatgtctcg agacgctgtg cgttttgggc gcatccccaa
1261  acgagagaag cagcggatgc ttgctgagat gcagagtgcc atgaacctgg ccaacaacca
1321  gttgagcagc cagtgcccgc tggagacttc acccacccag cacccccaccc caggccccat
1381  gggccccctcg ccacccctg ctccggtccc ctcacccctg gtgggcttct cccagtttcc
1441  acaacagctg acgcctccca gatccccaag ccctgagccc acagtggagg atgtgatatc
1501  ccaggtggcc cgggcccatc gagagatctt cacctacgcc catgacaagc tgggcagctc
1561  acctggcaac ttcaatgcca accatgcatc aggtagccct ccagccacca ccccacatcg
1621  ctgggaaaat cagggctgcc cacctgcccc caatgacaac aacaccttgg ctgcccagcg
1681  tcataacgag gccctaaatg gtctgcgcca ggctccctcc tcctaccctc ccacctggcc
1741  tcctggccct gcacaccaca gctgccacca gtccaacagc aacgggcacc gtctatgccc
1801  cacccacgtg tatgcagccc agaaggcaa ggcacctgcc aacagtcccc ggcagggcaa
1861  ctcaaagaat gttctgctgg catgtcctat gaacatgtac ccgcatggac gcagtgggcg
1921  aacggtgcag gagatctggg aggatttctc catgagcttc acgcccgctg tgcgggaggt
1981  ggtagagttt gccaaacaca tcccgggctt ccgtgaccgt tctcagcatg accaagtcac
2041  cctgcttaag gctggcacct ttgaggtgct gatggtgcgc tttgcttcgt tgttcaacgt
2101  gaaggaccag acagtgatgt tcctaagccg caccacctac agcctgcagg agcttggtgc
2161  catgggcatg ggagacctgc tcagtgccat gttcgacttc agcgagaagc tcaactccct
2221  ggcgcttacc gaggaggagc tgggcctctt caccgcggtg tgcttgtct ctgcagaccg
2281  ctcgggcatg gagaattccg cttcggtgga gcagctccag gagacgctgc tgcgggctct
2341  tcgggctctg gtgctgaaga accggccctt ggagacttcc cgcttcacca gctgctgct
```

-continued

```
2401  caagctgccg gacctgcgga ccctgaacaa catgcattcc gagaagctgc tgtccttccg
2461  ggtggacgcc cagtgacccg cccggccggc cttctgccgc tgccccttg tacagaatcg
2521  aactctgcac ttctctctcc tttacgagac gaaaaggaaa agcaaaccag aatcttattt
2581  atattgttat aaaatattcc aagatgagcc tctggccccc tgagccttct tgtaaatacc
2641  tgcctccctc ccccatcacc gaacttcccc tcctcccta tttaaaccac tctgtctccc
2701  ccacaaccct ccctggccc tctgatttgt tctgttcctg tctcaaatcc aatagttcac
2761  agctgagctg gcttcaaaaa aaaaaaaaaa aaa
```

REV-ERBα amino acid sequence (NM_021724.4)

SEQ ID NO: 4

MTTLDSNNNTGGVITYIGSSGSSPSRTSPESLYSDNSNGSFQSLTQGCPTYFPPSPTGSLTQDPARSFGSIPPSL
SDDGSPSSSSSSSSSSSSSFYNGSPPGSLQVAMEDSSRVSPSKSTSNITKLNGMVLLCKVCGDVASGFHYGVHACE
GCKGFFRRSIQQNIQYKRCLKNENCSIVRINRNRCQQCRFKKCLSVGMSRDAVRFGRIPKREKQRMLAEMQSAMN
LANNQLSSQCPLETSPTQHPTPGPMGPSPPPAPVPSPLVGFSQFPQQLTPPRSPSPEPTVEDVISQVARAHREIF
TYAHDKLGSSPGNFNANHASGSPPATTPHRWENQGCPPAPNDNNTLAAQRHNEALNGLRQAPSSYPPTWPPGPAH
HSCHQSNSNGHRLCPTHVYAAPEGKAPANSPRQGNSKNVLLACPMNMYPHGRSGRTVQEIWEDFSMSFTPAVREV
VEFAKHIPGFRDLSQHDQVILLKAGTFEVLMVRFASLFNVKDQTVMFLSRTTYSLQELGAMGMGDLLSAMFDFSE
KLNSLALTEEELGLFTAVVLVSADRSGMENSASVEQLQETLLRALRALVLKNRPLETSRFTKLLLKLPDLRTLNN
MHSEKLLSFRVDAQ

REV-ERBβ gene sequence (AB307693.1)

SEQ ID NO: 5

```
   1  atggaggtga atgcaggagg tgtgattgcc tatatcagtt cttccagctc agcctcaagc
  61  cctgcctctt gtcacagtga gggttctgag aatagtttcc agtcctcctc ctcttctgtt
 121  ccatcttctc caaatagctc taattctgat accatggta atcccaagaa tggtgatctc
 181  gccaatattg aaggcatctt gaagaatgat cgaatagatt gttctatgaa aacaagcaaa
 241  tcgagtgcac ctgggatgac aaaaaatcat agtggtgtga caaaatttag tggcatggtt
 301  ctactgtgta aagtctgtgg ggatgtggcg tcaggattcc actatggagt tcatgcttgc
 361  gaaggctgta agggtttctt tcggagaagt attcaacaaa acatccagta caagaagtgc
 421  ctgaagaatg aaaactgttc tataatgaga atgaatagga acagatgtca gcaatgtcgc
 481  ttcaaaaagt gtctgtctgt tggaatgtca agagatgctg ttcggtttgg tcgtattcct
 541  aagcgtgaaa acagaggat gctaattgaa atgcaaagtg caatgaagac catgatgaac
 601  agccagttca gtggtcactt gcaaaatgac acattagtag aacatcatga acagacagcc
 661  ttgccagccc aggaacagct gcgacccaag ccccaactgg agcaagaaaa catcaaaagc
 721  tcttctcctc catcttctga ttttgcaaag gaagaagtga ttggcatggt gaccagagct
 781  cacaaggata ccttttatgta taatcaagag cagcaagaaa actcagctga gagcatgcag
 841  ccccagagag agaacggat tcccaagaac atggagcaat ataatttaaa tcatgatcat
 901  tgcggcaatg ggcttagcag ccattttccc tgtagtgaga gccagcagca tctcaatgga
 961  cagttcaaag ggaggaatat aatgcattac ccanatggcc atgccatttg tattgcaaat
1021  ggacattgta tgaacttctc caatgcttat actcaaagag tatgtgatag agttccgata
1081  gatggatttt ctcagaatga gaacaagaat agttacctgt gcaacactgg aggaagaatg
1141  catctggttt gtccaatgag taagtctcca tatgtggatc ctcataaatc aggacatgaa
1201  atctgggaag aattttcgat gagcttcact ccagcagtga agaagtggt ggaatttgca
1261  aagcgtattc ctgggttcag agatctctct cagcatgacc aggtcaacct tttaaaggct
```

-continued

```
1321  gggacttttg aggttttaat ggtacggttc gcatcattat ttgatgcaaa ggaacgtact
1381  gtcaccttt  taagtggaaa gaaatatagt gtggatgatt tacactcaat gggagcaggg
1441  gatctgctaa actctatgtt tgaatttagt gagaagctaa atgccctcca acttagtgat
1501  gaagagatga gtttgtttac agctgttgtc ctggtatctg cagatcgatc tggaatagaa
1561  aacgtcaact ctgtggaggc tttgcaggaa actctcattc gtgcactaag gaccttaata
1621  atgaaaaacc atccaaatga ggcctctatt tttacaaaac tgcttctaaa gttgccagat
1681  cttcgatctt taaacaacat gcactctgag gagctcttgg cctttaaagt tcacccttaa
```

REV-ERBβ amino acid sequence (AB307693.1)
SEQ ID NO: 6

MEVNAGGVIAYISSSSSASSPASCHSEGSENSFQSSSSSVPSSPNSSNSDTNGNPKNGDLANIEGILKNDRIDCS
MKTSKSSAPGMTKNHSGVTKFSGMVLLCKVCGDVASGFHYGVHACEGCKGFFRRSIQQNIQYKKCLKNENCSIMR
MNRNRCQQCRFKKCLSVGMSRDAVRFGRIPKREKQRMLIEMQSAMKTMMNSQFSGHLQNDTLVEHHEQTALPAQE
QLRPKPQLEQENIKSSSPPSSDFAKEEVIGMVTRAHKDTFMYNQEQQENSAESMQPQRGERIPKNMEQYNINHDH
CGNGLSSHFPCSESQQHLNGQFKGRNIMHYPXGHAICIANGHCMNFSNAYTQRVCDRVPIDGFSQNENKNSYLCN
TGGRMHLVCPMSKSPYVDPHKSGHEIWEEFSMSFTPAVKEVVEFAKRIPGFRDLSQHDQVNLLKAGTFEVLMVRF
ASLFDAKERTVTFLSGKKYSVDDLHSMGAGDLLNSMFEFSEKLNALQLSDEEMSLFTAVVLVSADRSGIENVNSV
EALQETLIRALRTLIMKNHPNEASIFTKLLLKLPDLRSLNNMHSEELLAFKVH

Delta-like ligand 4 gene sequence (AF253468.1)
SEQ ID NO: 7

```
   1  atggcggcag cgtcccggag cgcctctggc tgggcgctac tgctgctggt ggcactttgg
  61  cagcagcgcg cggccggctc cggcgtcttc cagctgcagc tgcaggagtt catcaacgag
 121  cgcggcgtac tggccagtgg gcggccttgc gagcccggct gccggacttt cttccgcgtc
 181  tgccttaagc acttccaggc ggtcgtctcg cccggaccct gcaccttcgg gaccgtctcc
 241  acgccggtat tgggcaccaa ctccttcgct gtccgggacg acagtagcgg cggggggcgc
 301  aaccctctcc aactgccctt caatttcacc tggccgggta ccttctcgct catcatcgaa
 361  gcttggcacg cgccaggaga cgacctgcgg ccagaggcct tgccaccaga tgcactcatc
 421  agcaagatcg ccatccaggg ctccctagct gtgggtcaga actggttatt ggatgagcaa
 481  accagcaccc tcacaaggct gcgctactct taccgggtca tctgcagtga caactactat
 541  ggagacaact gctcccgcct gtgcaagaag cgcaatgacc acttcggcca ctatgtgtgc
 601  cagccagatg caacttgtc  ctgcctgccc ggttggactg gggaatattg ccaacagcct
 661  atctgtcttt cgggctgtca tgaacagaat ggctactgca gcaagccagc agagtgcctc
 721  tgccgcccag gctggcaggg ccggctgtgt aacgaatgca tcccccacaa tggctgtcgc
 781  cacggcacct gcagcactcc ctggcaatgt acttgtgatg agggctgggg aggcctgttt
 841  tgtgaccaag atctcaacta ctgcacccac cactccccat gcaagaatgg ggcaacgtgc
 901  tccaacagtg gcagcgaag  ctacacctgc acctgtcgcc caggctacac tggtgtggac
 961  tgtgagctgg agctcagcga gtgtgacagc aaccctgtc  gcaatggagg cagctgtaag
1021  gaccaggagg atggctacca ctgcctgtgt cctccgggct actatggcct gcattgtgaa
1081  cacagcacct tgagctcgcg cgactccccc tgcttcaatg ggggctcctg ccgggagcgc
1141  aaccaggggg ccaactatgc ttgtgaatgt ccccccaact tcaccggctc caactgcgag
1201  aagaaagtgg acaggtgcac cagcaacccc tgtgccaacg ggggacagtg cctgaaccga
1261  ggtccaagcc gcatgtgccg ctgccgtcct ggattcacgg gcacctactg tgaactccac
1321  gtcagcgact gtgcccgtaa cccttgcgcc cacggtggca cttgccatga cctggagaat
1381  gggctcatgt gcacctgccc tgccggcttc tctggccgac gctgtgaggt gcggacatcc
```

```
-continued 1441  atcgatgcct gtgcctcgag tccctgcttc aacagggcca cctgctacac cgacctctcc 1501  acagacacct ttgtgtgcaa ctgcccttat ggctttgtgg gcagccgctg cgagttcccc 1561  gtgggcttgc cgcccagctt ccctgggtg gccgtctcgc tgggtgtggg gctggcagtg 1621  ctgctggtac tgctgggcat ggtggcagtg gctgtgcggc agctgcggct tcgacggccg 1681  gacgacggca gcagggaagc catgaacaac ttgtcggact tccagaagga caacctgatt 1741  cctgccgccc agcttaaaaa cacaaccag aagaaggagc tggaagtgga ctgtggcctg 1801  gacaagtcca actgtggcaa acagcaaaac cacacattgg actataatct ggccccaggg 1861  cccctggggc ggggaccat gccaggaaag tttccccaca gtgacaagag cttaggagag 1921  aaggcgccac tgcggttaca cagtgaaaag ccagagtgtc ggatatcagc gatatgctcc 1981  cccagggact ccatgtacca gtctgtgtgt ttgatatcag aggagaggaa tgaatgtgtc 2041  attgccacgg aggtataa
```

Delta-like ligand 4 amino acid sequence (AF253468.1)

SEQ ID NO: 8

MAAASRSASGWALLLLVALWQQRAAGSGVFQLQLQEFINERGVLASGRPCEPGCRTFFRVCLKHFQAVVSPGPCT
FGTVSTPVLGTNSFAVRDDSSGGGRNPLQLPFNFTWPGTFSLIIEAWHAPGDDLRPEALPPDALISKIAIQGSLA
VGQNWLLDEQTSTLTRLRYSYRVICSDNYYGDNCSRLCKKRNDHFGHYVCQPDGNLSCLPGWTGEYCQQPICLSG
CHEQNGYCSKPAECLCRPGWQGRLCNECIPHNGCRHGTCSTPWQCTCDEGWGGLFCDQDLNYCTHHSPCKNGATC
SNSGQRSYTCTCRPGYTGVDCELELSECDSNPCRNGGSCKDQEDGYHCLCPPGYYGLHCEHSTLSCADSPCFNGG
SCRERNQGANYACECPPNFTGSNCEKKVDRCTSNPCANGGQCLNRGPSRMCRCRPGFTGTYCELHVSDCARNPCA
HGGTCHDLENGLMCTCPAGFSGRRCEVRTSIDACASSPCFNRATCYTDLSTDTFVCNCPYGFVGSRCEFPVGLPP
SFPWVAVSLGVGLAVLLVLLGMVAVAVRQLRLRRPDDGSREAMNNLSDFQKDNLIPAAQLKNTNQKKELEVDCGL
DKSNCGKQQNHTLDYNLAPGPLGRGTMPGKFPHSDKSLGEKAPLRLHSEKPECRISAICSPRDSMYQSVCLISEE
RNECVIATEV

Human Notch1 cDNA sequence (CR457221.1)

SEQ ID NO: 9

```
   1  atgtcaaaca tgagatgtgt ggactgtggc acttgcctgg gtcacacacg gaggcatcct
  61  acccttttct ggggaaagac actgcctggg ctgaccccgg tggcggcccc agcacctcag
 121  cctgcacagt gtcccccagg ttccgaagaa gatgctccag caacacagcc tgggccccag
 181  ctcgcgggac ccgaccccc gtgggctccc gtgttttgta ggagacttgc cagagccggg
 241  cacattgagc tgtgcaacgc cgtgggctgc gtcctttggt cctgtccccg cagccctggc
 301  aggggcatg cggtcgggca ggggctggag ggaggcgggg gctgcccttg gccaccct
 361  cctagtttgg gaggagcaga ttttgcaat accaagtata gcctatggca gaaaaatgt
 421  ctttaa
```

Human Notch1 protein sequence (CR457221.1)

SEQ ID NO: 10

MSNMRCVDCGTCLGHTRRHPTLFWGKTLPGLTPVAAPAPQPAQCPPGSEEDAPATQPGPQLAGPDPPWAPVFCRR
LARAGHIELCNAVGCVLWSCPRSPGRGHAVGQGLEGGGGCPWATPPSLGGADFCNTKYSLWQKKCL

EXAMPLES

The invention will be further clarified by the following examples, which are intended to be purely exemplary of the invention and are in no way limiting.

Example 1—Design of New Compounds

Maintaining unaltered the core SR8278 scaffold and the ester substituent, we first designed compounds 1-3 in which the thiophene ring was replaced by a substituted benzene ring. The analysis and characterization of these compounds drove the design of subsequent compounds: 4-5 with alkoxy chains, 6-10 with simple heteroaromatic 5-member rings and 11-13 with hindered heteroaromatic 5-member rings. The synthesis of these compounds, together with their characterisation, is described in the relevant sections below. All compounds were synthesised and studied as racemates (as is consistent with the literature on SR8278 and derivatives).

Scheme 1: General synthesis of compounds 1-13

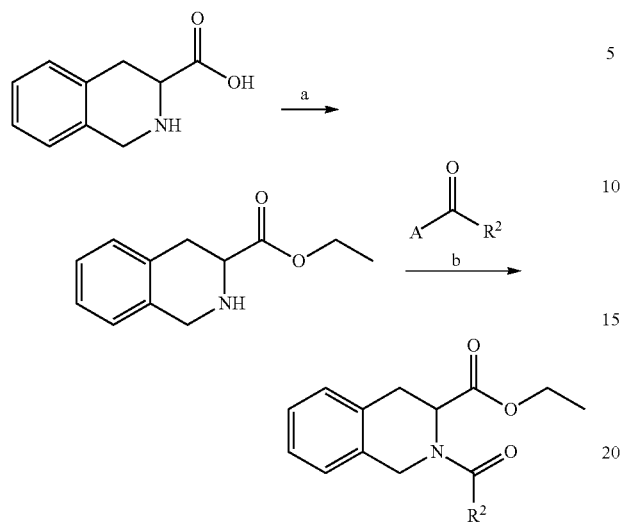

| Compound | R2 |
|---|---|
| 1 | 3,4-dichlorophenyl |
| 2 | 3,4-difluorophenyl |
| 3 | 4-fluorophenyl |
| 4 | ethoxy (OEt) |
| 5 | tert-butoxy (OtBu) |
| 6 | 2-thienyl |
| 7 | 2-furyl |
| 8 | 5-isoxazolyl |
| 9 | 5-oxazolyl |
| 10 | 5-thiazolyl |
| 11 | 4-methyl-5-oxazolyl |
| 12 | 4-methyl-5-thiazolyl |
| 13 | 4-methyl-2-phenyl-5-thiazolyl |

Reaction conditions: (a) EtOH, conc. $H_2SO_4$, reflux, overnight. (b) For A=Cl, TEA, DCM, rt, overnight; for A=OH, EDC, HOBt, TEA, DMF, rt, overnight.

Ethyl ester 14 was obtained following a similar procedure to the one described for the preparation of 1, by esterification of the carboxylic acid in methanol (MeOH) using sulfuric acid as catalyst, and condensation of intermediate 16 with 3,4-dichlorobenzoyl chloride using TEA as a base. Compound 15 was prepared starting from 1. Hydrolysis of the ester group was performed using basic conditions and introduction of the amide group was achieved by an EDC/HOBt coupling with ethanolamine, as previously described.

Scheme 2: Synthesis of compounds 14 and 15

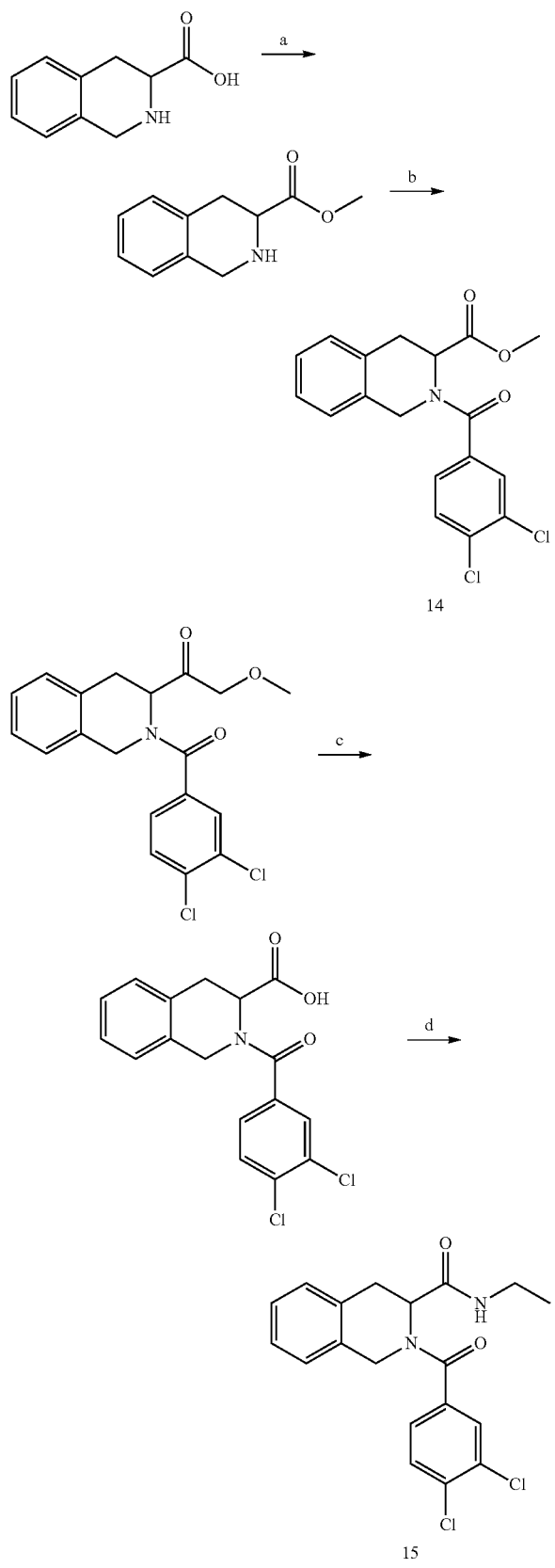

Synthesis conditions: (a) MeOH, H$_2$SO$_4$, reflux overnight: (b) 3,4-dichlorobenzoyl chloride, TEA, DMC, rt, overnight: (c) NaOH 2.0 M, MeOH:H2O (80:20), rt, 4 h; (d) Ethylamine, EDC, HOBt, TEA, DMF, rt, overnight.

Compounds 16 to 63 and 76 were obtained according to Scheme 3.

Scheme 3: Synthesis of compounds 16 to 63 and 76

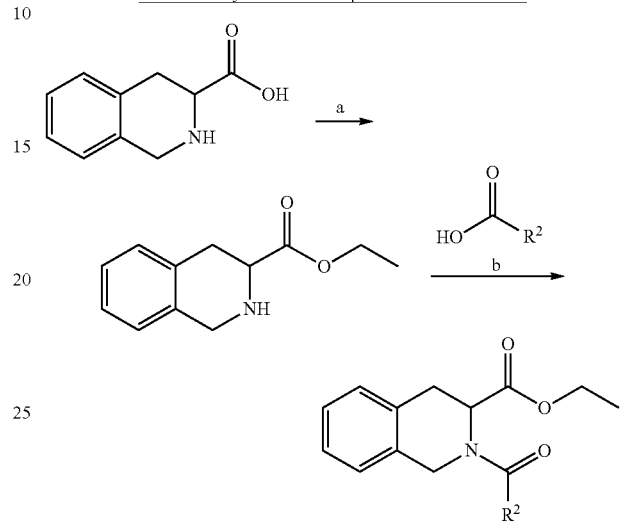

Reaction conditions: (a) EtOH, conc. H$_2$SO$_4$, reflux, 16 hours. (b) T$_3$P, DIPEA, THF, rt, 16 hours.

Compounds 64 to 75 were obtained according to Scheme 4.

Scheme 4: General synthesis of compounds 64 to 75

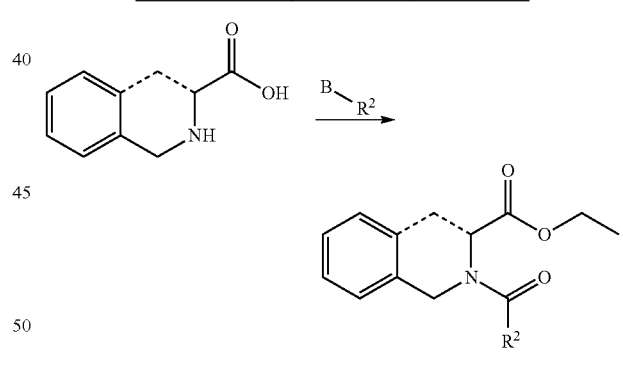

Reaction conditions: for B=—OC(O)Cl or —NCO (i.e. for 64 to 66 and 70), DCM, TEA, rt, 18 hours; for B=—COOH (i.e. for 67, 69, 71, 72 and 75), EDC, HOBt, TEA, DMF, rt, 18 hours; for B=—C(O)H (i.e. for 68, 73 and 74), AcOH, NaBH(OAc)$_3$, DCE or DCM, rt, 72 hours.

Ethyl 1,2,3,4-tetrahydroIsoquinoline-3-carboxylate, Intermediate (Int.)

A solution of 1,2,3,4-tetrahydroisoquinoline-3-carboxylic acid (1.00 g, 4.68 mmol) in anhydrous ethanol (25 mL) at room temperature (rt) and under N2 atmosphere was treated with cc. H$_2$SO$_4$ (1.00 ml, 7.15 mmol) and the reaction mixture was stirred under reflux for 18 h in the presence of molecular sieves 4 Å. The solvent was removed under vacuo and the residue resuspended in ethyl acetate (EtOAc) (30 mL) and washed with saturated NaHCO₃ (aq, 3×15 mL) and brine (3×15 ml), dried (MgSO₄), filtered, and evaporated under reduced pressure. The crude was purified by chromatography (n-Hex to EtOAc, 3:1, Rf: 0.51) to yield Int. as a yellow oil (650 mg, 67%). 1H-NMR (CDCl₃) δ=7.20-7.12 (m, 3H, Ar), 7.09-7.04 (m, 1H, Ar), 4.26 (q, J=7.1, 2H, H₂), 4.17 (d, J=16.2, 1H, H$_{12i}$), 4.11 (d, J=16.2, 1H, H$_{12ii}$), 3.76 (dd, J=10.2, 4.6, 1H, H₄), 3.12 (dd, J=18.0, 16.2, 1H, H$_{Si}$), 2.98 (dd, J=18.0, 16.2, 1H, H$_{Sii}$), 2.13 (s, 1H, NH), 1.33 (t, J=7.1, 3H, H1); ¹³C/ppm (CDCl₃) δ=173.21 (C₃), 135.90, 133.82, 129.34, 126.38, 126.26, 126.20, 60.68 (C₂), 55.55 (C₄), 46.97 (C₁₂), 31.50 (C₅), 14.57 (C₁); LC-MS (20-98% MeCN) rt=1.73 min; m/z 206.29 ([M+H]⁺); HRMS (m/z): calcd for [M+H]⁺ C₁₂H₁₆NO₂: 206.1181; found: 206.1175.

Ethyl 2-(3,4-dichlorobenzoyl)-1,2,3,4-tetrahydrolsoquinoline3-carboxylate, Compound 1

A solution of Int. (200 mg, 0.964 mmol) in DCM (20 ml) at 0° and under N₂ atmosphere was treated with TEA (0.20 mL, 1.4 mmol). To this mixture, a solution of 3,4-dichlorobenzoyl chloride (202 mg, 0.964 mmol) in DCM (5 ml) was added dropwise and the reaction mixture was allowed to warm to rt overnight. The solvent was removed under vacuo and the residue resuspended in ethyl acetate (EtOAc) (30 mL) and washed 1.0M HCl (2×15 mL), NaHCO₃ (3×15 ml) and brine (3×15 mL), dried (MgSO₄, filtered, and evaporated under reduced pressure. The crude was purified by chromatography (n-Hex to EtOAc, 5:1, Rf: 0.40) to obtain 1 as a white solid (225 mg; yield: 62%). Ratio of rotamers is 5.4:4, obtained from 1H NMR integrations at room temperature. 1H-NMR ((CD₃)2SO) Rotamer A δ=7.81 (d, J=8.2, 1H, H18), 7.72 (s, 1H, H15), 7.47 (d, J=8.2, 1H, H19), 7.33-7.09 (m, 4H, H7-10), 5.12 (t, J=5.3, 1H, H4), 4.59 (d, J=15.6, 1H, H12i), 4.52 (d, J=15.6, 1H, H12ii), 4.06 (q, J=7.0, 2H, H2), 3.28 (m, 2H, H5), 1.11 (t, J=7.0, 3H, H1). Rotamer B δ=7.76 (d, J=8.2, 1H, H18), 7.67 (s, 1H, H15), 7.40 (d, J=8.2, 1H, H19), 7.33-7.09 (m, 4H, H7-10), 4.97 (d, J=17.7, 1H, H12i), 4.80 (br, 1H, H4), 4.46 (d, J=17.7, 1H, H12ii), 3.98 (q, J=7.0, 2H, H2), 3.18 (m, 2H, H5), 1.00 (t, J=7.0, 3H, H1); 13C/ppm ((CD3)2SO) δ=170.27 (C3), 170.09 (C3), 168.56 (C13), 167.76 (C13), 136.38, 136.16, 133.11, 132.75, 132.49, 131.90, 131.61, 131.56, 131.10, 128.94, 128.62, 128.28, 127.81, 127.16, 126.77, 126.66, 126.54, 125.97, 61.20 (C2), 60.75 (C2), 56.21 (C4), 52.72 (C4), 47.45 (C12), 43.09 (C12), 30.66 (C5), 30.18 (C5), 13.95 (C1), 13.83 (C1); LC-MS (50-98% MeCN) rt=7.49 min; m/z 378.26 ([M+H]+); HRMS (m/z): calcd for [M+H]+ C19H18NO3Cl2: 378.0664; found: 378.0677.

Ethyl 2-(3,4-difluorobenzoyl)-1,2,3,4-tetrahydrolsoquinoline3-carboxylate, Compound 2

Compound 2 was prepared from Int. (500 mg, 2.41 mmol) according to procedure described for compound 1, using 3,4-difluorobenzoyl chloride (0.30 mL, 2.4 mmol). The crude was purified by chromatography (n-Hex to EtOAc, 5:1, Rf: 0.37) to obtain 2 as a pale-yellow oil that crystallizes with time (547 mg; yield: 66%). Ratio of rotamers is 5:4, obtained from 1H NMR integrations at room temperature. 1H-NMR ((CD3)2SO) Rotamer A δ=7.63-7.05 (m, 8H), 5.09 (t, J=5.3, 1H, H4), 4.58 (d, J=15.6, 1H, H12i), 4.51 (d, J=15.6, 1H, H12ii), 4.04 (q, J=6.9, 2H, H2), 3.25 (dd, J=15.8, 5.9, 2H, H5), 1.09 (t, J=7.0, 3H, H1). Rotamer B δ=7.63-7.05 (m, 8H), 4.95 (d, J=17.6, 1H, H12i), 4.78 (br, 1H, H4), 4.42 (d, J=17.7, 1H, H12ii), 3.96 (q, J=7.0, 2H, H2), 3.16 (m, 2H, H5), 0.97 (t, J=7.0, 3H, H1); 13C/ppm ((CD3)2SO) δ=170.34 (C3), 170.09 (C3), 168.84 (C13), 167.96 (C13), 150.35 (C16), 150.25 (C16), 148.39 (C17), 148.28 (C17), 133.17, 133.00, 132.78, 131.88, 131.65, 129.36, 128.32, 127.84, 127.46, 127.16, 126.66, 126.56, 125.94, 124.42, 123.94, 118.15, 118.01, 116.76, 116.62, 116.41, 116.27, 61.19 (C2), 60.73 (C2), 56.24 (C4), 52.78 (C4), 47.56 (C12), 43.12 (C12), 30.63 (C5), 30.21 (C5), 13.95 (C1), 13.81 (C1). LC-MS (50-98% MeCN) rt=7.31 min; m/z 346.22 ([M+H]+); HRMS (m/z): calcd for [M+H]+ C19H18NO3F2: 346.1255; found: 346.1264.

Ethyl 2-(4-fluorobenzoyl)-1,2,3,4-tetrahydrolsoquinoline-3-carboxylate, Compound 3

Compound 3 was prepared from Int. (330 mg, 1.59 mmol) according to procedure described for compound 1, using 4-fluorobenzoyl chloride (0.19 mL, 1.6 mmol). The crude was purified by chromatography (n-Hex to EtOAc, 3:1, Rf: 0.21) followed by a slow gradient of n-Hex:EtOAc on Isolera (2-98% EtOAc) to obtain 3 as a transparent oil that crystallizes with time (315 mg; yield: 61%). Ratio of rotamers is 5.4:4, obtained from 1H NMR integrations at room temperature. 1H-NMR ((CD3)2SO) Rotamer A δ=7.64-7.03 (m, 8H, Ar), 5.15 (t, J=4.7, 1H, H4), 4.62 (d, J=16.0, 1H, H12i), 4.54 (d, J=16.0, 1H, H12ii), 4.07 (q, J=6.7, 2H, H2), 3.28 (dd, J=15.8, 5.9, 2H, H5), 1.12 (t, J=6.7, 3H, H1). Rotamer B δ=7.64-7.03 (m, 8H, Ar), 5.01 (d, J=17.7, 1H, H12i), 4.78 (br, 1H, H4), 4.48 (d, J=17.7, 1H, H12ii), 3.97 (q, J=6.7, 2H, H2), 3.18 (m, 2H, H5), 0.99 (t, J=6.7, 3H, H1); 13C/ppm ((CD3)2SO) δ=170.47 (C3), 170.23 (C3), 170.14 (C13), 169.19 (C13), 133.25, 132.86, 131.84, 129.53, 129.11, 128.30, 127.88, 127.14, 126.66, 125.87, 115.76, 115.59, 61.14 (C2), 60.68 (C2), 56.33 (C4), 52.70 (C4), 47.67 (C12), 43.13 (C12), 30.75 (C5), 30.19 (C5), 13.96 (C1), 13.82 (C1). LC-MS (50-98% MeCN) rt=6.42 min; m/z 328.21 ([M+H]+); HRMS (m/z): calcd for [M+H]+ C19H19NO3F: 328.1349; found: 328.1349.

Diethyl 3,4-dihydroisoquinoline-2,3(1H)-dicarboxylate, Compound 4

Compound 4 was prepared from Int. (110 mg, 0.530 mmol) according to procedure described for compound 1, using ethyl chloroformate (0.05 mL, 0.5 mmol). The crude was purified by chromatography (n-Hex to EtOAc, 3:2, Rf: 0.36) to obtain 4 as a pale-yellow oil (235 mg; yield: 87%). Ratio of rotamers is 5:4, obtained from 1H NMR integrations at room temperature. 1H-NMR ((CD3)2SO) Rotamer A δ=7.24-7.07 (m, 4H, H7-10), 5.13 (dd, J=6.0, 3.2, 1H, H4), 4.77-4.73 (d, J=16.0, 2H, H12i), 4.57-4.53 (d, J=16.0, 2H, H12ii), 4.21 (m, 2, H14), 4.07 (m, 2H, H2), 3.28-3.15 (dd, J=38.0, 16.0, 2H, H5), 1.33 (t, J=7.1, 3H, H15), 1.11 (m, 3H, H1). Rotamer B δ=7.24-7.07 (m, 4H, H7-10), 4.90 (m, 1H, H4), 4.78-4.74 (d, J=16.0, 2H, H12i), 4.60-4.56 (d, J=16.0, 2H, H12ii), 4.21 (m, 2H, H14), 4.07 (m, 2H, H2), 3.27-3.13 (dd, J=38.0, 16.0, 2H, H5), 1.25 (t, J=7.1, 3H, H15), 1.11 (m, 3H, H1); 13C/ppm ((CD3)2SO) δ=167.59 (C3), 157.21 (C13), 144.65, 132.04, 129.82, 127.90, 127.13, 126.65, 68.56, 66.62, 61.13, 53.93 (C4), 44.59 (C12), 31.33 (C5), 14.41 (C15), 14.32 (C1). LC-MS (20-98% MeCN) rt=10.35 min; m/z 278.21 ([M+H]+); HRMS (m/z): calcd for [M+H]+ C15H2ONO4: 278.1392; found: 278.1396.

2-Tert-butyl 3-ethyl 3,4-dihydroisoquinoline-2,3(1H)-dicarboxylate, Compound 5

Compound 5 was prepared from Int (200 mg, 0.964 mmol) in dry THF (20 mL) using di-tert-butyl decarbonate (Boc anhydride) (252 mg, 1.15 mmol) and TEA (0.20 mL, 1.5 mmol). The reaction mixture was stirred at rt overnight under N2 atmosphere. The solvent was removed under vacuo and the residue resuspended in ethyl acetate (EtOAc) (30 mL) and washed with saturated NaHCO3 (aq, 3×15 mL) and brine (3×15 mL), dried (MgSO4), filtered, and evaporated under reduced pressure. The crude was purified by chromatography (n-Hex to EtOAc, 5:1, Rf: 0.56) to yield 5 as a transparent oil (233 mg; yield: 79%). Ratio of rotamers is 5:4, obtained from 1H NMR integrations at room temperature. 1H-NMR ((CD3)2SO) Rotamer A δ=7.37-6.97 (m, 4H, Ar), 4.72-4.64 (t, J=4.7, 1H, H4), 4.66-4.38 (m, 2H, H12), 4.06-4.01 (m, 2H, H2), 3.20-3.04 (dd, J=48.0, 15.1, 1H, H5i), 3.3.21-3.03 (dd, J=60.0, 12.1, 1H, H5ii), 1.39 (s, 9H, H15), 1.08 (t, J=7.1, 3H, H1). Rotamer B δ=7.37-6.97 (m, 4H, Ar), 4.91 (t, J=4.7, 1H, H4), 4.66-4.38 (m, 2H, H12), 4.01-3.95 (q, J=8.0, 4.0, 2H, H2), 3.14 (d, J=4.6, 2H, H5), 1.47 (s, 9H, H15), 1.06-1.01 (t, J=7.1, 3H, H1); 13C/ppm ((CD3)2SO) δ=171.95 (C3), 171.48 (C3), 155.08 (C13), 154.52 (C13), 134.44, 133.44, 133.08, 132.40, 128.57, 128.08, 127.33, 127.10, 126.65, 126.55, 80.24 (C14), 80.04 (C14), 61.03 (C2), 54.50 (C4), 52.95 (C4), 44.76 (C12), 44.15 (C12), 31.44 (C5), 31.22 (C5), 28.52 (C15), 28.35 (C15), 14.50 (C1), 14.40 (C1). LC-MS (20-98% MeCN) rt=7.59 min; m/z 306.31 ([M+H]+); HRMS (m/z): calcd for [M+H]+C17H24NO4: 306.1705; found: 306.1707.

Ethyl 2-(thiophene-2-carbonyl)-1,2,3,4-tetrahydrol-soquinoline-3-carboxylate, Compound 6

Compound 6 was prepared from Int. (230 mg, 1.11 mmol) according to procedure described for compound 1, using 2-thiophene carbonyl chloride (0.13 ml, 1.2 mmol). The crude was purified by chromatography (n-Hex to EtOAc, 3:1, Rf: 0.31) followed by a reverse phase Isolera with a slow gradient of H2O:MeCN (2-98% MeCN) (271 mg; yield: 77%) to obtain 6 as a yellow oil (145 mg; yield: —). Ratio of rotamers is 5:4, obtained from 1H NMR integrations at room temperature. 1HNMR ((CD3)2SO) degrades very quickly, not possible to assess NMR; 13C/ppm ((CD3)2SO) degrades very quickly, not possible to assess NMR. LC-MS (20-98% MeCN) rt=11.09 min; m/z 316.19 ([M+H]+); HRMS (m/z): calcd for [M+H]+ C17H18NO3S: 316.1007; found: 316.1016.

Ethyl 2-(furan-2-carbonyl)-1,2,3,4-tetrahydrolsoqui-noline-3-carboxylate, Compound 7

A solution of 2-furoic acid (161 mg, 1.44 mmol) in DMF (20 mL) was treated with TEA (0.27 mL, 1.9 mmol), EDC coupling agent (257 mg, 1.34 mmol) and HOBt (181 mg, 1.34 mmol) and left stirring at rt for 5 min. To this mixture, Int. (200 mg, 0.960 mmol) was added and the reaction mixture was left stirring rt overnight under N2 atmosphere. 60 mL of dH2O were added to quench the reaction and the product was extracted with EtOAc (3×15 ml). All organic fractions were mixed together and washed with LiCl 5% (3×15 mL) to eliminate traces of DMF, NaHCO3 (3×15 mL) and brine (3×15 ml), dried (MgSO4), filtered, and evaporated under reduced pressure. The crude was purified by chromatography (n-Hex to EtOAc, 3.5:1, Rf: 0.22) to obtain 7 as a pale-yellow oil (266 mg; yield: 93%). Ratio of rotamers was not possible to asses as the signals appeared in coalescence on 1H NMR at room temperature. 1HNMR ((CD3)2SO) δ=8.16-7.77 (d, J=44.0, 1H, H15), 7.37-7.00 (m, 5H, H7-10, H16),), 6.69 (d, J=22.3, 1H, H17), 5.44 (br, 0.35H, H4b), 5.13 (br, 0.65H, H4a), 5.11-5.07 (d, J=16.0, 0.6H, H12ai), 4.93-4.89 (d, J=16.0, 0.6H, H12aii), 4.83-4.79 (d, J=16.0, 0.4H, H12bi), 4.59-4.55 (d, J=16.0, 0.4H, H12bii), 4.00 (m, 2H, H2), 3.24 (br, 2H, H5), 1.02 (s, 3H, H1); 13C/ppm ((CD3)2SO) δ=171.30 (C3), 170.92 (C3), 159.86 (C13), 159.67 (C13), 147.67, 147.05, 146.03, 145.66, 133.65, 133.20, 132.87, 132.76, 128.26, 127.53, 127.24, 126.89, 126.61, 117.35 (C17), 116.87 (C17), 112.06 (C16), 61.38 (C2), 61.09 (C2), 55.92 (C4), 53.49 (C4), 47.09 (C12), 44.46 (C12), 32.11 (C5), 30.99 (C5), 14.37 (C1); LC-MS (20-98% MeCN) rt=4.16 min; m/z 300.33 ([M+H]+); HRMS (m/z): calcd for [M+H]+ C17H18NO4: 300.1236; found: 300.1247.

Ethyl 2-(isoxazole-5-carbonyl)-1,2,3,4-tetrahydrol-soquinoline3-carboxylate, Compound 8

Compound 8 was prepared from Int. (375 mg, 1.82 mmol) according to procedure described for compound 1, using 5-carbonyl chloride (0.31 mL, 1.5 mmol). The crude was purified by chromatography (n-Hex to EtOAc, 1:1, Rf: 0.73 and n-Hex to EtOAc, 3:1, Rf: 0.24) to obtain 8 as a pale-yellow oil (395 mg; yield: 69%). Ratio of rotamers is 4.7:4, obtained from 1H NMR integrations at room temperature. 1H-NMR ((CD3)2SO) Rotamer A δ=8.82 (d, J=32.9, 1H, H16), 7.34-7.21 (m, 4H, H7-10), 7.09 (d, J=71.4, 1H, H15), 5.20 (m, 1H, H4), 4.93-4.89 (d, J=15.7, 1H, H12i), 4.83-4.79 (d, J=15.7, 1H, H12ii, 4.02 (m, 2H, H2), 3.26 (m, 2H, H5), 1.06 (t, J=7.1, 3H, H1). Rotamer B δ=8.82 (d, J=32.9, 1H, H16), 7.34-7.21 (m, 4H, H7-10), 7.09 (d, J=71.4, 1H, H15), 5.20 (m, 1H, H4), 4.84 (m, 1H, H12i), 4.65-4.61 (d, J=15.7, 1H, H12ii), 4.02 (m, 2H, H2), 3.26 (m, 2H, MRes Drug Discovery & Development 2017 H5), 0.99 (t, J=7.1, 3H, H1); 13C/ppm ((CD3)2SO) δ=170.66 (C3), 170.32 (C3), 162.68 (C13), 162.20 (C13), 158.74 (C14), 158.30 (C14), 151.67 (C15), 151.54 (C15), 133.10, 132.53, 132.33, 128.39, 128.27, 127.77, 127.45, 127.34, 126.99, 126.64, 107.90 (C16), 107.56 (C16), 61.67 (C2), 61.32 (C2), 56.07 (C4), 53.67 (C4), 46.97 (C12), 44.51 (C12), 31.84 (C5), 30.80 (C5), 14.37 (C1), 14.26 (C1). LC-MS (20-98% MeCN) rt=10.03 min; m/z 301.31 ([M+H]+); HRMS (m/z): calcd for [M+H]+ C16H16N2O4: 301.1188; found: 301.1189.

Ethyl 2-(oxazole-5-carbonyl)-1,2,3,4-tetrahydrolso-quinoline-3-carboxylate, Compound 9

Compound 9 was prepared from Int. (325 mg, 1.58 mmol) according to the EDC coupling procedure described for compound 7, using 1,3-oxazole-5-carboxylic acid (150 mg, 1.32 mmol). The crude was purified by chromatography (n-Hex to EtOAc, 1.5:1, Rf: 0.42) followed by a slow gradient of H2O:MeCN on reverse phase Isolera (2-98% MeCN) to obtain 9 as a transparent oil (320 mg; yield: 68%). Ratio of rotamers was difficult to assess since most of the signals appear in coalescence. Some of the peaks appear separate and indicate a ratio 7.6:4, obtained from 1H NMR integrations at room temperature. 1H-NMR ((CD3)2SO) Rotamer A δ=8.67 (s, 1H, H15), 8.03 (s, 1H, H16), 7.32-7.21 (m, 4H, H7-10), 5.20 (t, J=5.3, 1H, H4), 5.04 (d, J=15.4, 1H, H12i), 4.92 (d, J=15.5, 1H, H12ii), 4.06-3.95 (m, 2H, H2), 3.23 (br, 2H, H5), 1.01 (br, 3H, H1). Rotamer B δ=8.59 (s, 1H, H15), 7.75 (s, 1H, H16), 7.32-7.21 (m, 4H, H7-10), 5.40 (br, 1H, H4), 4.83 (d, J=17.2, 1H, H12i), 4.59 (d, J=17.2, 1H, H12ii), 4.06-3.95 (m, 2H, H2), 3.27 (br, 2H, H5), 1.01 (br, 3H, H1); 13C/ppm ((CD3)2SO) δ=170.99 (C3), 170.63 (C3), 158.75 (C13), 158.29 (C13), 154.28 (C15), 153.78 (C15), 144.89 (C14), 144.46 (C14), 133.19, 133.00, 132.74, 132.01, 131.36, 128.28, 127.60, 127.28, 126.94, 126.74, 61.57 (C2), 61.18 (C2), 55.82 (C4), 53.36 (C4), 46.81 (C12), 44.41 (C12), 31.96 (C5), 30.98 (C5), 14.53 (C1), 14.34 (C1). LC-MS (20-98% MeCN) rt=8.95 min; m/z 301.31 ([M+H]+); HRMS (m/z): calcd for [M+H]+ C16H16N2O4: 301.1188; found: 301.1201.

Ethyl 2-(thiazole-5-carbonyl)-1,2,3,4-tetrahydrolsoquinoline3-carboxylate, Compound 10

Compound 10 was prepared from Int. (286 mg, 1.39 mmol) according to the EDC coupling procedure described for compound 7, using 1,3-thiazole-5-carboxylic acid (150 mg, 1.16 mmol). The crude was purified by chromatography (n-Hex to EtOAc, 2:3, Rf: 0.37) to obtain 10 as a transparent oil (125 mg; yield: 35%). Ratio of rotamers was not possible to assess since peaks appear in coalescence in 1H NMR at room temperature. 1H-NMR ((CD3)2SO) δ=9.32 (s, 1H, H15), 8.56-8.06 (m, 1H, H16), 7.29-7.18 (m, 4H, H7-10), 5.19 (s, 1H, H4), 4.96 (m, 1.7H, H12a, H12bi), 4.53 (d, J=13.6, 0.3H, H12bii), 4.01 (q, J=8, 2H, H2), 3.24 (br, 2H, H5), 1.10 (br, 3H, H1); 13C/ppm ((CD3)2SO) δ=163.01 (C3), 162.10 (C3), 158.23 (C13), 157.49 (C13), 145.06 (C15), 143.68 (C15), 133.38, 133.05, 132.52, 129.36, 128.66, 128.27, 127.60, 127.24, 126.74, 125.77, 61.73 (C2), 61.19 (C2), 57.04 (C4), 53.86 (C4), 48.08 (C12), 44.45 (C12), 31.58 (C5), 31.02 (C5), 14.35 (C1). LC-MS (20-98% MeCN) rt=9.38 min; m/z 317.23 ([M+H]+); HRMS (m/z): calcd for [M+H]+ C16H17N2O3S: 317.0960; found: 317.0968.

Ethyl 2-(4-methyloxazole-5-carbonyl)-1,2,3,4-tetrahydrolsoquinoline-3-carboxylate, Compound 11

Compound 11 was prepared from Int. (291 mg, 1.42 mmol) according to the EDC coupling procedure described for compound 7, using 4-methyloxazole-5-carboxylic acid (150 mg, 1.52 mmol). The crude was purified by chromatography (nHex to EtOAc, 1:1, Rf: 0.20) to obtain 11 as a transparent oil (216 mg; yield: 58%). Ratio of rotamers was difficult to assess since most of the signals appear in coalescence. Some of the peaks appear separate and indicate a ratio 4.7:4, obtained from 1H NMR integrations at room temperature. 1H-NMR ((CD3)2SO) δ=8.53 (s, 0.55H, H15a), 8.42 (s, 0.45H, H15b), 7.23 (br, 4H, H7-10), 5.26 (br, 0.45H, H4b), 5.07 (br, 0.55H, H4a), 4.92 (d, J=16.0, 0.45H, H12bi), 4.80 (m, 1.1H, H12a), 4.56 (d, J=16.0, 0.45H, H12bii), 4.03 (br, 2H, H2), 3.25 (m, 2H, H5), 2.33 (s, 3H, H17), 1.08-0.99 (m, 3H, H1); 13C/ppm ((CD3)2SO) δ=171.45 (C3), 170.74 (C3), 159.74 (C13), 158.01 (C13), 152.21 (C15), 151.92 (C15), 139.86, 139.39, 134.59, 134.08, 132.98, 132.44, 129.35, 128.65, 128.28, 127.89, 127.59, 127.23, 125.76, 61.23 (C2), 55.74 (C4), 53.53 (C4), 46.67 (C12), 44.38 (C12), 32.04 (C5), 30.74 (C5), 14.35 (C1), 13.18 (C17). LC-MS (20-98% MeCN) rt=9.55 min; m/z 315.28 ([M+H]+); HRMS (m/z): calcd for [M+H]+ C17H19N2O4: 315.1345; found: 315.1352.

Ethyl 2-(4-methylthiazole-5-carbonyl)-1,2,3,4-tetrahydrolsoquinoline-3-carboxylate, Compound 12

Compound 12 was prepared from Int. (257 mg, 1.25 mmol) according to the EDC coupling procedure described for compound 7, using 4-methylthiazole-5-carboxylic acid (150 mg, 1.04 mmol). The crude was purified by chromatography (nHex to EtOAc, 2:3, Rf: 0.43) to obtain 12 as a transparent oil (196 mg; yield: 60%). Ratio of rotamers was difficult to assess since most of the signals appear in coalescence. Some of the peaks appear separate and indicate a ratio 7.2:4, obtained from 1H NMR integrations at room temperature. 1H-NMR ((CD3)2SO)=9.18 (s, 1H, H15), 7.22 (m, 4H, H7-10), 5.16 (br, MRes Drug Discovery & Development 2017 0.65H, H4a), 4.97 (d, J=15.5, 0.35H, H12bi), 4.84 (s, 0.35H, H4b), 4.56 (br, 1.65H, H12a+H12bii), 4.03 (br, 2H, H2), 3.22 (m, 2H, H5), 2.46 (br, 3H, H17), 1.11 (m, 3H, H1); 13C/ppm ((CD3)2SO) δ=170.67 (C3), 163.66 (C13), 154.96, 152.47, 133.41, 132.09, 128.34, 127.72, 127.19, 126.49, 124.79, 61.39 (C2), 53.52 (C4), 47.43 (C12), 30.58 (C5), 16.25 (C17), 14.39 (C1). LC-MS (20-98% MeCN) rt=9.59 min; m/z 330.94 ([M+H]+); HRMS (m/z): calcd for [M+H]+ C17H19N2O3S: 331.1116; found: 331.1130.

Ethyl 2-(4-methy-2-phenylthiazole-S-carbonyl)-1,2,3,4-tetrahydrolsoquinoline-3-carboxylate, Compound 13

Compound 13 was prepared from Int. (240 mg, 1.17 mmol) according to the EDC coupling procedure described for compound 7, using 4-methy-2-phenylthiazole-5-carboxylic acid (213 mg, 0.974 mmol). The crude was purified by chromatography (n-Hex to EtOAc, 5:2, Rf: 0.32) to obtain 13 as an orange oil (298 mg; yield: 75%). Ratio of rotamers was not possible to asses as the signals appeared in coalescence on 1H NMR at room temperature. 1H-NMR ((CD3)2SO)=7.97 (br, 2H, H17+H21), 7.53 (m, 3H, H18-20), 7.23 (m, 4H, H7-10), 5.15-5.54 (m, 3H, H4+H12), 4.06 (br, 2H, H2), 3.24 (m, 2H, H5), 2.48 (s, 3H, H23), 1.11 (br, 3H, H1); 13C/ppm ((CD3)2SO) δ=170.60 (C3), 167.22 (C15), 153.10 (C13), 132.83, 131.30, 129.82, 128.40, 127.19, 126.75, 61.47 (C2), 53.57 (C4), 47.60 (C12), 30.68 (C5), 16.59 (C23), 14.40 (C1). LC-MS (20-98% MeCN) rt=12.85 min; m/z 407.44 ([M+H]+); HRMS (m/z): calcd for [M+H]+ C23H23N2O3S: 407.1429; found: 407.1418.

Methyl 2-(3,4-dichlorobenzoyl)-1,2,3,4-tetrahydrolsoquinoline-3-carboxylate, Compound 14

Compound 14 was prepared from an intermediate after an esterification of 1,2,34-tetrahydroisoquinoline carboxylic acid (150 mg, 0.702 mmol) in methanol (10 ml) following the procedure described for Int. 16 was used without further purification (90 mg, 0.47 mmol) following the previously described procedure for compound 1, using 3,4-chlorobenzoyl chloride (98 mg, 0.47 mmol). The crude was purified by chromatography (n-Hex to EtOAc, 2:1, Rf: 0.54) to obtain 14 as a white powder (123 mg; yield: 73%). Ratio of rotamers is 5.4:4, obtained from 1H NMR integrations at room temperature. 1HNMR ((CD3)2SO) Rotamer A δ=7.8 (d, J=8.2, 1H, H18), 7.71 (s, 1H, H14), 7.47 (d, J=8.1, 1H, H17), 7.28-7.10 (m, 4H, H6-9), 5.17 (t, J=8, 1H, H3), 4.56 (dd, J=24.0, 16.0, 2H, H11), 3.62 (s, 3H, H1), 3.28 (dd, J=16.0, 6.1, 2H, H4). Rotamer B δ=7.74 (d, J=8.2, 1H, H18), 7.69 (s, 1H, H14), 7.40 (d, J=8.1, 1H, H17), 7.28-7.10 (m, 4H, H6-9), 5.01 (d, J=17.7, 1H, H11i), 4.84 (br, 1H, H3), 4.42 (d, J=17.7, 1H, H11ii), 3.53 (s, 3H, H1), 3.22-3.12 (m, 2H, H4); 13C/ppm ((CD3)2SO) δ=171.32 (C2), 171.14 (C2), 169.03 (C12), 168.26 (C12), 136.76, 136.58, 133.47, 133.28, 133.16, 132.26, 132.08, 131.56, 129.46, 129.17, 128.81, 128.36, 127.67, 127.15, 126.45, 56.64 (C3), 55.36 (C3), 53.05 (C1), 52.70 (C1), 47.88 (C11), 43.40 (C11), 30.95 (C4), 30.52 (C4). LC-MS (20-98% MeCN) rt=12.44 min; m/z 364.28 ([M+H]+); HRMS (m/z): calcd for [M+H]+ C18H16NO3Cl2: −364.0507; found: 364.0499.

2-(3,4-Dichlorobenzoyl)-1,2,3,4-tetrahydroisoquinoline-3-carboxylic acid, Intermediate 17

Intermediate 17 was prepared from compound 1 (250 mg, 0.663 mmol) following a hydrolysed under basic conditions. 1 is dissolved in MeOH:H2O (80:20) (15 ml) and NaOH 2.0 M (7.5 ml) was added dropwise to the mixture. The reaction mixture was left stirring at rt for 5 h. The solvent was removed under vacuum and the residue was resuspended in water (30 mL). The mixture was acidified to pH 4 with HCl 1.0 M and the product was extracted with EtOAc (3×15 ml) and washed with brine (3×15 mL), dried (MgSO4), filtered, and solvent was evaporated under reduced pressure. 17 was obtained as a white solid (230 mg; yield: 100%) used without further purification. Ratio of rotamers is 1:1, obtained from 1H NMR integrations at room temperature 1H-NMR ((CD3)2SO) Rotamer A δ=12.98 (s, 1H, OH), 7.78 (d, J=15.7, 1H, H16), 7.68 (s, 1H, H13), 7.44 (d, J=23.0, 1H, H17), 7.31-7.08 (m, 4H, H5-8), 5.14 (t, J=4.8, 1H, H2), 4.54 (s, 2H, H10), 3.27-3.09 (m, 2H, H3). Rotamer B δ=12.98 (s, 1H, OH), 7.76 (d, J=15.7, 1H, H16), 7.66 (s, 1H, H13), 7.42 (d, J=23.0, 1H, H17), 7.31-7.08 (m, 4H, H5-8), 4.97 (d, J=17.7, 1H, H10i), 4.68 (br, 1H, H2), 4.48 (d, J=17.7, 1H, H10ii), 3.27-3.09 (m, 2H, H3); LC-MS (50-98% MeCN) rt=4.99 min; m/z 350.25 ([M+H]+); HRMS (m/z): calcd for [M+H]+C17H14NO3Cl2: 350.0351; found: 350.0356.

2-(3,4-Dichlorobenzoyl)-N-ethyl-1,2,3,4-tetrahydrolsoquinoline-3-carboxamide, Compound 15

Compound 15 was prepared form intermediate 17 A solution of 17 (100 mg, 0.286 mmol) in DMF (15 mL) was treated with TEA (0.080 mL, 0.57 mmol), EDC coupling agent (76.5 mg, 0.400 mmol) and HOBt (54.1 mg, 0.400 mmol) and left stirring at rt for 5 min. To this mixture, Ethylamine 2.0 M (0.17 MRes Drug Discovery & Development 2017 mL, 0.34 mmol) was added and the reaction mixture was left stirring rt overnight under N2 atmosphere. 40 mL of dH2O were added to quench the reaction and the product was extracted with EtOAc (3×15 mL). All organic fractions were mixed together and washed with LiCl 5% (3×15 ml) to eliminate traces of DMF, NaHCO3 (3×15 ml) and brine (3×15 ml), dried (MgSO4), filtered, and evaporated under reduced pressure. The crude was purified by chromatography (n-Hex to EtOAc, 1:1, Rf: 0.26) to obtain 15 as a pale-yellow oil (74 mg; yield: 69%). Ratio of rotamers is 5.4:4, obtained from 1H NMR integrations at room temperature. 1H-NMR ((CD3)2SO) Rotamer A δ=7.94 (t, J=5.5, 1H, NH), 7.79 (s, 1H, H15), 7.77 (d, J=8.1, 1H, H19), 7.49 (d, J=7.8, 1H, H18), 7.24-7.05 (m, 4H, H7-10), 4.88 (br, 1H, H4), 4.50 (m, 2H, H12), 3.11 (m, 2H, H5), 3.03 (q, J=4.0, 2H, H2), 0.90 (t, J=6.7, 3H, H1). Rotamer B δ=7.94 (t, J=5.5, 1H, NH), 7.72 (d, J=8.1, 1H, H19), 7.62 (s, 1H, H15), 7.36 (d, J=7.8, 1H, H18), 7.24-7.05 (m, 4H, H7-10), 4.96 (d, J=17.1, 1H, H12i), 4.56 (m, 1H, H12ii), 4.36 (br, 1H, H4), 3.11 (m, 2H, H5), 2.92 (m, 2H, H2), 0.81 (t, J=6.7, 3H, H1); 13C/ppm ((CD3)2SO) δ=169.45 (C3), 169.14 (C3), 168.27 (C13), 167.97 (C13), 137.09, 136.64, 133.67, 133.47, 132.60, 132.44, 132.30, 132.17, 131.29, 130.98, 130.85, 129.23, 128.37, 128.03, 127.77, 127.48, 127.05, 126.70, 126.48, 126.34, 125.80, 56.88 (C4), 53.60 (C4), 47.68 (C12), 43.49 (C12), 33.53 (C2), 33.45 (C2), 31.64 (C5), 30.74 (C5), 14.73 (C1), 14.56 (C1); LC-MS (20-98% MeCN) rt=10.87 min; m/z 377.18 ([M+H]+); HRMS (m/z): calcd for [M+H]+ C19H19N2O2Cl2: 377.0824; found: 377.0821.

Example 2—Screening of Compounds for REV-ERBα Antagonist Activity

HEK293T cells were defrosted and maintained in DMEM supplemented with 10% FCS and 1% P/S at 37° C. and 5% $CO_2$. Cells were plated in a 24-well plate (7·10⁴ cells/well in 0.5 mL of DMEM+10% FCS). 24 h after seeding, cells were transfected with 100 ng of Bmal-luc, 10 ng of pRL-CMV Renilla as an internal control and 10 ng of REV-ERBα or the empty vector pcDNA3 as a control. All conditions were equalled to a total of 400 ng of DNA by using BSM. In order to prepare transfection samples, calculated amounts of DNA needed for each condition were prepared in Opti-MEM and Fugene was added in a 5:2 Fugene:DNA ratio. Mixtures were vortexed to assure homogeneity and left to incubate for 15 min at rt. Afterwards, each DNA mix was transferred into the 24-well plate containing the pre-seeded cells, with each condition repeated by triplicate. 5 h after transfection, cells were treated with compounds 2-12, AG1-AG5 or DMSO as vehicle. Solution of the compounds in DMEM were prepared at a double concentration than the final desired one, and 0.5 mL of these solutions were added to each well. 24 h after transfection, cells were lysed and luciferase activity was measured using Dual-Luciferase Reporter Assay System E2920 (Promega). To perform the experiment, cells were lysed by adding 50 µL of passive lysis buffer (PLB) (1:5 dilution) to each well and gently stirring for 30 min. Each cell lysate was transferred to a 96-well plate. 50 µL of Dual-Glo reagent were dispensed into each well, tapped gently to mix and incubated for 10 min. Luminescence of firefly luciferase was measured using a Tecan VICTOR Light Luminescent counter equipment. Then, 50 µL of Stop&Glo reagent were dispensed to quench firefly activity and activate Renilla luciferase, incubated for 10 min and measured. Firefly activity was normalized to Renilla luciferase activity. Results were analysed using Welch's corrected parametric t-test.

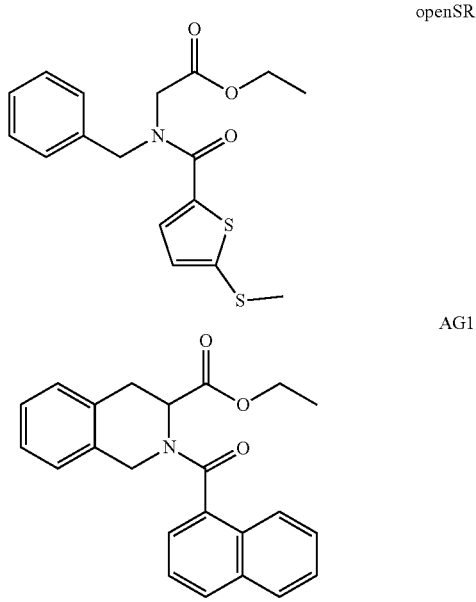

openSR

AG1

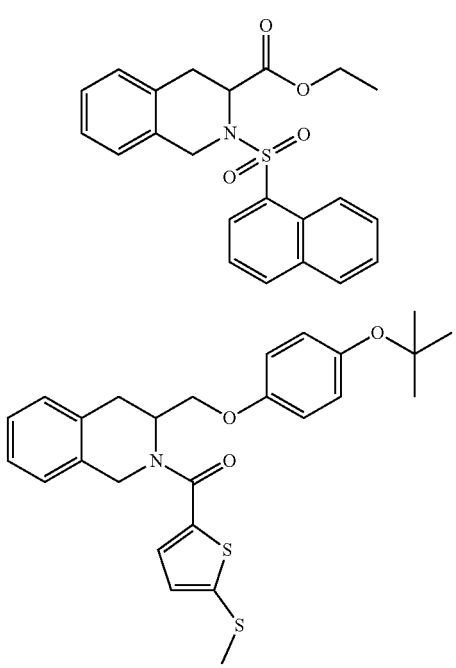

2. The resulting data are shown in FIG. 3, expressed as the average and standard error obtained from three independent experiments carried out in triplicate.

Figure 3:
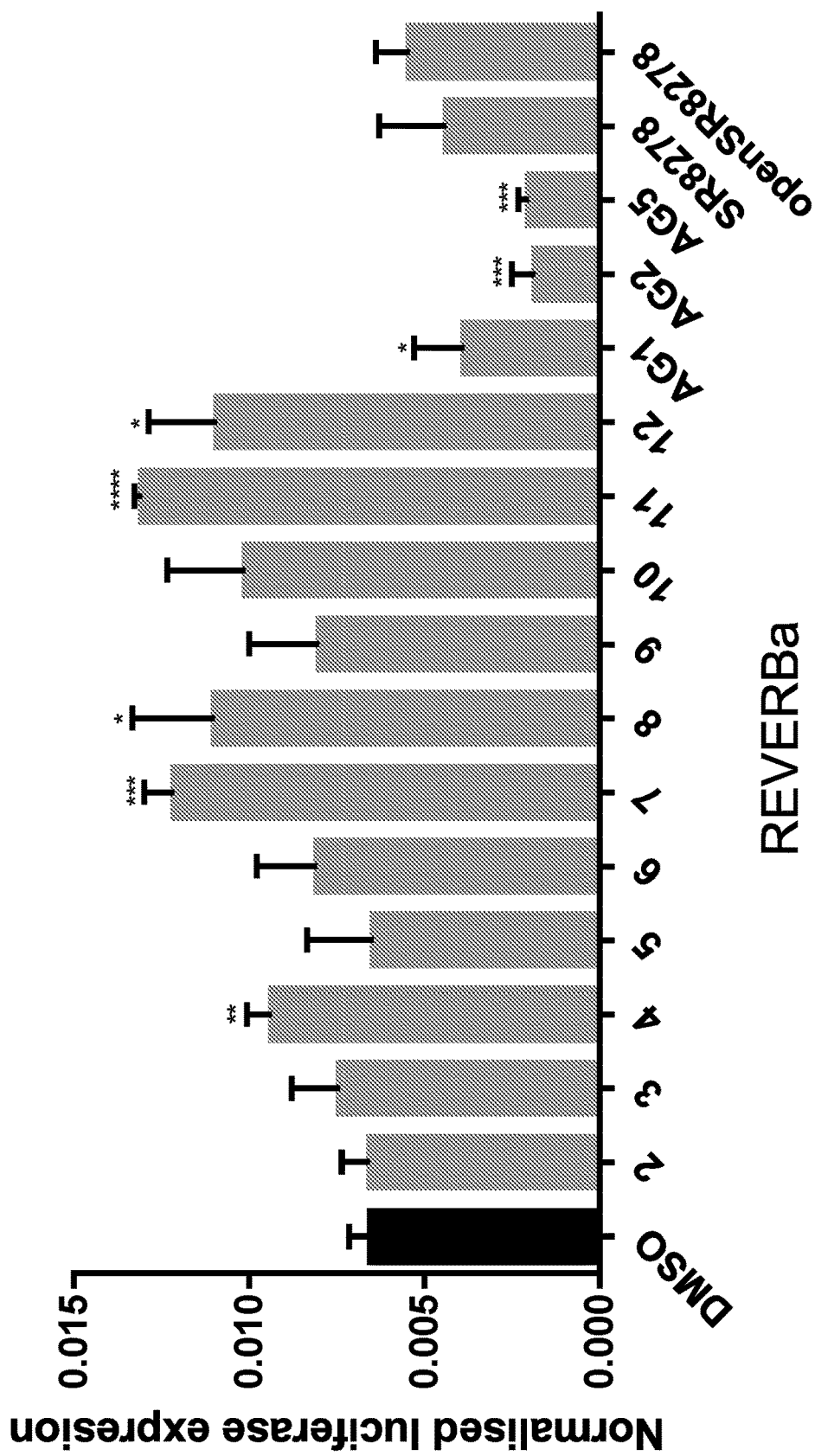
FIG. 3: Effect of newly generated compounds on REV-ERBa activity. Dual-luciferase result for drug screening using 10 ng $Renilla$, 100 ng Bmal-luc, 10 ng REV-ERBa and 280 ng BSM. Compounds were tested at 10 µM concentration. Compounds 4, 7, 8, 11 and 12 show significant antagonistic activity, increasing Bmal-luc expression, while compounds AG1, AG2 and AG5 are agonists, reducing the signal of Bmal-luc. (* for $p<0.05$,  for $p<0.01$, * for $p<0.001$ and **** for $p<0.0001$)

As is clear from FIG. 3, compounds 4, 7, 8, 11 and 12 all produced a significant increase in luciferase expression compared with SR8278 (* for $p<0.05$,  for $p<0.01$, * for $p<0.001$ and **** for $p<0.0001$), indicating that these are stronger REV-ERBα antagonists than SR8278.

Example 3—Screening of Further Compounds for REV-ERBα Antagonist Activity

The method of Example 2 was repeated using Compounds 70 to 72 (generated as described in Example 1). Compounds 4, 7 and 11 (tested in Example 2) were used as a positive control for REV-ERB inhibitory activity, agonist compound AG2 (also tested in Example 2) and DMSO were also tested as comparators.

Figure 4:
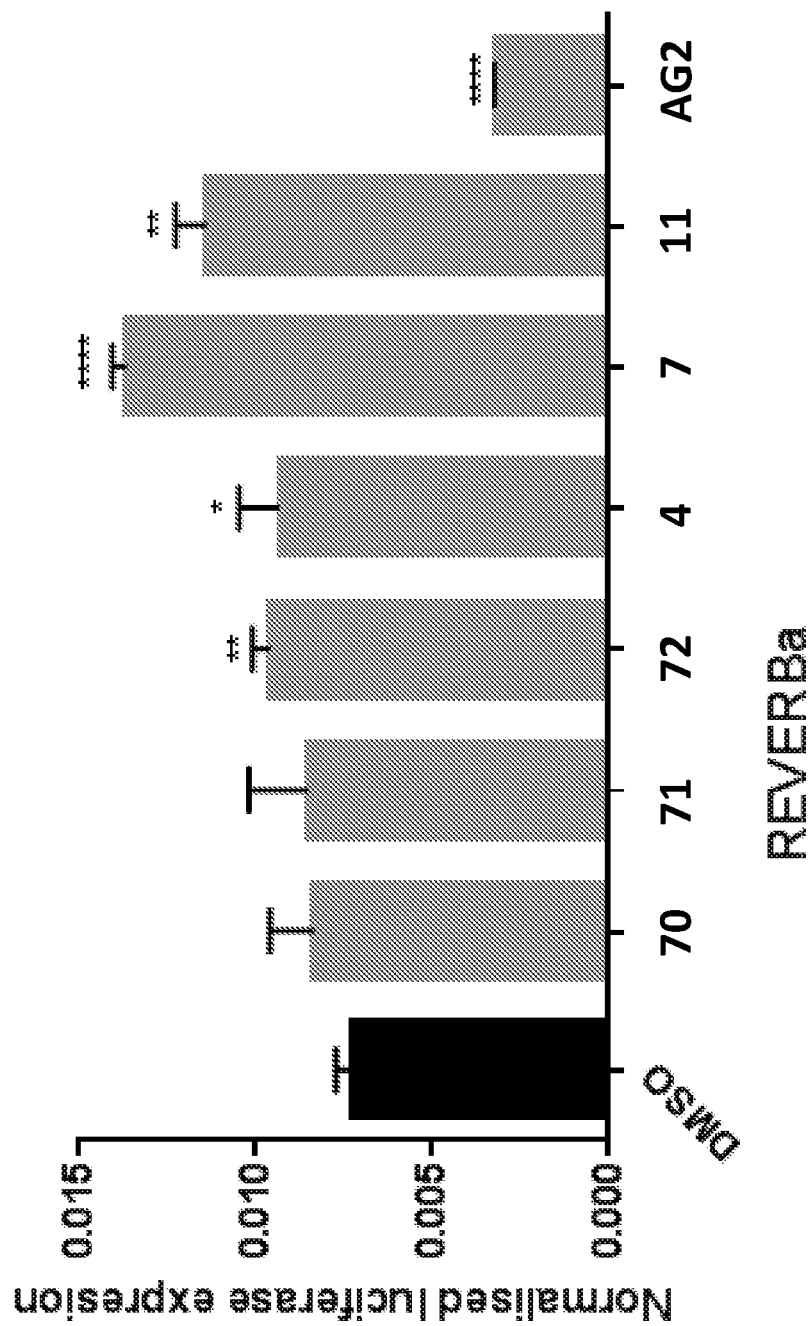
FIG. 4: Effect of further newly generated compounds on REV-ERBa activity. Dual-luciferase result for drug screening using 10 ng $Renilla$, 100 ng Bmal-luc, 10 ng REV-ERBα and 280 ng BSM. Compounds were tested at 10 µM concentration. Compounds 72, 4, 7 and 11 show significant antagonistic activity, increasing Bmal-luc expression, while compound AG2 is an agonist, reducing the signal of Bmal-luc. (* for $p<0.05$,  for $p<0.01$ and * for $p<0.001$)

The resulting data are shown in FIG. 4, expressed as the average and standard error obtained from two independent experiments carried out in triplicate. Compound 72 gave an observed inhibitory effect on REV-ERB greater than that obtained using SR8278, with the result being statistically significant (* for $p<0.05$,  for $p<0.01$ and * for $p<0.001$), indicating that it is stronger REV-ERBα antagonists than SR8278.

Example 4—Screening of Further Compounds for REV-ERBα Antagonist Activity

The method of Example 2 was repeated using Compounds 64 to 66, 69 and 70 to 73 (generated as described in Example 1). Once again, Compounds 4, 7 and 11 (tested in Example 2) were used as a positive control for REV-ERB inhibitory activity, agonist compound AG2 (also tested in Example 2) and DMSO were also tested as comparators.

Figure 5:
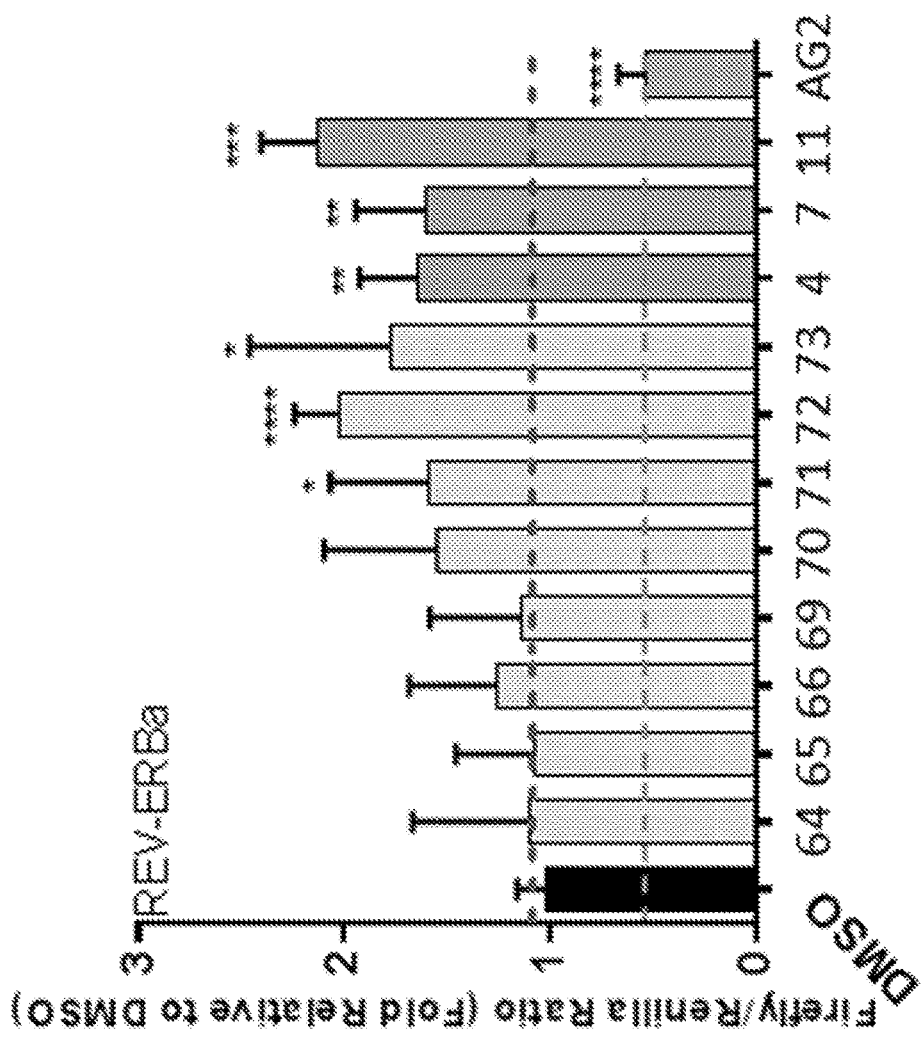
FIG. 5: Effect of further newly generated compounds on REV-ERBα activity. Dual-luciferase result for drug screening using 10 ng $Renilla$, 100 ng Bmal-luc, 10 ng REV-ERBα and 280 ng BSM. Compounds were tested at 10 µM concentration. Compounds 71 to 73, 4, 7 and 11 show significant antagonistic activity, increasing Bmal-luc expression, while compound AG2 is an agonist, reducing the signal of Bmal-luc. (* for $p<0.05$,  for $p<0.01$, * for $p<0.001$ and **** for $p<0.0001$)

The resulting data are shown in FIG. 5, expressed as the average and standard error obtained from three independent experiments carried out in triplicate. Inhibitory effect on REV-ERB was observed for all the compounds, and particularly with Compounds 71 to 73, with the results being statistically significant (* for $p<0.05$,  for $p<0.01$, * for $p<0.001$ and **** for $p<0.0001$).

Example 5—Screening of Compounds for REV-ERBB Antagonist Activity

The method of Example 2 was repeated but with 10 ng of REV-ERBβ used in place of REV-ERBa. Compounds 4, 66, 69 and 73 were tested (generated as described in Example 1). Agonist compound AG2 and DMSO were also tested as comparators.

Figure 6:
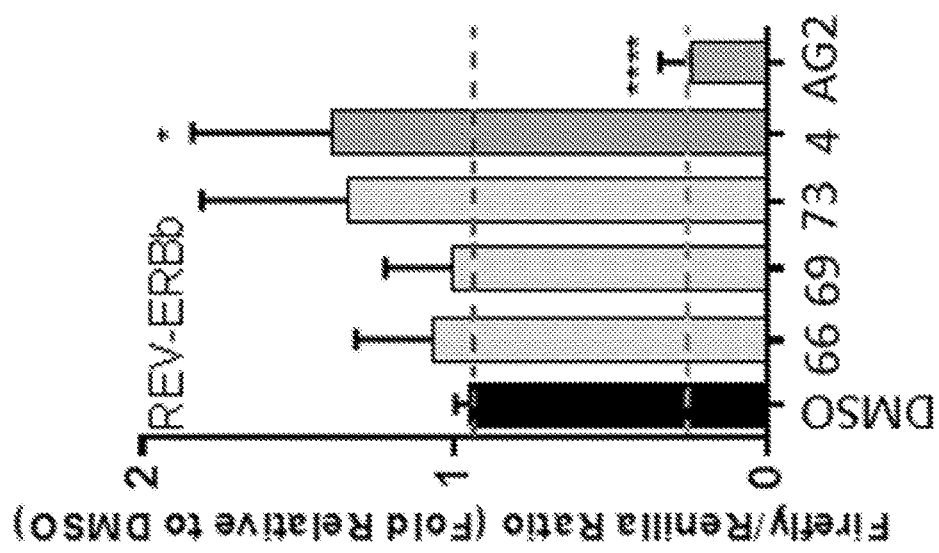
FIG. 6: Effect of newly generated compounds on REV-ERBβ activity. Dual-luciferase result for drug screening using 10 ng $Renilla$, 100 ng Bmal-luc, 10 ng REV-ERBβ and 280 ng BSM. Compounds were tested at 10 µM concentration. Compound 4 shows significant antagonistic activity, increasing Bmal-luc expression, while compound AG2 is an agonist, reducing the signal of Bmal-luc. (* for $p<0.05$ and **** for $p<0.0001$)

The resulting data are shown in FIG. 6, expressed as the average and standard error obtained from three independent experiments carried out in triplicate. Inhibitory effect on REV-ERB was observed for all the compounds, and particularly with Compounds 4, with the result being statistically significant (* for $p<0.05$ and **** for $p<0.0001$).

Example 6—Screening of Further Compounds for REV-ERBα Antagonist Activity

The method of Example 2 was repeated using Compounds 16 to 19, 27, 28 and 44 (generated as described in Example 1). Once again, Compounds 4, 7 and 11 (tested in Example 2) were used as a positive control for REV-ERB inhibitory activity, agonist compound AG2 (also tested in Example 2) and DMSO were also tested as comparators.

Figure 7:
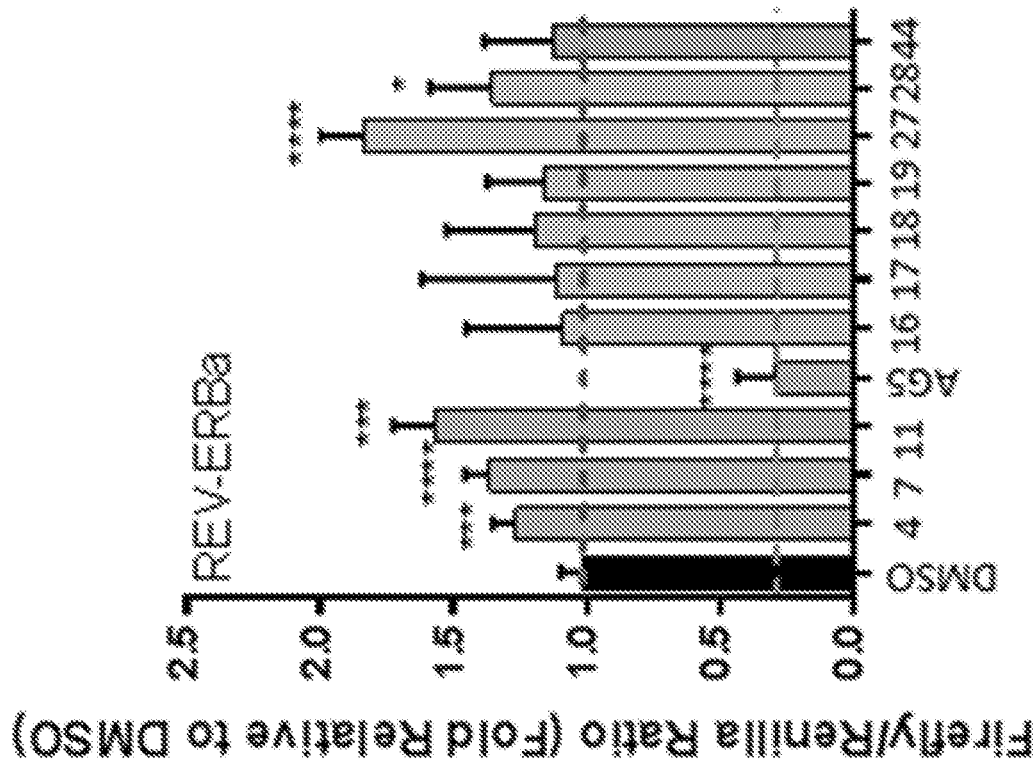
FIG. 7: Effect of further newly generated compounds on REV-ERBα activity. Dual-luciferase result for drug screening using 10 ng $Renilla$, 100 ng Bmal-luc, 10 ng REV-ERBα and 280 ng BSM. Compounds were tested at 10 µM concentration. Compounds 4, 7, 11, 27 and 28 show significant antagonistic activity, increasing Bmal-luc expression, while compound AG5 is an agonist, reducing the signal of Bmal-luc. (* for $p<0.05$, * for $p<0.001$ and ** for $p<0.0001$)

The resulting data are shown in FIG. 7, expressed as the average and standard error obtained from three independent experiments carried out in triplicate. Inhibitory effect on REV-ERB was observed particularly with Compounds 27 and 28, with the results being statistically significant (* for $p<0.05$, * for $p<0.001$ and ** $p<0.0001$).

Example 7—Screening of Further Compounds for REV-ERBB Antagonist Activity

The method of Example 5 was repeated using Compounds 18 and 19 (generated as described in Example 1). Agonist compound AG5 and DMSO were also tested as comparators.

Figure 8:
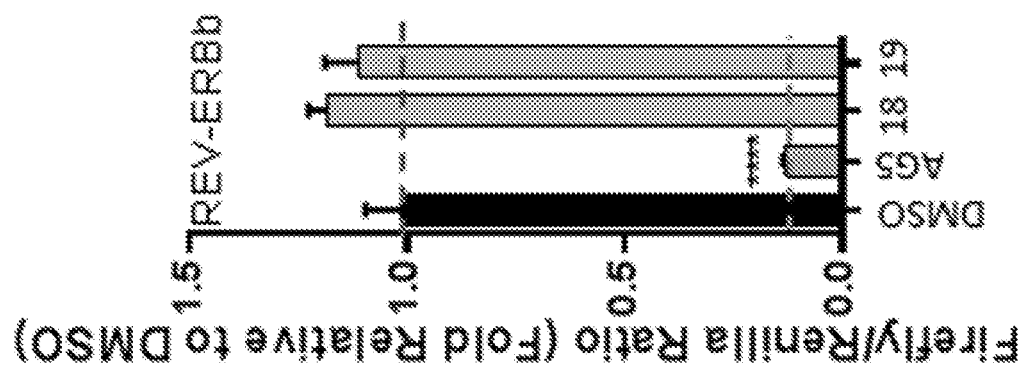
FIG. 8: Effect of further newly generated compounds on REV-ERBβ activity. Dual-luciferase result for drug screening using 10 ng $Renilla$, 100 ng Bmal-luc, 10 ng REV-ERBβ and 280 ng BSM. Compounds were tested at 10 µM concentration. Compounds 18 and 19 show antagonistic activity, increasing Bmal-luc expression, while compound AG2 is an agonist, reducing the signal of Bmal-luc. (**** for $p<0.0001$)

The resulting data are shown in FIG. 8, expressed as the average and standard error obtained from two independent experiments carried out in triplicate. Inhibitory effect on REV-ERB was observed for both compounds. (**** for $p<0.0001$)

Example 8—Inhibitors of REV-ERBα Increase the Total Number of NK Cells Produced

Compounds 7 and 11 were screened along with SR8278. Mice. All mice used in this study were wild type on a C57BL/6 background, between six and twelve weeks old. All animal husbandry and experimental procedures were performed according to UK Home Office regulations and institute guidelines.

OP9 cell line and cell culture. OP9 is a stromal cell line from mouse bone marrow known to support lymphocyte differentiation of hematopoietic progenitors when co-culturing with them. OP9-GFP cells were cultured in Iscove's Modified Dulbecco's Medium (IMDM) (Sigma-Aldrich) supplemented with 20% Fetal Bovine Serum (FBS) and 1% Penicillin/Streptavidin (P/S). They were split into 24-well plates with 2500 cells per well two days before transferring Lin– cells onto them. Cells were kept in a 5% $CO_2$ humidified atmosphere at 37 QC.

Lineage negative cells isolation from bone marrow. Mouse leg and hip bones were crushed in Phosphate Buffered Saline (PBS) with 2% FBS to release bone marrow cells. Cell suspension was filtered through a 40 pam strainer, topped up to 40 mL with PBS+2% FBS and centrifuged at 500×g for 4 minutes. Cells were resuspended in 2 mL PBS+2% FBS and stained with phycoerythrin (PE)-conjugated cocktail (20 µL anti-B220 (RA3/6B2), 20 µL anti-CD2 (RM2-5), 20 µL anti-Ter119 (TER119), 20 µL anti-NK1.1 (PK136), 5 µL anti-CD11b (M1/70) and 5 µL Gr1 (RB6-8C5) antibodies (all from eBioscience) for 5 minutes at 4° C. Then, cells were washed, centrifuged and incubated with anti-PE Microbeads (Miltenyi) for 15 minutes at 4° C. Next, cells were washed with PBS and passed through LD column (Miltenyi), enabling the negative selection of unstained Lin– cells that flowed through the column. 50 µL of cells were taken to check the purity after depletion using flow cytometry.

In vitro NK cell development from lineage negative cells. Lin– cells were plated in 24-well plates with $5\times10^5$ cells in 1 mL of Dulbecco's Modified Eagle Medium (DMEM) (Sigma-Aldrich) supplemented with 10% embryonic stem cell-qualified FBS (ES-FBS), 1% P/S, 50 µM β-Mercaptoethanol (β-ME), 10 ng/ml Flt3-ligand (Flt3L) (R&D Systems), 10 ng/mL IL-7 (R&D Systems) and 100 ng/mL stem cell factor (SCF) (R&D Systems) per well and cultured for 2 days. Cells were transferred for co-culture with OP9-GFP stromal cells in 24-well plates with $3\times10^4$ cells in 1 mL of Alpha MEM (Sigma-Aldrich) supplemented with 20% ES-FBS, 1% P/S, 50 µM β-ME and 10 ng/mL IL-15 (R&D Systems) per well and cultured for 7. Compounds were added on day 2, at the same time as cells were transferred together with OP9. Supernatant was removed on day 5, and new media was added with compound. Cells were kept in a 5% $CO_2$ humidified atmosphere at 37° C.

Flow cytometry. After being cultured for 7 days, cells were harvested, filtered through 40 µm strainers to remove OP9 cells and washed with PBS. After centrifuging at 500×g for 5 minutes at 4° C., they were stained with appropriate fluorochrome conjugated antibodies with 1:300 dilution in 100 µL of fluorescent activated cell sorting (FACS) buffer (PBS with 1% BSA) for 15 minutes at 4° C. in the dark. Antibodies include CD3(e450), NK1.1(APC), NKp46(Percp e710) and PI, all of which are anti-mouse and from eBioscience. Cells were then washed in 1 ml FACS buffer, centrifuged and resuspended in 300 µL FACS buffer. Compensation was set up using Anti-Mouse Ig, k and Anti-Rat/Hamster Ig, k Compensation Particles Set (BDTM Combead). Flow cytometry analysis was carried out using BD LSRFortessa™ cell analyser (Becton Dickinson Bioscience) and data analysis was performed using FlowJo.

Figure 9:
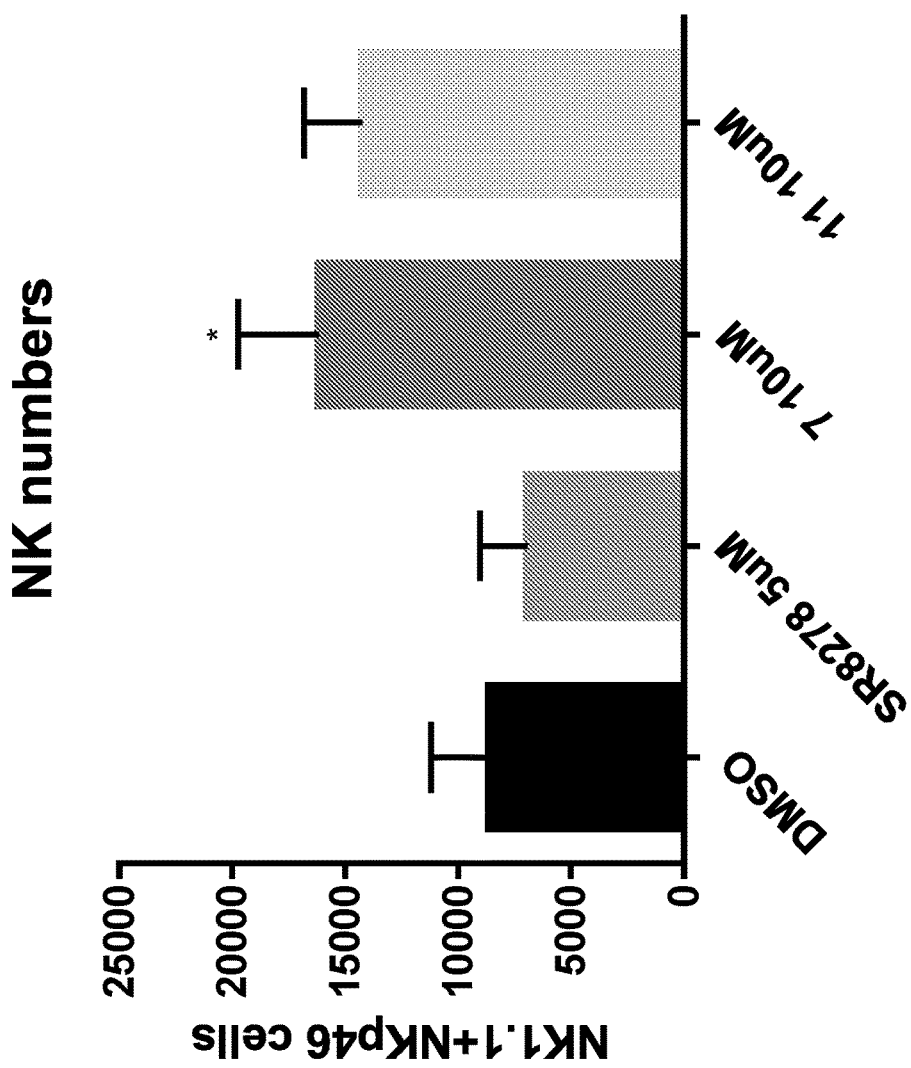
FIG. 9: NK cells development assay results showing the total number of NK cells for each assay condition. Compound 7 shows a significant increase in NK cell number, with an increase also observed for Compound 11 compared with SR8278 and agonist compound AG2. (* for $p<0.05$)

Addition of 10 µM of Compounds 7 and 11 both showed an increase in the total number of NK cells compared with SR8278 with a significant increase in the case of Compound 7 (FIG. 9) (* for $p<0.05$).

Example 8—Further Inhibitors of REV-ERBα Increase the Total Number of NK Cells Produced The method of Example 7 was repeated using 5 µM of Compounds 7 and 11, and 5 and 10 µM of Compound 72.

Figure 10:
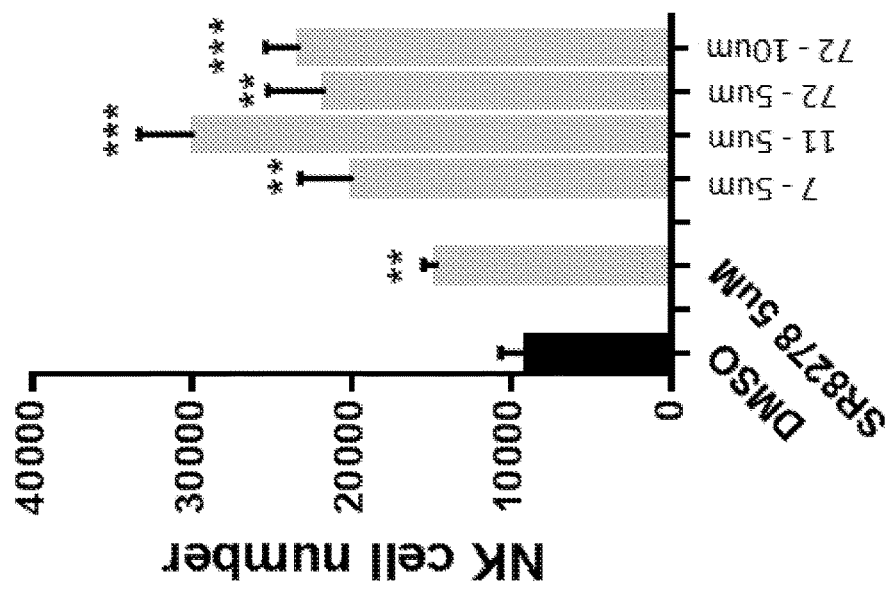
FIG. 10: NK cells development assay results showing the total number of NK cells for each assay condition. Compounds 7, 11 and 72 show a significant increase in NK cell number compared with SR8278 and agonist compound AG2. ( for $p<0.01$ and * for $p<0.001$)

Addition of 5 µM of 7 and 11 as well as 5 and 10 µM of Compound 72 showed a significant increase in the total number of NK cells compared with SR8278 (FIG. 10) ( for $p<0.01$, * for $p<0.001$).

The invention claimed is:

1. An ex vivo method for expanding an NK cell population, comprising the steps of:
    a) culturing an haematopoietic progenitor cell (HPC) comprising sample obtained from an individual;
    b) contacting said sample with a compound that inhibits the action of REV-ERB; and
    c) expanding said cells in vitro to produce an NK cell population;
    wherein the compound has formula (I):

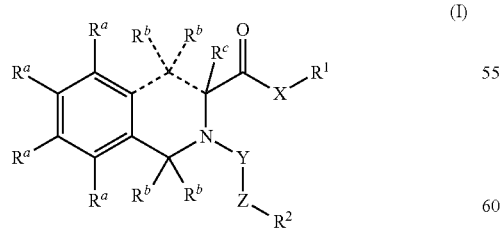

where: ------ represents bonds that are all either present or absent;
$R^1$ is selected from $C_{1-6}$ hydrocarbyl, and is optionally substituted with one or more groups independently selected from $C_{1-4}$ hydrocarbyl, —OR', —OC(O)R', —C(O)OR', —SR', —S(O)R', —S(O)$_2$R', —NR'$_2$, —NR'C(O)R', —C(O)NR'$_2$, —CN, —NO$_2$, -Ph, —CF$_3$ and halogen;

$R^2$ is selected from 5-10 membered heterocyclyl rings and $C_{1-6}$ hydrocarbyl, and is optionally substituted with one or more groups independently selected from $C_{1-4}$ hydrocarbyl, —OR', —OC(O)R', —C(O)OR', —SR', —S(O)R', —S(O)$_2$R', —NR'$_2$, —NR'C(O)R', —C(O)NR'$_2$, —CN, —NO$_2$, -Ph, —CF$_3$ and halogen;

X is selected from —O— and —NR'— or is absent;
Y is selected from —C(O)— or —CR'$_2$—;
Z is selected from —O— and —NR'— or is absent;
each $R^a$ is independently selected from H, $C_{1-4}$ hydrocarbyl, —OR', —OC(O)R', —C(O)OR', —SR', —S(O)R', —S(O)$_2$R', —NR'$_2$, —NR'C(O)R', —C(O)NR'$_2$, —CN, —NO$_2$, -Ph, —CF$_3$ and halogen;
each $R^b$ is independently selected from H, $C_{1-4}$ hydrocarbyl and —OR';
$R^c$ is selected from H and $C_{1-4}$ hydrocarbyl; and
each R' is independently selected from H, $C_{1-4}$ hydrocarbyl and -Ph;
or a pharmaceutically acceptable salt thereof, provided that the compound is not:

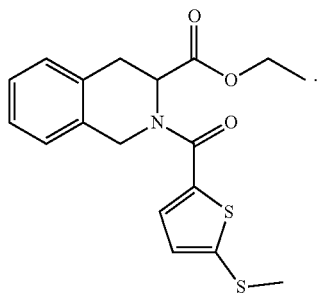 [SMILES: CCOC(=O)C1Cc2ccccc2CN1C(=O)c1ccc(SC)s1]

2. The method of claim 1, wherein ------ represents bonds that are all present and the compound is a closed ring structure according to formula Ia:

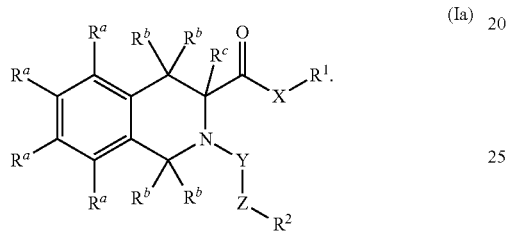

3. The method of claim 1, wherein $R^1$ is unsubstituted.
4. The method of claim 1, wherein:
$R^2$ is selected from:
  (i) optionally substituted 5-10 membered heterocyclyl rings; and
  (ii) optionally substituted phenyl; and/or
$R^2$ is unsubstituted or substituted with one or two groups independently selected from $C_{1-4}$ alkyl, —OR', —OC(O)R', —C(O)OR', —SR', —S(O)R', —S(O)$_2$R', —NR'$_2$, —NR'C(O)R', —C(O)NR'$_2$, —CN, —NO$_2$, -Ph, —CF$_3$ and halogen.
5. The method of claim 1, wherein:
  a) X is —O—;
  b) Y is —C(O)—;
  c) Z is —O— or is absent;
  d) each $R^a$ is independently selected from H, $C_{1-4}$ alkyl and —OR';
  e) each $R^b$ is independently selected from H and $C_{1-4}$ alkyl;
  f) $R^c$ is H; and/or
  g) each R' is independently selected from H and $C_{1-4}$ alkyl.
6. The method of claim 1, wherein $R^b$ and $R^c$ are all H, such that the compound has the formula (II):

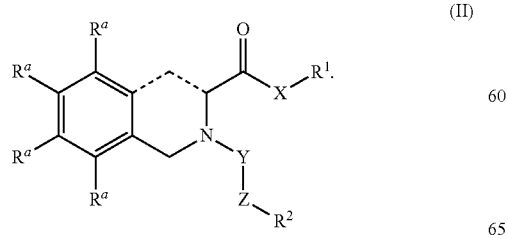

7. The method of claim 6, wherein $R^a$ are all H, such that the compound has the formula (III):

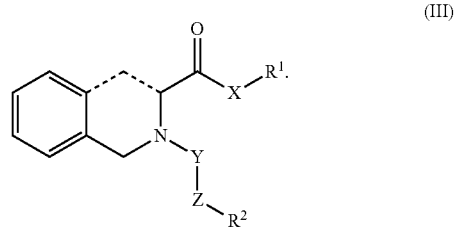

8. The method of claim 1, wherein the compound has a formula selected from:

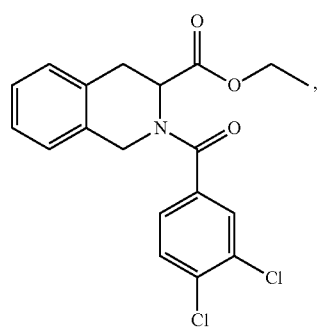

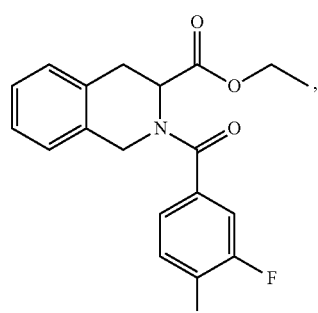

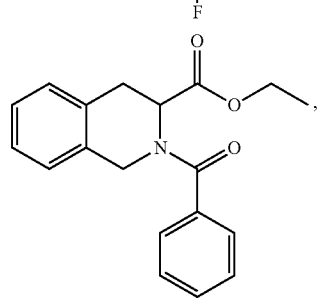

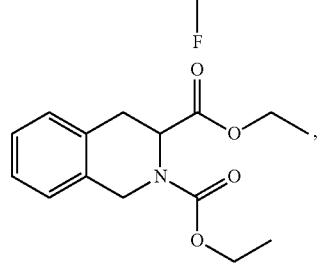

143
-continued
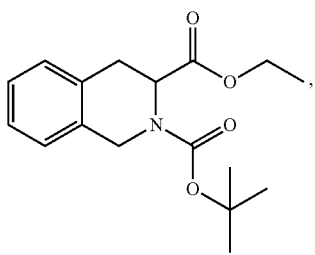
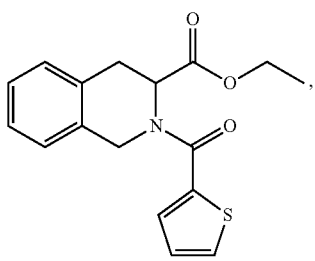
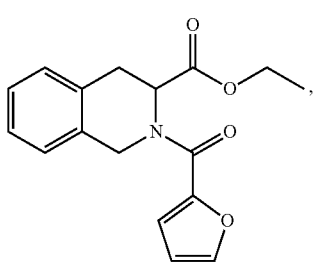
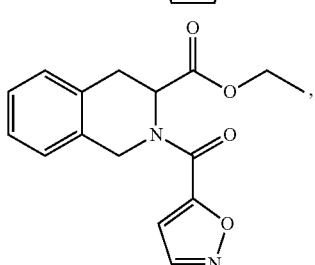
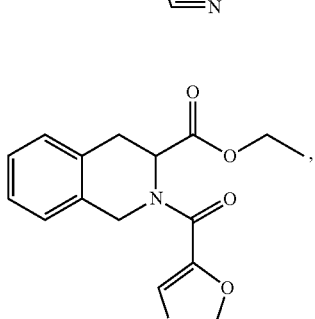
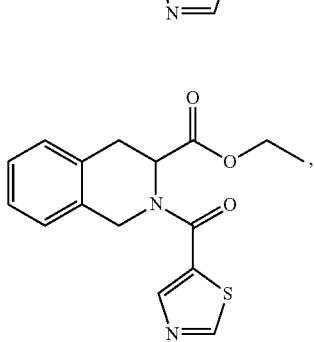
144
-continued
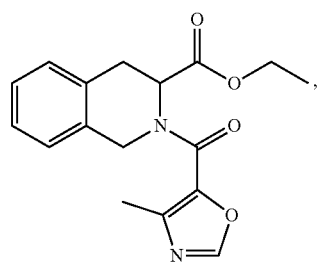
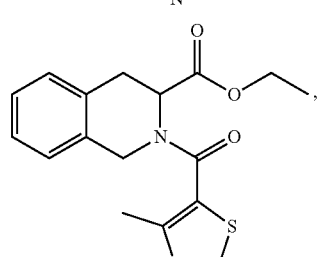
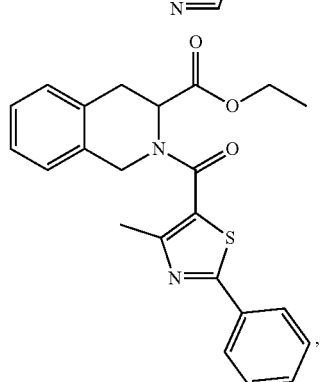
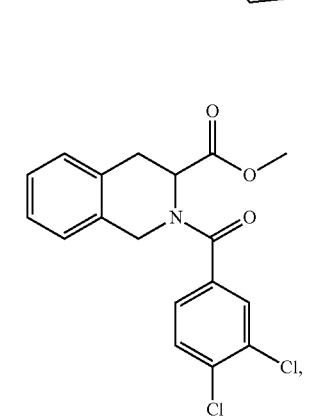
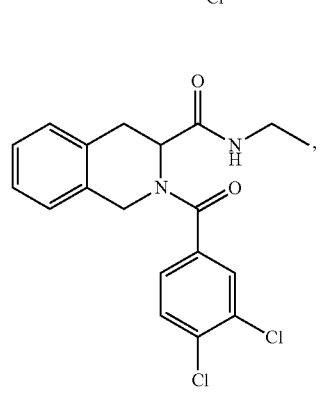

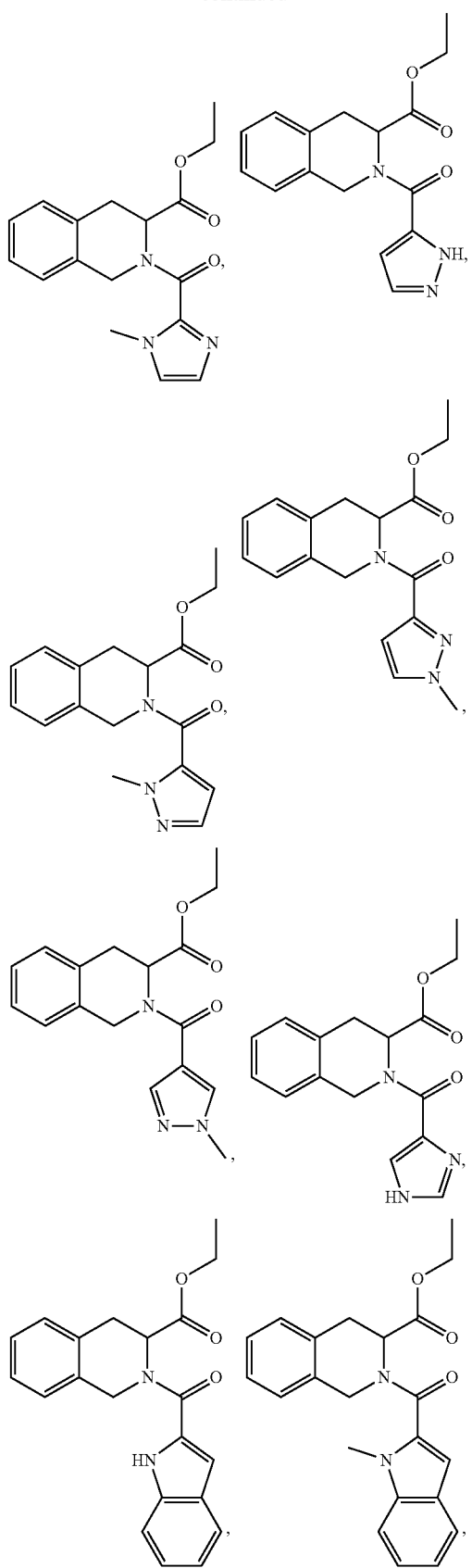
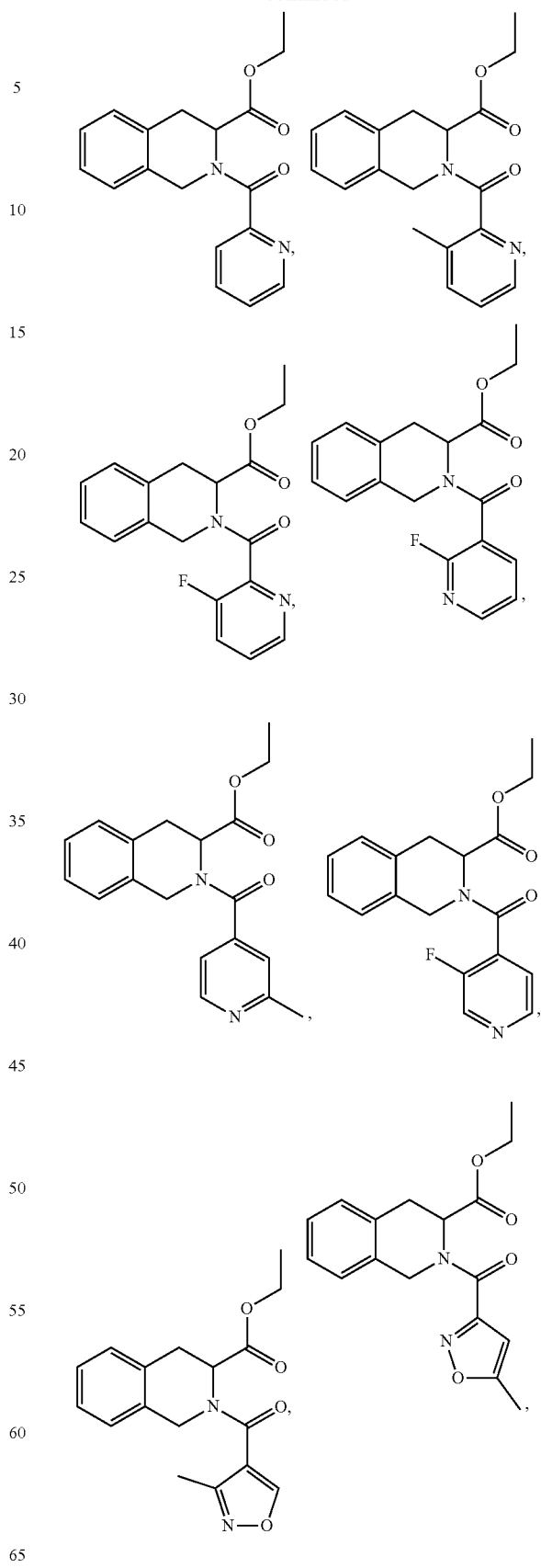

-continued
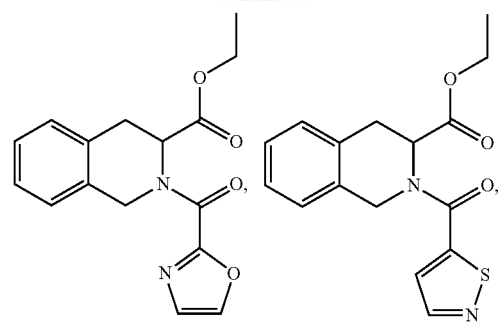
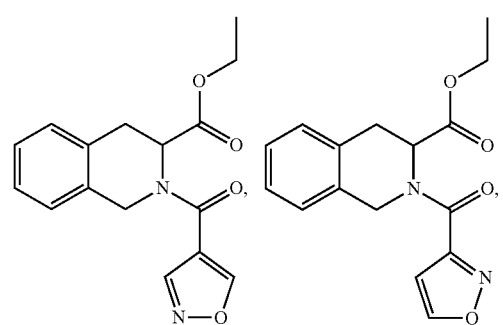
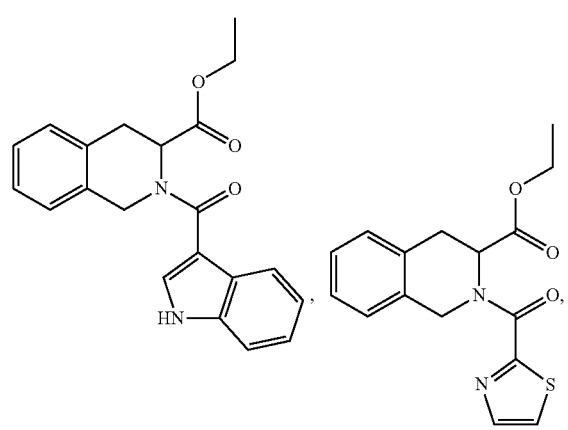
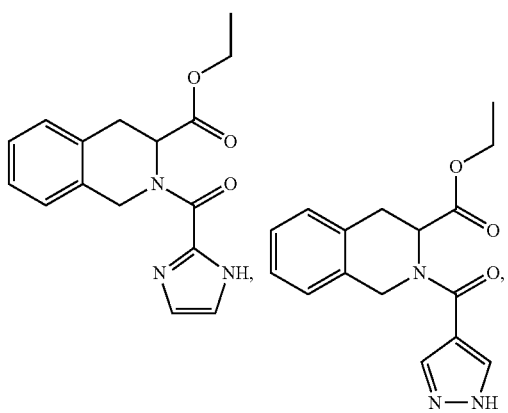
-continued
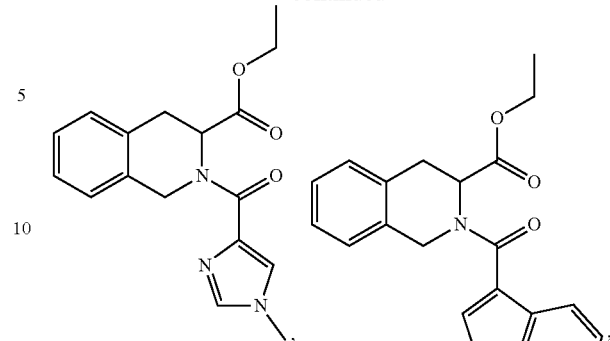
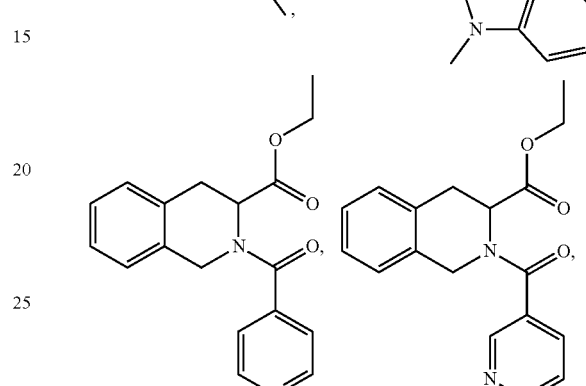
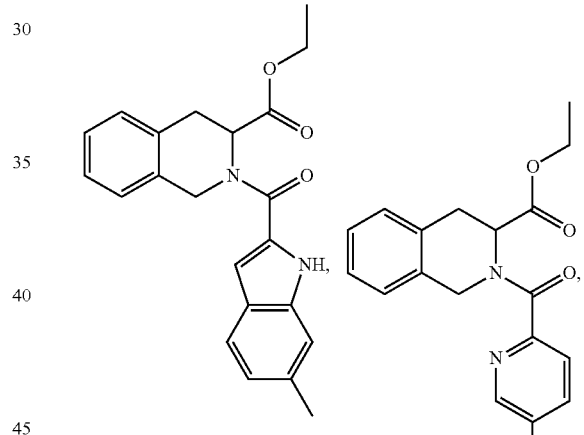
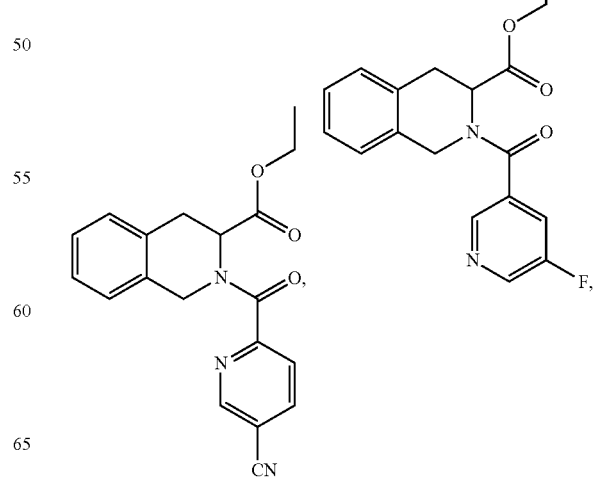

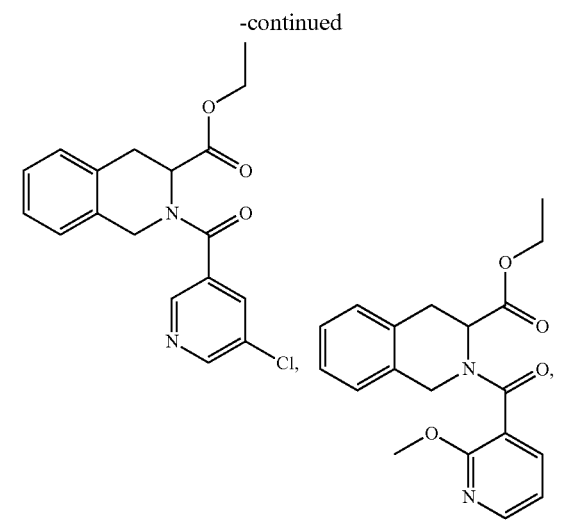
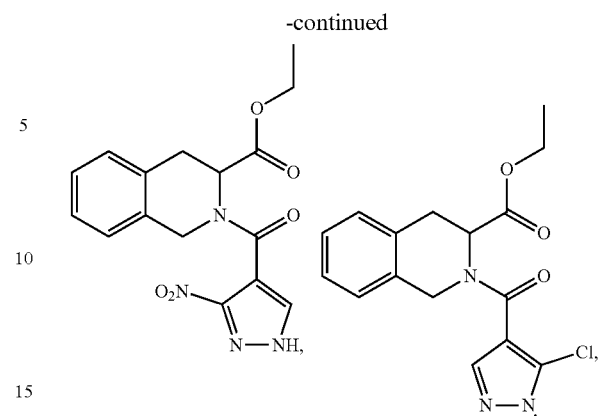
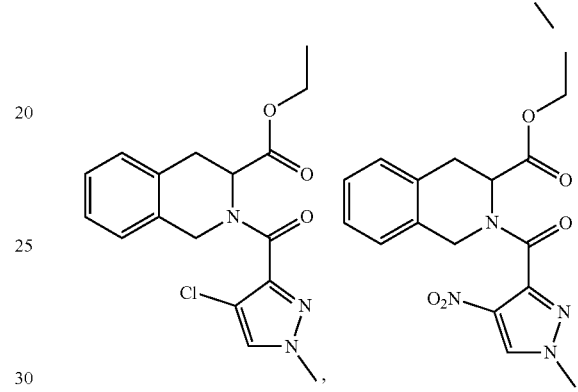
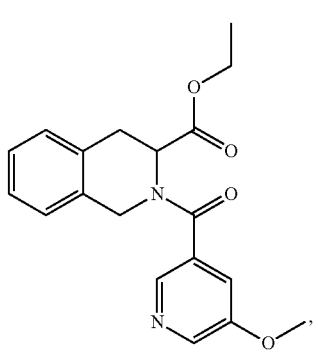
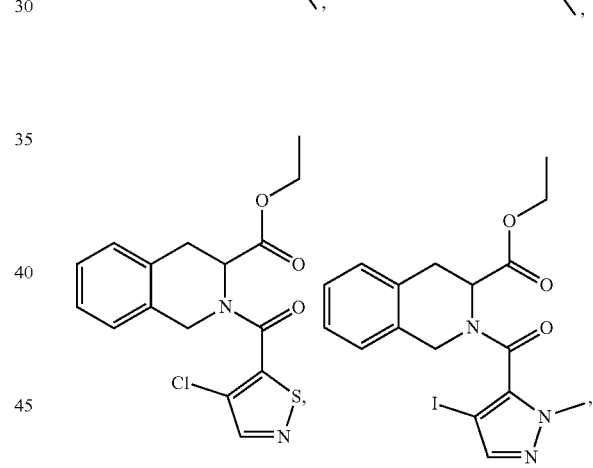
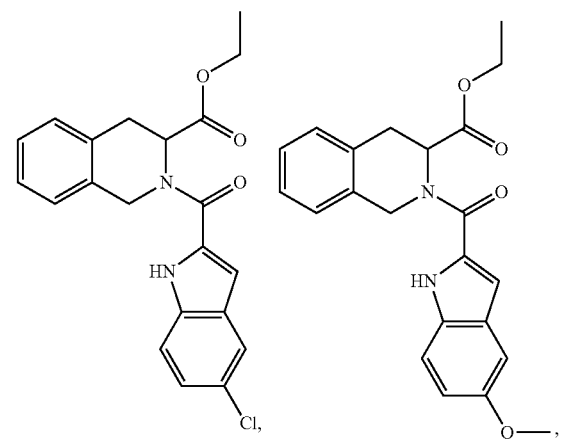
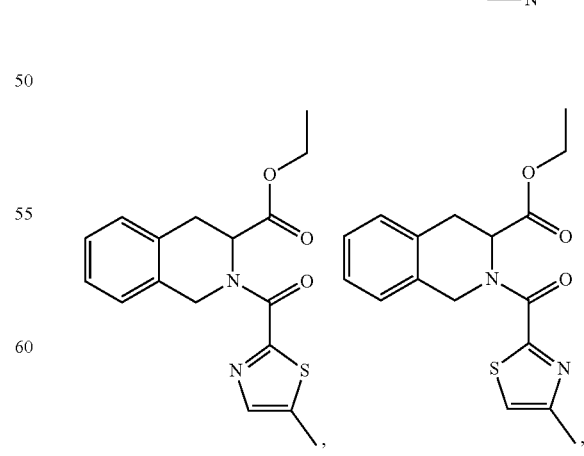

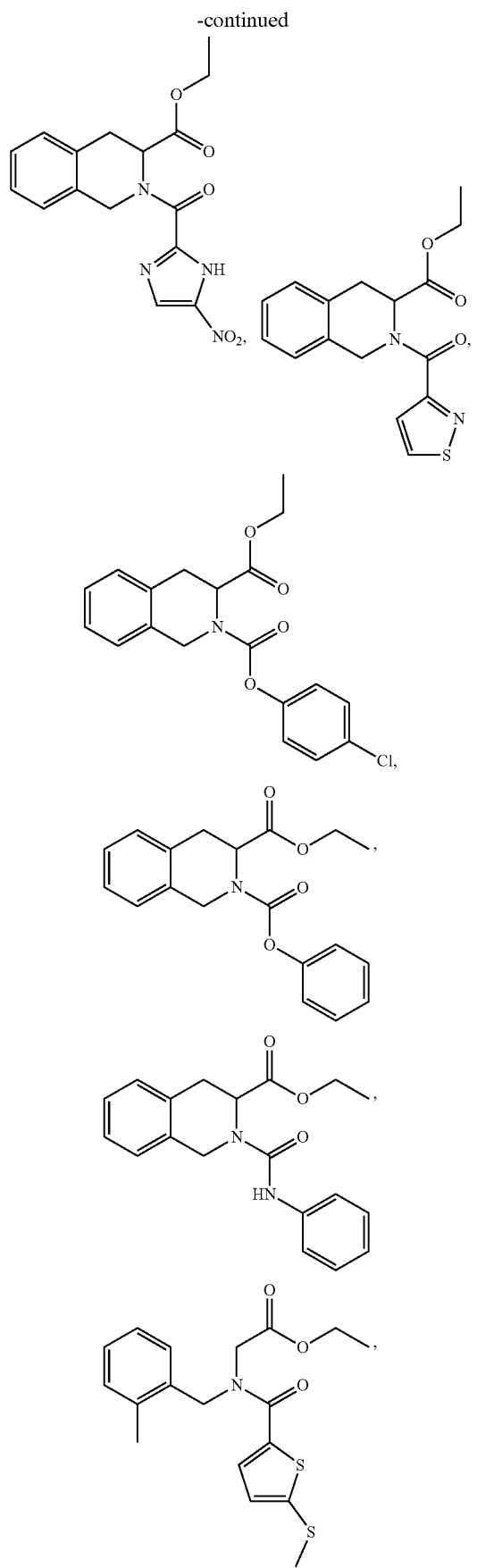
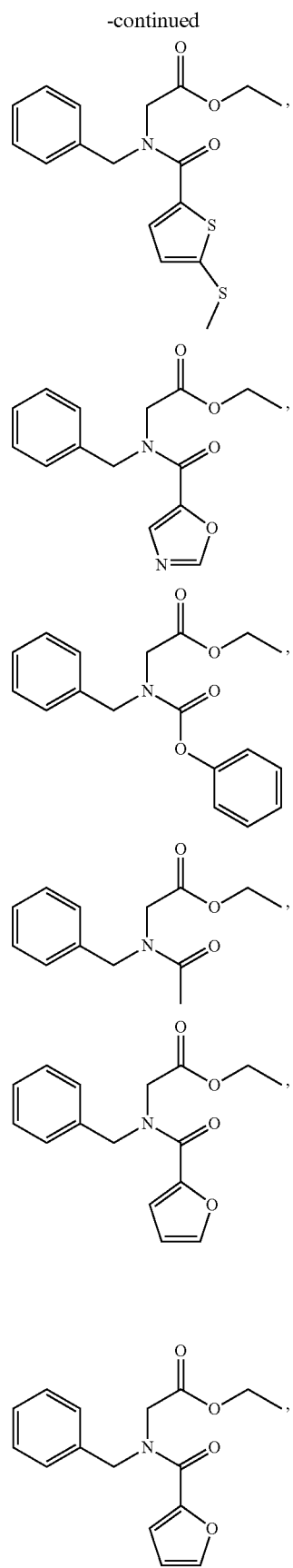

-continued

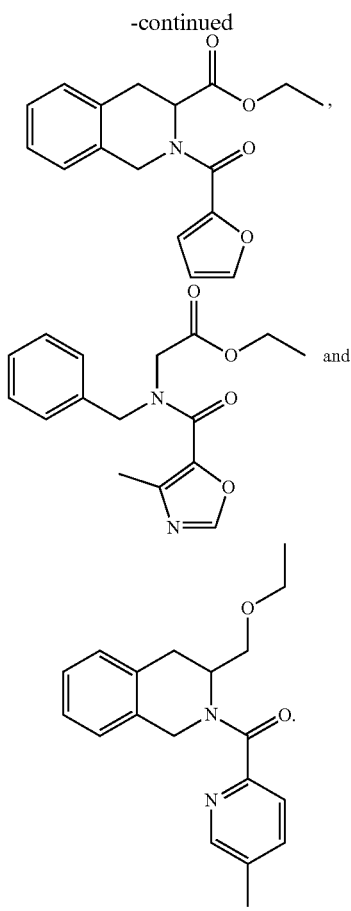

and

9. The method of claim 1, wherein said compound increases E4bp4 expression by decreasing REV-ERB activity.

10. The method of claim 1, wherein said compound decreases the activity of REV-ERB-α and/or REV-ERB-β.

11. The method of claim 1, wherein said compound is a REV-ERB antagonist.

12. The method of claim 1, which further comprises a step of culturing the HPCs in the presence of a Notch ligand, wherein optionally the vessel in which the HPCs are cultured is coated with the Notch ligand.

13. The method of claim 12, wherein:
a) the Notch ligand is delta-like ligand 4 (DLL4), or a fragment thereof which retains the function of DLL4; and/or
b) the Notch ligand is present on or from 4 days after isolating said HPCs.

14. The method of claim 12, wherein:
a) the cells are cultured in the presence of IL-15 after the step of culturing in the presence of the Notch ligand; and/or
b) the HPCs are cultured in the presence of the Notch ligand in combination with IL-7, Flt3L and/or stem cell factor (SCF);
wherein optionally either or both of the step of culturing in the cells in the presence of the Notch ligand and the step of culturing in the presence of IL-15 are carried out in the absence of a stromal support cell.

15. The method of claim 1, which further comprises the step of contacting the HPCs with a compound which results in alteration of the post-translational modification of E4bp4, thereby causing an increase in E4bp4 activity;
wherein optionally the alteration of post-translational modification of E4bp4 is a reduction in SUMOylation and/or phosphorylation of E4bp4.

16. The method of claim 1, wherein the sample of HPCs is obtained from bone marrow, cord blood and/or peripheral blood.

17. A compound which inhibits the action of REV-ERB activity for use in a method of therapy by increasing production of natural killer (NK) cells in a patient, wherein said compound is as defined in claim 1.

18. The compound for use of claim 17, wherein said method of therapy is:
a) a method of treating a disease or disorder selected from cancer, an infectious disease, an autoimmune disease or a disease or disorder related to female infertility or pregnancy; or
b) a method of treatment of a viral infection, a bacterial infection, a protist infection, a fungal infection and/or a helminth infection.

19. The compound for use of claim 17, which is used in combination with antibody-mediated immunotherapy, wherein optionally said compound is for administration before, simultaneously with, or after administration of the antibody-mediated immunotherapy.

20. Products containing a compound which inhibits the action of REV-ERB and a Notch ligand as a combined preparation for simultaneous, separate or sequential use in a method of therapy by increasing production of natural killer (NK) cells in a patient, wherein said compound is as defined in claim 1, and optionally said Notch ligand is delta-like ligand 4 (DLL4), or a fragment thereof which retains the function of DLL4.

21. A method of treatment by increasing the number of NK cells in a patient in need thereof, comprising administering to said patient a therapeutically effective amount of a compound which inhibits the action of REV-ERB as defined in claim 1, and optionally a Notch ligand.

22. A compound of formula (I) as defined in claim 1, provided that the compound is not:

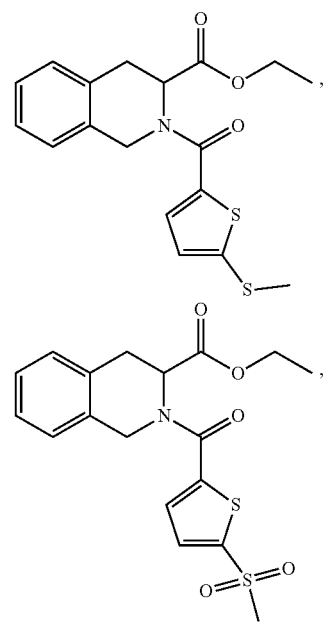

155
-continued
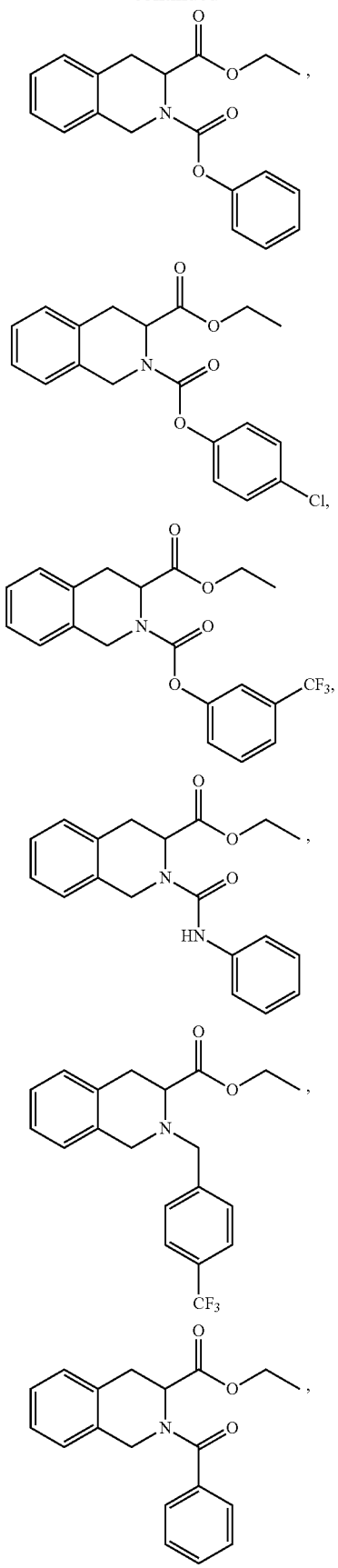
156
-continued
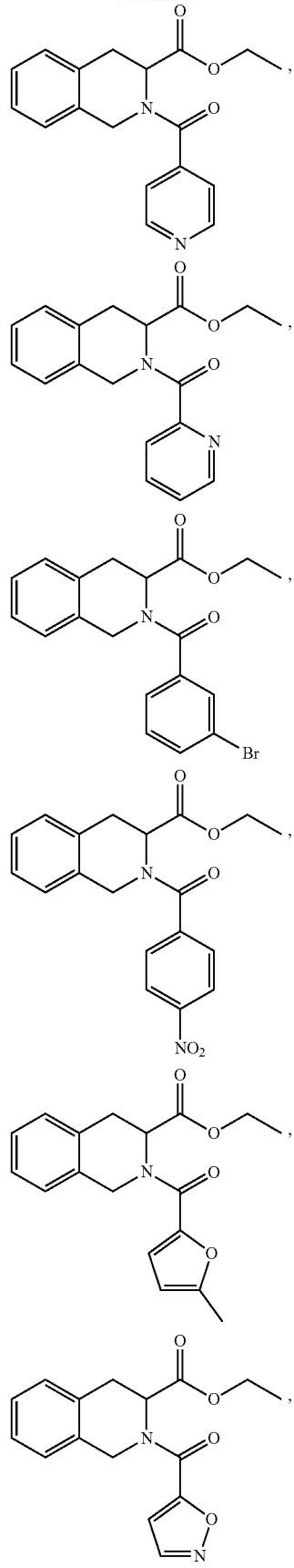

157
-continued
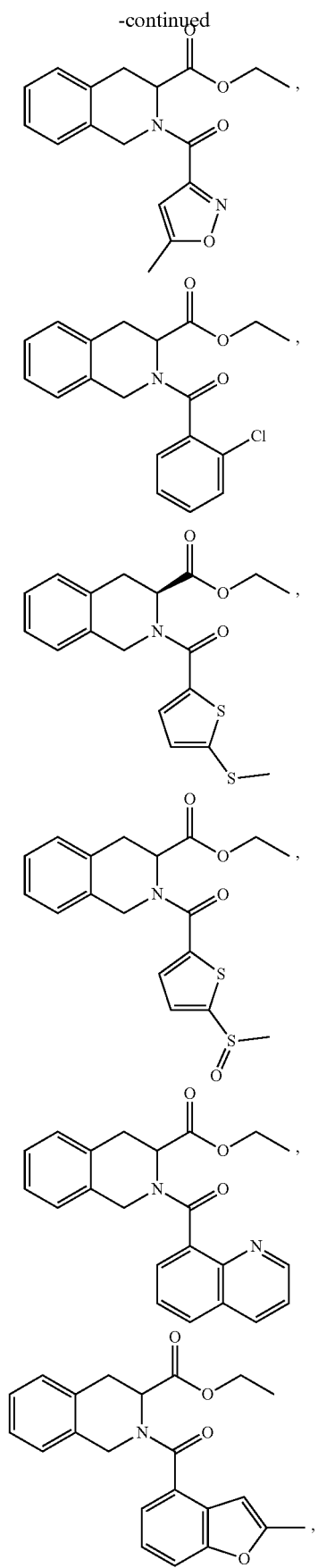
158
-continued
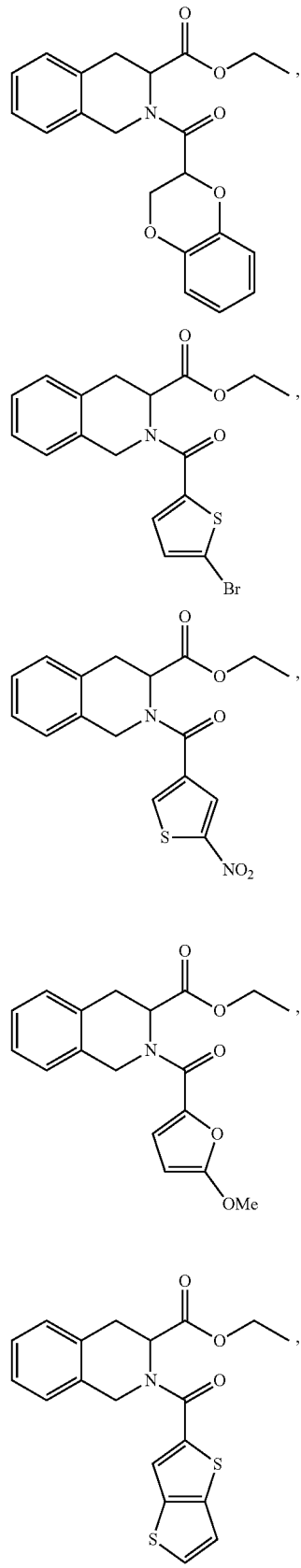

159
-continued
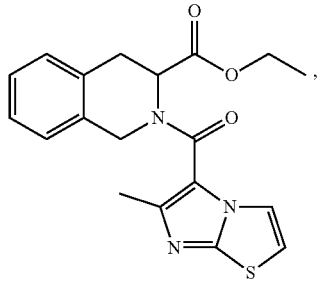
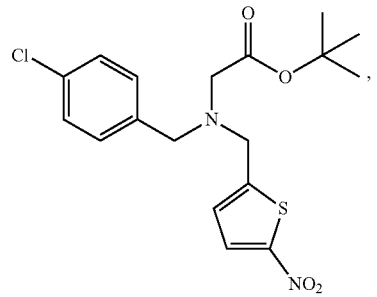
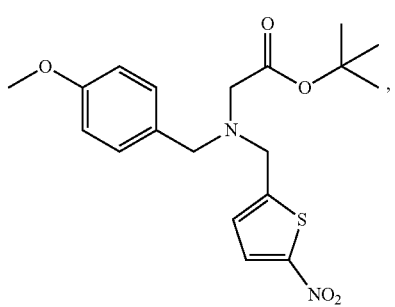
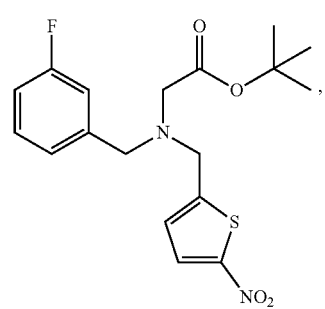
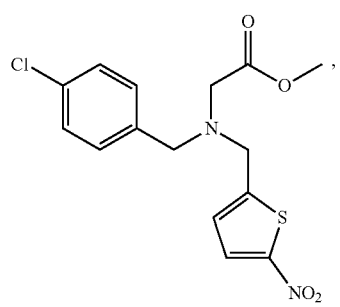
160
-continued
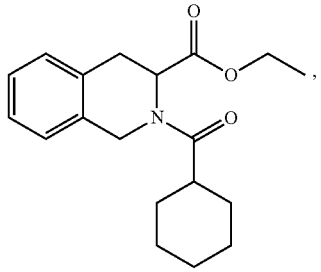
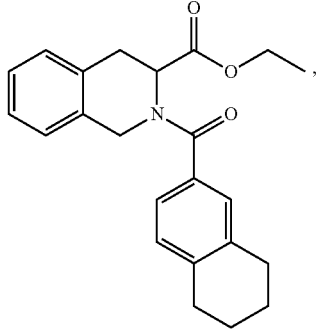
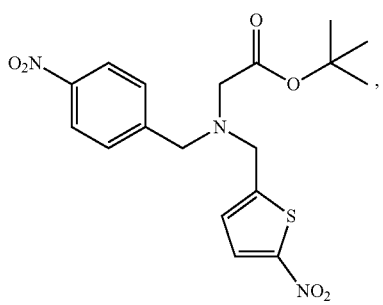
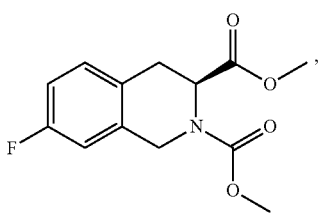
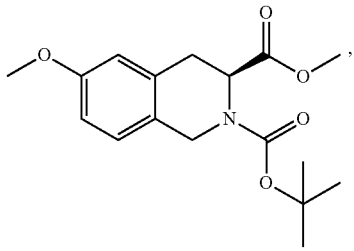
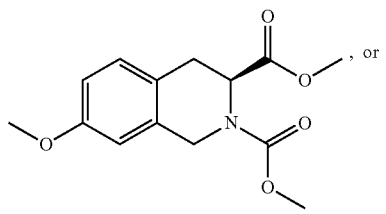

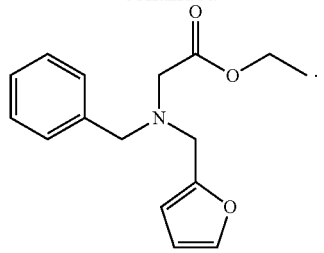
* * * * *